US010801028B2

(12) United States Patent
Sela et al.

(10) Patent No.: US 10,801,028 B2
(45) Date of Patent: *Oct. 13, 2020

(54) COMPOSITIONS FOR CONTROLLING *VARROA* MITES IN BEES

(71) Applicants: Yissum Research Development Company of the Hebrew University of Jerusalem Ltd., Jerusalem (IL); Beeologics, Inc., St. Louis, MO (US)

(72) Inventors: Ilan Sela, Ramot-HaShavim (IL); Sharoni Shafir, Nes Ziona (IL); Eyal Maori, Rishon-LeZion (IL); Yael Garbian, Rishon-LeZion (IL); Eyal Ben-Chanoch, Miami, FL (US); Gal Yarden, Nir-Moshe (IL); Haim Kalev, Kfar-HaNagid (IL)

(73) Assignees: BEEOLOGICS INC., St. Louis, MO (US); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/498,008

(22) Filed: Apr. 26, 2017

(65) Prior Publication Data

US 2017/0233743 A1 Aug. 17, 2017

Related U.S. Application Data

(63) Continuation of application No. 14/606,328, filed on Jan. 27, 2015, now Pat. No. 9,662,348, which is a continuation of application No. 13/446,557, filed on Apr. 13, 2012, now Pat. No. 8,962,584, which is a continuation-in-part of application No. PCT/IL2010/000844, filed on Oct. 14, 2010.

(60) Provisional application No. 61/251,339, filed on Oct. 14, 2009.

(51) Int. Cl.
*C12N 15/11* (2006.01)
*C12N 15/113* (2010.01)
*A61K 31/713* (2006.01)
*A23K 20/147* (2016.01)
*A23K 20/163* (2016.01)
*A23K 50/90* (2016.01)
*A23K 20/10* (2016.01)

(52) U.S. Cl.
CPC ......... *C12N 15/1137* (2013.01); *A23K 20/10* (2016.05); *A23K 20/147* (2016.05); *A23K 20/163* (2016.05); *A23K 50/90* (2016.05); *A61K 31/713* (2013.01); *C12N 15/113* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,732,250 A | 3/1988 | Maucher et al. |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |

(Continued)

FOREIGN PATENT DOCUMENTS

AU 2008325989 A1 5/2009
AU 2008258254 B2 7/2014
(Continued)

OTHER PUBLICATIONS

Amdam et al, Altered Physiology in Worker Honey Bees (*Hymenoptera: apidae*) Infested with the Mite Varroa destructor (*Acari: varroidae*): A Factor in Colony Loss During Overwintering? J. Econ. Entomol.,2004, v.97, 3:741-747 (Year: 2004).*

(Continued)

*Primary Examiner* — Ekaterina Poliakova-Georgantas
(74) *Attorney, Agent, or Firm* — Arnold & Porter Kaye Scholer LLP; Amanda Camany-Rampey; David R. Marsh

(57) ABSTRACT

An isolated nucleic acid agent is disclosed comprising a nucleic acid sequence which downregulates expression of a gene product of a *Varroa destructor* mite. Compositions comprising same and uses thereof are also disclosed.

18 Claims, 11 Drawing Sheets
Specification includes a Sequence Listing.

(56) References Cited

U.S. PATENT DOCUMENTS

| | | | |
|---|---|---|---|
| 4,940,835 | A | 7/1990 | Shah et al. |
| 4,971,908 | A | 11/1990 | Kishore et al. |
| 5,004,863 | A | 4/1991 | Umbeck |
| 5,011,771 | A | 4/1991 | Bellet et al. |
| 5,013,659 | A | 5/1991 | Bedbrook et al. |
| 5,015,580 | A | 5/1991 | Christou et al. |
| 5,023,243 | A | 6/1991 | Tullis |
| 5,034,506 | A | 7/1991 | Summerton et al. |
| 5,094,945 | A | 3/1992 | Comai |
| 5,141,870 | A | 8/1992 | Bedbrook et al. |
| 5,145,783 | A | 9/1992 | Kishore et al. |
| 5,159,135 | A | 10/1992 | Umbeck |
| 5,166,315 | A | 11/1992 | Summerton et al. |
| 5,177,196 | A | 1/1993 | Meyer, Jr. et al. |
| 5,185,444 | A | 2/1993 | Summerton et al. |
| 5,188,642 | A | 2/1993 | Shah et al. |
| 5,188,897 | A | 2/1993 | Suhadolnik et al. |
| 5,192,659 | A | 3/1993 | Simons |
| 5,214,134 | A | 5/1993 | Weis et al. |
| 5,216,141 | A | 6/1993 | Benner |
| 5,235,033 | A | 8/1993 | Summerton et al. |
| 5,264,423 | A | 11/1993 | Cohen et al. |
| 5,264,562 | A | 11/1993 | Matteucci |
| 5,264,564 | A | 11/1993 | Matteucci |
| 5,272,057 | A | 12/1993 | Smulson et al. |
| 5,276,019 | A | 1/1994 | Cohen et al. |
| 5,278,302 | A | 1/1994 | Caruthers et al. |
| 5,281,521 | A | 1/1994 | Trojanowski et al. |
| 5,286,634 | A | 2/1994 | Stadler et al. |
| 5,286,717 | A | 2/1994 | Cohen et al. |
| 5,304,732 | A | 4/1994 | Anderson et al. |
| 5,310,667 | A | 5/1994 | Eichholtz et al. |
| 5,312,910 | A | 5/1994 | Kishore et al. |
| 5,321,131 | A | 6/1994 | Agrawal et al. |
| 5,331,107 | A | 7/1994 | Anderson et al. |
| 5,339,107 | A | 8/1994 | Henry et al. |
| 5,346,107 | A | 9/1994 | Bouix et al. |
| 5,378,824 | A | 1/1995 | Bedbrook et al. |
| 5,390,667 | A | 2/1995 | Kumakura et al. |
| 5,392,910 | A | 2/1995 | Bell et al. |
| 5,393,175 | A | 2/1995 | Courville |
| 5,399,676 | A | 3/1995 | Froehler |
| 5,405,938 | A | 4/1995 | Summerton et al. |
| 5,405,939 | A | 4/1995 | Suhadolnik et al. |
| 5,416,011 | A | 5/1995 | Hinchee et al. |
| 5,453,496 | A | 9/1995 | Caruthers et al. |
| 5,455,233 | A | 10/1995 | Spielvogel et al. |
| 5,459,127 | A | 10/1995 | Felgner et al. |
| 5,460,667 | A | 10/1995 | Moriyuki et al. |
| 5,462,910 | A | 10/1995 | Ito et al. |
| 5,463,174 | A | 10/1995 | Moloney et al. |
| 5,463,175 | A | 10/1995 | Barry et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,489,520 | A | 2/1996 | Adams et al. |
| 5,489,677 | A | 2/1996 | Sanghvi et al. |
| 5,491,288 | A | 2/1996 | Chaubet et al. |
| 5,510,471 | A | 4/1996 | Lebrun et al. |
| 5,518,908 | A | 5/1996 | Corbin et al. |
| 5,519,126 | A | 5/1996 | Hecht |
| 5,536,821 | A | 7/1996 | Agrawal et al. |
| 5,538,880 | A | 7/1996 | Lundquist et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,550,318 | A | 8/1996 | Adams et al. |
| 5,550,398 | A | 8/1996 | Kocian et al. |
| 5,550,468 | A | 8/1996 | Häberlein et al. |
| 5,558,071 | A | 9/1996 | Ward et al. |
| 5,561,225 | A | 10/1996 | Maddry et al. |
| 5,561,236 | A | 10/1996 | Leemans et al. |
| 5,563,253 | A | 10/1996 | Agrawal et al. |
| 5,569,834 | A | 10/1996 | Hinchee et al. |
| 5,571,799 | A | 11/1996 | Tkachuk et al. |
| 5,587,361 | A | 12/1996 | Cook et al. |
| 5,591,616 | A | 1/1997 | Hiei et al. |
| 5,593,874 | A | 1/1997 | Brown et al. |
| 5,596,086 | A | 1/1997 | Matteucci et al. |
| 5,597,717 | A | 1/1997 | Guerineau et al. |
| 5,602,240 | A | 2/1997 | De Mesmaeker et al. |
| 5,605,011 | A | 2/1997 | Bedbrook et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,061 | A | 5/1997 | Barry et al. |
| 5,633,360 | A | 5/1997 | Bischofberger et al. |
| 5,633,435 | A | 5/1997 | Barry et al. |
| 5,633,448 | A | 5/1997 | Lebrun et al. |
| 5,639,024 | A | 6/1997 | Mueller et al. |
| 5,646,024 | A | 7/1997 | Leemans et al. |
| 5,648,477 | A | 7/1997 | Leemans et al. |
| 5,663,312 | A | 9/1997 | Chaturvedula |
| 5,677,437 | A | 10/1997 | Teng et al. |
| 5,677,439 | A | 10/1997 | Weis et al. |
| 5,714,331 | A | 2/1998 | Buchardt et al. |
| 5,719,046 | A | 2/1998 | Guerineau et al. |
| 5,719,262 | A | 2/1998 | Buchardt et al. |
| 5,721,138 | A | 2/1998 | Lawn |
| 5,731,180 | A | 3/1998 | Dietrich |
| 5,739,180 | A | 4/1998 | Taylor-Smith |
| 5,746,180 | A | 5/1998 | Jefferson et al. |
| 5,767,361 | A | 6/1998 | Dietrich |
| 5,767,373 | A | 6/1998 | Ward et al. |
| 5,780,708 | A | 7/1998 | Lundquist et al. |
| 5,804,425 | A | 9/1998 | Barry et al. |
| 5,824,877 | A | 10/1998 | Hinchee et al. |
| 5,837,848 | A | 11/1998 | Ely et al. |
| 5,859,347 | A | 1/1999 | Brown et al. |
| 5,866,775 | A | 2/1999 | Eichholtz et al. |
| 5,874,265 | A | 2/1999 | Adams et al. |
| 5,879,903 | A | 3/1999 | Strauch et al. |
| 5,898,031 | A | 4/1999 | Crooke |
| 5,914,451 | A | 6/1999 | Martinell et al. |
| 5,919,675 | A | 7/1999 | Adams et al. |
| 5,928,937 | A | 7/1999 | Kakefuda et al. |
| 5,939,602 | A | 8/1999 | Volrath et al. |
| 5,969,213 | A | 10/1999 | Adams et al. |
| 5,981,840 | A | 11/1999 | Zhao et al. |
| 5,985,793 | A | 11/1999 | Sandbrink et al. |
| RE36,449 | E | 12/1999 | Lebrun et al. |
| 6,040,497 | A | 3/2000 | Spencer et al. |
| 6,056,938 | A | 5/2000 | Unger et al. |
| 6,069,115 | A | 5/2000 | Pallett et al. |
| 6,084,089 | A | 7/2000 | Mine et al. |
| 6,084,155 | A | 7/2000 | Volrath et al. |
| 6,107,094 | A | 8/2000 | Crooke |
| 6,118,047 | A | 9/2000 | Anderson et al. |
| 6,121,513 | A | 9/2000 | Zhang et al. |
| 6,130,366 | A | 10/2000 | Herrera-Estrella et al. |
| 6,140,078 | A | 10/2000 | Sanders et al. |
| 6,153,812 | A | 11/2000 | Fry et al. |
| 6,160,208 | A | 12/2000 | Lundquist et al. |
| 6,177,616 | B1 | 1/2001 | Bartsch et al. |
| 6,194,636 | B1 | 2/2001 | McElroy et al. |
| 6,225,105 | B1 | 5/2001 | Sathasivan et al. |
| 6,225,114 | B1 | 5/2001 | Eichholtz et al. |
| 6,232,526 | B1 | 5/2001 | McElroy et al. |
| 6,232,536 | B1 | 5/2001 | McElroy et al. |
| 6,245,968 | B1 | 6/2001 | Boudec et al. |
| 6,248,876 | B1 | 6/2001 | Barry et al. |
| 6,252,138 | B1 | 6/2001 | Karimi et al. |
| RE37,287 | E | 7/2001 | Lebrun et al. |
| 6,268,549 | B1 | 7/2001 | Sailland et al. |
| 6,271,359 | B1 | 8/2001 | Norris et al. |
| 6,282,837 | B1 | 9/2001 | Ward et al. |
| 6,288,306 | B1 | 9/2001 | Ward et al. |
| 6,288,312 | B1 | 9/2001 | Christou et al. |
| 6,294,714 | B1 | 9/2001 | Matsunaga et al. |
| 6,303,374 | B1 | 10/2001 | Zhang et al. |
| 6,326,193 | B1 | 12/2001 | Liu et al. |

(56) References Cited

U.S. PATENT DOCUMENTS

| | | |
|---|---|---|
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,843,985 B2 | 1/2005 | Erickson, Jr. et al. |
| 6,992,237 B1 | 1/2006 | Habben et al. |
| 7,022,896 B1 | 4/2006 | Weeks et al. |
| 7,026,528 B2 | 4/2006 | Cheng et al. |
| 7,056,704 B2 | 6/2006 | Tuschl et al. |
| 7,078,196 B2 | 7/2006 | Tuschl et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,855,323 B2 | 12/2010 | Huang et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,097,712 B2 | 1/2012 | Paldi et al. |
| 8,143,480 B2 | 3/2012 | Axtell et al. |
| 8,158,414 B2 | 4/2012 | Rommens et al. |
| 8,507,457 B2 | 8/2013 | Paldi et al. |
| 8,548,778 B1 | 10/2013 | Hart et al. |
| 8,554,490 B2 | 10/2013 | Tang et al. |
| 8,598,332 B1 | 12/2013 | Waterhouse et al. |
| 9,006,414 B2 | 4/2015 | Huang et al. |
| 9,121,022 B2 | 9/2015 | Sammons et al. |
| 9,422,557 B2 | 8/2016 | Ader |
| 9,445,603 B2 | 9/2016 | Baum et al. |
| 10,100,306 B2 | 10/2018 | Inberg et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0086356 A1 | 7/2002 | Tuschl et al. |
| 2002/0114784 A1 | 8/2002 | Li et al. |
| 2002/0123476 A1 | 9/2002 | Emanuele et al. |
| 2003/0017068 A1 | 1/2003 | Larrain et al. |
| 2003/0044443 A1 | 3/2003 | Erickson, Jr. et al. |
| 2003/0092651 A1 | 5/2003 | Norris et al. |
| 2003/0096980 A1 | 5/2003 | Froehler et al. |
| 2003/0140371 A1 | 7/2003 | Stevens et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0180945 A1 | 9/2003 | Wang et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2004/0259247 A1 | 12/2004 | Tuschl et al. |
| 2005/0005319 A1 | 1/2005 | della-Cioppa et al. |
| 2005/0044591 A1 | 2/2005 | Yao et al. |
| 2005/0080032 A1 | 4/2005 | Gross et al. |
| 2005/0095199 A1* | 5/2005 | Whyard ............ A01K 67/0337 424/9.2 |
| 2005/0215435 A1 | 9/2005 | Menges et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011448 A1 | 1/2007 | Chhabra et al. |
| 2007/0011775 A1 | 1/2007 | Allen et al. |
| 2007/0021360 A1 | 1/2007 | Nyce et al. |
| 2007/0026765 A1* | 2/2007 | Renn ................ A01K 51/00 449/2 |
| 2007/0050860 A1 | 3/2007 | Andersen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0219151 A1 | 9/2007 | Satishchandran et al. |
| 2007/0232188 A1 | 10/2007 | Probasco |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0194512 A1 | 8/2008 | John et al. |
| 2008/0214443 A1 | 9/2008 | Baum et al. |
| 2008/0261303 A1 | 10/2008 | Kreutzer et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |

(56) References Cited

U.S. PATENT DOCUMENTS

| | | |
|---|---|---|
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0053231 A1 | 3/2012 | Paldi et al. |
| 2012/0107355 A1 | 5/2012 | Harris et al. |
| 2012/0108497 A1 | 5/2012 | Paldi et al. |
| 2012/0128218 A1 | 5/2012 | Amyot et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2012/0297501 A1 | 11/2012 | Beghyn et al. |
| 2012/0316220 A1 | 12/2012 | Ward et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0058890 A1 | 3/2013 | Raemaekers et al. |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0232646 A1 | 9/2013 | Baum et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0289097 A1 | 10/2013 | Paldi et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2014/0371298 A1 | 12/2014 | Paldi et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |
| 2017/0037407 A1 | 2/2017 | Gleit-Kielmanowicz et al. |
| 2017/0088838 A1 | 3/2017 | Inberg et al. |
| 2017/0183683 A1 | 6/2017 | Zheng et al. |
| 2017/0260522 A1 | 9/2017 | Zheng et al. |

FOREIGN PATENT DOCUMENTS

| | | |
|---|---|---|
| CA | 2806295 A1 | 2/2011 |
| CN | 1505504 A | 6/2004 |
| CN | 101139607 A | 3/2008 |
| CN | 101279950 A | 10/2008 |
| CN | 101279951 A | 10/2008 |
| CN | 101914540 A | 12/2010 |
| CN | 102822350 A | 12/2012 |
| CN | 105849266 A | 8/2016 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 375 408 A1 | 6/1990 |
| EP | 0 804 600 A1 | 11/1997 |
| EP | 1 157 991 A2 | 11/2001 |
| EP | 1 238 586 A1 | 9/2002 |
| EP | 1 416 049 A1 | 5/2004 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| EP | 2 703 489 A1 | 3/2014 |
| EP | 2 703 490 A1 | 3/2014 |
| EP | 2 706 114 A1 | 3/2014 |
| EP | 3 066 200 A1 | 9/2016 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |

(56) References Cited

FOREIGN PATENT DOCUMENTS

| | | |
|---|---|---|
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |
| JP | 2009137851 A | 6/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/47193 | 12/1997 |
| WO | WO 97/49816 A1 | 12/1997 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/04176 A1 | 1/2000 |
| WO | WO 00/32757 A2 | 6/2000 |
| WO | WO 00/034035 A2 | 6/2000 |
| WO | WO 00/044914 A1 | 8/2000 |
| WO | WO 01/07601 A2 | 2/2001 |
| WO | WO 01/34815 A1 | 5/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO-2005110068 A2 * | 11/2005 ............ A01N 63/02 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/074976 A1 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO-2007074976 A1 * | 7/2007 ........... A23K 20/111 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |

(56) References Cited

FOREIGN PATENT DOCUMENTS

| | | |
|---|---|---|
| WO | WO 2009/090402 A2 | 7/2009 |
| WO | WO 2009/091862 A2 | 7/2009 |
| WO | WO 2009/091863 A1 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/128465 A1 | 11/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/021171 A1 | 2/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/001336 A2 | 1/2015 |
| WO | WO 2015/010026 A2 | 1/2015 |
| WO | WO 2016/018887 A1 | 2/2016 |

OTHER PUBLICATIONS

Advisory Action dated Feb. 22, 2013, in U.S. Appl. No. 13/332,430.
Agricultural Chemical Usage 2006 Vegetables Summary, Agricultural Statistics Herewith Board, NASS, USDA, pp. 1-372 (2007).
Agrios, Plant Pathology (Second Edition), 2:466-470 (1978).
Akiyoshi et al., "Genomic Survey of the Non-Cultivatable Opportunistic Human Pathogen, Enterocytozoon Bieneusi," PLoS Pathogens, 5(1):e1000261: Jan. 1-10, 2009.
Amarzguioui et al., "An algorithm for selection of functional siRNA sequences," Biochemical and Biophysical Research Communications, 316:1050-1058 (2004).
Amdam et al., "Disruption of vitellogenin gene function in adult honeybees by intra-abdominal injection of double-stranded RNA," BMC Biotechnology, 3(1):1-8 (2003).
Amdam et al., "The Hive Bee to Forager Transition in Honeybee Colonies: The Double Repressor Hypothesis," Journal of Theoretical Biology, 223:451-464 (2003).
Amdam et al., "Altered Physiology in Worker Honey Bees (*Hymenoptera: apidae*) Infested with the Mite *Varroa Destructor* (*Acari: varrodae*): A Factor in Colony Loss During Overwintering," Journal of Economic Entomology, 97(3):741-747 (2004).
An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).
Andersen et al., "Delivery of siRNA from lyophilized polymeric surfaces," Biomaterials, 29:506-512 (2008).
Anonymous, "Agronomy Facts 37: Adjuvants for enhancing herbicide performance," n.p., 1-8, (Jan. 26, 2000), Web, (Jan. 21, 2014).
Aoki et al., "In Vivo Transfer Efficiency of Antisense Oligonucleotides into the Myocardium Using HVJ—Liposome Method," Biochem Biophys Res Commun, 231:540-545 (1997).
Applicant-Initiated Interview Summary dated Mar. 5, 2013 in U.S. Appl. No. 13/332,430.
Aronstein et al., "SID-I is Implicated in Systemic Gene Silencing in the Honey Bee," Journal of Agricultural Research and Bee World, 45(1):20-24 (2006).
Arpaia et al., "Production of transgenic eggplant (*Solanum melongena* L.) resistant to Colorado Potato Beetle (*Leptinotarsa decemlineata* Say)," Theor. Appl. Genet., 95:329-334 (1997).
Artymovich, "Using RNA interference to increase crop yield and decrease pest damage," MMG 445 Basic Biotech., 5(1):7-12 (2009).
Ascencio-Ibanez et al., "DNA abrasion onto plants is an effective method for geminivirus infection and virus-induced gene silencing," Journal of Virological Methods, 142:198-203 (2007).
Axtell et al., "A Two-Hit Trigger for siRNA Biogenesis in Plants," Cell, 127:565-577 (2006).
Bachman et al., "Characterization of the spectrum of insecticidal activity of a double-stranded RNA with targeted activity against Western Corn Rootworm (*Diabrotica virgifera virgifera LeConte*)," Transgenic Res., pp. 1-16 (2013).
Bart et al., "A novel system for gene silencing using siRNAs in rice leaf and stem-derived protoplasts," Plant Methods, 2(13):1-9 (2006).
Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Baum et al., "Control of coleopteran insect pests through RNA interference," Nature Biotechnology, 25(11):1322-1326 (2007).
Baum et al., "Progress Towards RNAi-Mediated Insect Pest Management," Advances in Insect Physiology, 47:249-295 (2014).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bhargava et al., "Long double-stranded RNA-mediated RNA interference as a tool to achieve site-specific silencing of hypothalamic neuropeptides," Brain Research Protocols, 13:115-125 (2004).
Bhatia et al., "Aphid resistance in Brassica crops: Challenges, biotechnological progress and emerging possibilities," Biotechnology Advances 29:879-955 (2011).
Boletta et al., "High Efficient Non-Viral Gene Delivery to the Rat Kidney by Novel Polycationic Vectors," J. Am Soc. Nephrol., 7:1728 (1996).

(56) References Cited

OTHER PUBLICATIONS

Bolognesi et al., "Characterizing the Mechanism of Action of Double-Stranded RNA Activity against Western Corn Rootworm(*Diabrotica virgifera virgifera* LeConte)," PLoS ONE, 7(10):e47534 (2012).
Breaker et al., "A DNA enzyme with Mg2+-dependent RNA phosphoesterase activity," Chemistry and Biology, 2:655-660 (1995).
Brodersen et al., "The diversity of RNA silencing pathways in plants," Trends in Genetics, 22(5):268-280 (2006).
Burri et al., "Microsporidian Mitosomes Retain Elements of the General Mitochondrial Targeting System," PNAS USA, 103(43):15916-15920 (2006).
Busch et al., "RNAi for discovery of novel crop protection products," Pflanzenschutz-Nachrichten Bayer, 58(1):34-50 (2005).
Campbell et al., "Gene-knockdown in the honey bee mite *Varroa destructor* by a non-invasive approach: studies on a glutathione S-transferase," Parasites & Vectors, 3(1):73, pp. 1-10 (2010).
Carthew, "Gene silencing by double-stranded RNA," Curr Opin Cell Biol., 13(2):244-248 (2001).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chang et al., "Dual-target gene silencing by using long, sythetic siRNA duplexes without triggering antiviral responses," Molecules and Cells, 27(6)689-695 (2009).
Chang et al., "Cellular Internalization of Fluorescent Proteins Via Arginine-rich Intracellular Delivery Peptide in Plant Cells," Plant Cell Physiol., 46(3):482-488 (2005).
Chawla-Sarkar et al., "Downregulation of Bcl-2, FLIP or IAPs (XIAP and Survivin) by siRNAs Sensitizes Resistant Melanoma Cells to Apo2L/TRAIL-Induced Apoptosis," Cell Death and Differentiation, 11:915-923 (2004).
Chen et al., "Exploring MicroRNA-Like Small RNAs in the Filamentous Fungus Fusarium oxysporum," PLOS One, 9(8):e104956:1-10 (2014).
Chen et al., High Throughput Genome-Wide Survey of Small RNAs from the Parasitic Protists Giardia Intestinalis and Triehomonas Vaginalis,: Genome, Biology and Evolution, pp. 165-175 (Jul. 6, 2009).
Chen et al., "Nosema Ceranae is a Long-Present and Wide-Spread Microsporidian Infection of the European Honey Bee (*Apis mellifera*) in the United States," Journal of Invertebrate Pathology, 97(2):186-188 (2008).
Christiaens et al., "The challenge of RNAi-mediated control of hemipterans," Current Opinion in Insect Science, 6:15-21 (2014).
CN101914540 Patent Disclosure, "Introduction of RNA into plant by interference," (2010).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Communication pursuant to Article 94(3) EPC dated Feb. 5, 2015, in European Patent Application No. 13156183.9.
Communication pursuant to Article 94(3) EPC dated Sep. 4, 2015, in European Patent Application No. 13156183.9.
Communication pursuant to Article 94(3) EPC dated Jun. 8, 2015, in European Patent Application No. 13156185.4.
Communication pursuant to Article 94(3) EPC dated May 29, 2015, in European Patent Application No. 13156185.4.
Communication pursuant to Article 94(3) EPC dated Sep. 1, 2015, in European Patent Application No. 10779855.5.
Communication pursuant to Article 94(3) EPC dated Oct. 8, 2013, in European Patent Application No. 10719620.6.
Communication pursuant to Article 94(3) EPC dated Feb. 6, 2015, in European Patent Application No. 10719620.6.
Communication pursuant to Article 94(3) EPC dated Jul. 12, 2013, in European Patent Application No. 08847971.2.
Communication pursuant to Article 94(3) EPC dated Feb. 17, 2011, in European Patent Application No. 08847971.2.
Communication pursuant to Article 94(3) EPC dated Feb. 17, 2014, in European Patent Application No. 08847971.2.
Communication pursuant to Article 94(3) EPC dated Jun. 29, 2012, in European Patent Application No. 08847971.2.
Concise Descriptions of Relevance filed by a third party on Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cooney et al., "Site-Specific Oligonucleotide Binding Represses Transcription of the Human c-myc Gene in Vitro," Science ,241:456-459 (1988).
Cornman et al., "Genomic Analyses of the Microsporidian Nosema Ceranae, An Emergent Pathogen of Honey Bees," PLoS Pathogens, 5(6):e1000466: Jun. 1-14, 2009.
COST Action FA0806 progress report "Plant virus control employing RNA-based vaccines: A novel non-transgenic strategy" (2010).
Cox-Foster et al., "A Metagenomic Survey of Microbes in Honey Bee Colony Collapse Disorder," Science, 318(5848):283-287 (2007).
Cox-Foster et al., "Israel Acute Paralysis Virus of Bees Isolate IAPV.OP2 RNA-Dependent RNA Polymerase and Structural Polyprotein Genes, Partial CDs," Database EMBL [Online], retrieved from EBI, Database Accession No. EU122366, Nov. 15, 2007.
Cox-Foster et al., "Saving the Honeybee. The Mysterious Ailment Called Colony Collapse Disorder has Wiped out Large Numbers of the Bees that Pollinate a Third of Our Crops," Scientific American, p. 40-47 (2009).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* is Required for Posttranscriptional Gene Silencing Mediated by a Transgene but Not by a Virus," Cell, 101:543-553 (2000).
Davidson et al., "Engineering regulatory RNAs," TRENDS in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
Decision on Rejection dated Aug. 3, 2015 from the State Intellectual Property Office of the People's Republic of China, issued in Chinese Application No. 201080056585.9, with translation.
De Framond, "MINI-Ti: A New Vector Strategy for Plant Genetic Engineering," Nature Biotechnology, 1:262-269 (1983).
De La Fuente et al., "RNA Interference for the Study and Genetic Manipulation of Ticks," Trends in Parasitology, 23(9):427-433 (2007), abstract.
Desai et al., "Reduction in deformed wing virus infection in larval and adult honey bees (*Apis mellifera* L.) by double-stranded RNA ingestion," Insect Molecular Biology, 21(4):446-455 (2012).
Di Prisco et al. "Varroa Destructor is an Effective Vector of Israeli Acute Paralysis Virus in the Honeybee, *Apis mellifera*", Journal of General Virology, 92: 151-155 (2011).
Di Stilio et al., "Virus-Induced Gene Silencing as a Tool for Comparative Functional Studies in Thalictrum," PLoS One, 5(8):e12064 (2010).
Diallo et al., "Long Endogenous dsRNAs can Induce Complete Gene Silencing in Mammalian Cells and Primary Cultures," Oligonucleotides, 13:381-392 (2003).

(56) References Cited

OTHER PUBLICATIONS

Dietemann et al., "Varroa destructor: research avenues towards sustainable control," Journal of Apicultural Research, 51(1):125-132 (2012).
Dietzl et al., "A genome-wide transgenic RNAi library for conditional gene inactivation Drosophila," Nature, 448:151-157 (2007).
Du et al., "A systematic analysis of the silencing effects of an active siRNA at all single-nucleotide mismatched target sites," Nucleic Acids Research, 33(5):1671-1677 (2005).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Ellington et al., "In vitro selection of RNA molecules that bind specific ligands," Nature, 346:818-822 (1990).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report and the European Search Opinion dated Feb. 3, 2014, in European Patent Application No. 13156180.5.
European Search Report dated Feb. 3, 2014, in European Patent Application No. 13156180.4.
European Search Report dated Feb. 6, 2014, in European Patent Application No. 13156183.9.
European Search Report dated Jun. 29, 2018, in European Patent Application No. 18157745.3.
European Search Report dated Sep. 7, 2017, in European Patent Application No. 17152830.0.
European Search Report dated Feb. 3, 2014, in European Patent Application No. 13156185.4.
Examination Report dated Mar. 1, 2018, in Australian Patent Application No. 2013264742.
Examination Report dated Oct. 31, 2013, in Mexican Patent Application No. MX/a/2012/004378, with English summary.
Examination Report dated May 12, 2014, in Mexican Patent Application No. MX/a/2012/004378, with translation.
Examination Report dated Jan. 30, 2015, in Mexican Patent Application No. MX/a/2012/004378, with translation.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated May 23, 2018, in European Patent Application No. 15826865.6.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 29, 2016, in European Patent Application No. 14778840.0.
Extended European Search Report dated Apr. 13, 2018, in European Patent Application No. 15812530.0.
Extended European Search Report dated Mar. 15, 2018, in European Patent Application No. 17181861.0.
Fairbairn et al. "Host-Delivered RNAi: An Effective Strategy to Silence Genes in Plant Parasitic Nematodes," Planta, 226(6):1525-1533 (2007) Abstract.
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Fiala et al., "Reversible Downregulation of Protein Kinase A during Olfactory Learning Using Antisense Technique Impairs Long-Term Memory Formation in the Honeybee, *Apis mellifera*," J. Neuroscience, 19:10125-10134 (1999).
Final Office Action dated Apr. 7, 2016, in U.S. Appl. No. 13/619,980.
Final Office Action dated Aug. 1, 2013, in U.S. Appl. No. 13/318,636.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 18, 2011, in U.S. Appl. No. 12/222,949.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 15, 2012, in U.S. Appl. No. 13/332,430.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 28, 2015, in U.S. Appl. No. 13/932,051.
Final Office Action dated Sep. 9, 2016, in U.S. Appl. No. 13/612,954.
Final Office Action dated Sep. 9, 2016, in U.S. Appl. No. 14/603,347.
Final Office Action dated Sep. 9, 2016, in U.S. Appl. No. 14/608,951.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Foley et al., "The distribution of *Aspergillus* spp. Opportunistic parasites in hives and their pathogenicity to honey bees," Veterinary Microbiology, 169:203-210 (2014).
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).

(56) References Cited

OTHER PUBLICATIONS

Fukunaga et al., "dsRNA with 5' overhangs v contributes to endogenous and antiviral RNA silencing pathways in plants," The EMBO Journal, 28(5):545-555 (2009).
Further Examination Report dated May 16, 2014, in New Zealand Patent Application No. 601784.
Gallie et al., "Identification of the motifs within the tobacco mosaic virus 5'-leader responsible for enhancing translation," Nucleic Acids Res., 20(17):4631-4638 (1992).
Gan et al., "Bacterially expressed dsRNA protects maize against SCMV infection," Plant Cell Rep, 29(11):1261-1268 (2010).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1-9:e1003035 (2012).
Gaskin et al., "Novel organosillicone adjuvants to reduce agrochemical spray volumes on row crops," New Zealand Plant Protection, 53:350-354 (2000).
Gill et al. "Stripped-Down DNA Repair in a High Reduced Parasite," BMC Molecular Biology, 8(24): 1-14 (2007).
Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).
Gong et al., "Silencing of Rieske iron—sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Hagio, "Chapter 25: Direct Gene Transfer into Plant Mature Seeds via Electroporation After Vacuum Treatment," Electroporation and Sonoporation in Developmental Biology, p. 285-293 (2009).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature, 481:244-251 (2002).
Henderson et al., "U.S. National Bee Colony Loss Survey, www.beesurvey.com, Preliminary Findings With Respect to Colony Collapse Disorder (CCD)," Bee Alert Technology, Inc. (2007).
Heneberg et al., "Assemblage of filamentous fungi associated with aculeate hymenopteran brood in reed galls," Journal of Invertebrate Pathology, 133:95-106 (2016).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high-and low-molecular-weight RNA from silenced sunflower (*Helianthus annuus* L.) plants triggers post-transcriptional gene silencing in non-silenced plants," Plant Biotechnology Journal, 3:81-89 (2005).
Himber et al., "Transitivity-dependant and-independent cell-to-cell movement of RNA silencing," The EMBO Journal, 22(17):4523-4533 (2003).
Hsieh et al., "A library of siRNA duplexes targeting the phosphoinositide 3-kinase pathway: determinants of gene silencing for use in cell-based screens," Nucleic Acids Res., 32(3):893-901 (2004).
Hu et al., "High efficiency transport of quantum dots into plant roots with the aid of silwet L-77," Plant Physiology and Biochemistry, 48:703-709 (2010).
Huang et al., "Engineering broad root-know resistance in transgenic plants by RNAi silencing of a conserved and essential root-knot nematode parasitism gene," Proc. Natl. Acad. Sci. USA, 103(39):14302-14306 (2006).
Huesken et al., "Design of a genome-wide siRNA library using an artificial neural network," Nature Biotechnology, 23(8): 995-1001 (2005).
Hunter et al., "Large-Scale Field Application of RNAi Technology Reducing Israeli Acute Paralysis Virus Disease in Honey Bees (*Apis mellifera, Hymenoptera: apidae*)," PLoS Pathogens, 6(12):e1001160-1-e1 001160-10 (2010).
Hunter et al., "RNA Interference Strategy to suppress Psyllids & Leafhoppers," International Plant and Animal Genome XIX, 15-19 (2011).
Huvenne et al., "Mechanisms of dsRNA uptake in insects and potential of RNAi for pest control: A review," Journal of Insect Physiology, 56:227-235 (2010).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Apr. 26, 2012, International Application No. PCT/IL2010/000844.
International Preliminary Report on Patentability dated Feb. 1, 2010, in International Application No. PCT/IL2008/001440.
International Preliminary Report on Patentability dated Mar. 1, 2012, in International Application No. PCT/IB2010/053776.
International Preliminary Report on Patentability dated Feb. 21, 2012, in International Application No. PCT/IB2010/053776.
International Preliminary Report on Patentability dated Nov. 17, 2011, in International Application No. PCT/IB2010/051980.
International Preliminary Report on Patentability dated Oct. 23, 2014, in International Application No. PCT/IL2013/050321.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 13, 2009, in International Application No. PCT/IL2008/001440.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Dec. 31, 2015, in International Application No. PCT/US2015/042415.
International Search Report and Written Opinion dated Feb. 23, 2015, in International Application No. PCT/US2014/063832.
International Search Report and Written Opinion dated Feb. 24, 2011, in International Application No. PCT/IL2010/000844.

(56) References Cited

OTHER PUBLICATIONS

International Search Report and Written Opinion dated Jul. 19, 2010, in International Application No. PCT/IB2010/051980.
International Search Report and Written Opinion dated Jul. 8, 2015, in International Application No. PCT/US2015/011408.
International Search Report and Written Opinion dated Mar. 26, 2015, in International Application No. PCT/US2014/069535.
International Search Report and Written Opinion dated May 23, 2017, in International Application No. PCT/US2017/015061.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report and Written Opinion dated Nov. 30, 2010, in International Application No. PCT/IB2010/053776.
International Search Report and Written Opinion dated Oct. 1, 2015 in International Application No. PCT/US2015/022985.
International Search Report and Written Opinion dated Oct. 17, 2016, in International Application No. PCT/US2016/030579.
International Search Report and Written Opinion dated Oct. 28, 2013, in International Application No. PCT/IL2013/050321.
International Search Report dated Mar. 12, 2013, in International Application No. PCT/US2012/054789.
Invitation to Pay Additional Fees dated Jul. 24, 2013, in International Application No. PCT/IL2013/050321.
Invitation to Pay Additional Fees dated May 13, 2009, in International Application No. PCT/IL2008/001440.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Jarvis et al, "An *Arabidopsis* mutant defective in the plastid general protein import apparatus," Science, 282:100-103 (1998).
Ji et al., "Regulation of small RNA stability: methylation and beyond," Cell Research, 22:624-636 (2012).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jones-Rhoades et al., "MicroRNAs and Their Regulatory Roles in Plants," Annu. Rev. Plant Biol., 57:19-53 (2006).
Kam et al., "Nanotube Molecular Transporters: Internalization of Carbon Nanotube-Protein Conjugates into Mammalian Cells," J. Am. Chem. Soc., 126(22):6850-6851 (2004).
Katinka et al., "Genome Sequence and Gene Compaction of the Eukaryote Parasite Encephalitozoon Cuniculi," Nature, 414(6862):450-453, abstract (2001).
Katoh et al., "Specific residues at every third position of siRNA shape its efficient RNAi activity," Nucleic Acids Res., 35(4): e27 (2007).
Khodakovskaya et al., "Carbon Nanotubes are Able to Penetrate Plant Seed Coat and Dramatically Affect Seed Germination and Plant Growth," ACS Nano, 3(10):3221-3227 (2009).
Khovorova et al., "Rational siRNA design for RNA interference," Nature Biotechnol., 22 :326-330 (2004).
Kikkert et al., "Stable Transformation of Plant Cells by Particle Bombardment/Biolistics," Methods in Molecular Biology, 286:61-78 (2005).

Kim et al., "Optimization of Conditions for Transient Agrobacterium-Mediated Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Kondylis et al., "The Golgi apparatus: Lessons from *Drosophila*," FEBS Letters 583:3827-3838 (2009).
Kronenwett et al., "Oligodeoxyribonucleotide Uptake in Primary Human Hematopoietic Cells is Enhanced by Cationic Lipids and Depends on the Hematopoietic Cell Subset," Blood, 91(3):852-862 (1998).
Kumar et al., "Sequencing, De Novo Assembly and Annotation of the Colorado Potato Beetle, *Leptinotarsa decemlineata*, Transcriptome," PLOS One, 9(1):e86012:1-17 (2014).
Kusaba, "RNA interference in crop plants," Curr Opin Biotechnol, 15(2):139-143 (2004).
Lee et al., "A systematic RNAi screen identifies a critical role for mitochondria in C. elegans longevity." Nature Genetics, 33:40-48 (2003).
Lee et al., "Aptamer Database," Nucleic Acids Research, 32:D95-D100 (2004).
Li et al, "RNA interference in Nilaparvata lugens (Homoptera:Delphacidae) based on dsRNA ingestion," Pest Manag. Sci., 67:852-859 (2011).
Li et at., "Long dsRNA but not siRNA initiates RNAi in western corn rootworm larvae and adults," Journal of Applied Entomology, 139(6):432-445 (2015).
Liu et al., "Prevention of Chinese Sacbrood Virus Infection in Apis Cerana Using RNA Interference," Current Microbiology, 61(5):422-428 (2010).
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films," Bioelectrochemistiy, 70:301-307 (2007).
Liu et al., "DNAzyme-mediated recovery of small recombinant RNAs from a 5S rRNA-derived chimera expressed in *Escherichia coli*," BMC Biotechnology, 10:85 (2010).
Liu et al., "Effect of a Fluvalinate-Resistance-Associated Sodium Chennel Mutation From Varroa Mites on Cockroach Sodium Channel Sensitivity to Flucalinate, A Pyrethroid Insecticide," Insect Biochemistry and Molecular Biology, 36(11):885-889 (2006).
Liu, "Influence of Sugars on the Foliar Uptake of Bentazone and Glyphosate," New Zealand Plant Protection, 55:159-162 (2002).
Liu, "The Transformation of Nucleic Acid Degradants in Plants," China Organic Fertilizers, Agriculture Press, ISBN: 7-1091634 (with English translation), 1991.
Llave et al., "Endogenous and Silencing-Associated Small RNAs in Plants," The Plant Cell, 14:1605-1619 (2002).
Lu et al., "OligoWalk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
Luque et al., "Water Permeability of Isolated Cuticular Membranes: A Structural Analysis," Archives of Biochemistry and Biophysics, 317(2):417-422 (1995).
Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167-2170 (1990).
Maggi et al., "Resistance Phenomena to Amitraz From Population of the Ectoparasitic Mite Varroa Destructor of Argentina," Parasitology Research, 107(5):1189-1192 (2010).
Maher III et al., "Inhibition of DNA binding proteins by oligonucleotide-directed triple helix formation," Science, 245(4919):725-730 (1989).

(56) References Cited

OTHER PUBLICATIONS

Makkouk et al., "Virus Diseases of Peas, Beans, and Faba Bean in the Mediterranean region," Adv Virus Res, 84:367-402 (2012).
Malhotra et al., "Double-Stranded RNA-Mediated Gene Silencing of Cysteine Proteases (Falcipain-1 and -2) of Plasmodium Falciparum," Molecular Microbiology, 45(5):1245-1254 (2002).
Malone et al., "Effects of Transgene Products on Honey Bees (*Apis mellifera*) and Bumblebees (*Bombus* Sp.)," Apidologie 32(4):287-304 (2001).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Mao et al., "Silencing a cotton bollworm P450 monooxygenase gene by plant-mediated RNAi impairs larval tolerance of gossypol. ," Nat Biotechnol., 25(11):1307-13 (2007).
Maori et al., "Isolation and characterization of Israeli acute paralysis virus, a dicistrovirus affecting honeybees in Israel: evidence for diversity due to intra- and inter-species recombination," Journal of General Virology, 88:3428-3438 (2007).
Maori et al., "Israel Acute Paralysis Virus of Bees, Complete Genome", GenBank EMBL, EBIDbfetch, XP002533679, Accession No. EF219380, Nov. 21, 2007.
Maori et al., "Reciprocal sequence exchange between non-retro viruses and hosts leading to the appearance of new host phenotypes," Virology, 362(2):342-349 (2007).
Maori et al., "IAPV, a bee-affecting virus associated with Colony Collapse Disorder can be silenced by dsRNA ingestion," Insect Molecular Biology, 18(1):55-60 (2009).
Masoud et al., "Constitutive expression of an inducible β-1,3-glucanase in alfalfa reduces disease severity caused by the oomycete pathogen Phytophthora megasperma f. sp *Medicaginis*, but does not reduce disease severity of chitincontaining fungi," Transgenic Research, 5(5):313-323 (1996).
Matveeva et al., "Prediction of antisense oligonucleotide efficacy by in vitro methods," Nature Biotechnology, 16:1374-1375 (1998).
Mayack et al., "Energetic Stress in the Honeybee *Apis mellifera* from Nosema Ceranae Infection," Journal of Invertebrate Pathology, 100(3):185-188 (2009).
McGinnis, "RNAi for functional genomics in plants," Brief Funct Genomics, 9(2):111-7 (2010).
Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants are Mobile and Direct Epigenetic Modification Recipient Cells," Science, 328:872-875 (2010).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Moser et al., "Sequence-Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Mutti et al., "IRS and TOR Nutrient-Signaling Pathways Act Via Juvenile Hormone to Influence Honey Bee Caste Fate," Journal of Experimental Biology, 214(pt.23):3977-3984 (2011), abstract.
Nakayashiki et al. "Evolution and Diversification of RNA Silencing Proteins in Fungi," Journal of Molecular Evolution, 63(1):127-135 (2006).
Nielsen et al., "Sacbrood Virus Isolate T73/05A Polyprotein Gene, Partial CDs," Database EMBL [Online], retrieved from IBIS, Database Accession No. EF570887, May 12, 2007.
Non-Final Office Action dated Apr. 11, 2013, in U.S. Appl. No. 13/042,856.
Non-Final Office Action dated Apr. 15, 2014, in U.S. Appl. No. 13/446,557.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Feb. 5, 2014, in U.S. Appl. No. 13/446,557.
Non-Final Office Action dated Jan. 7, 2013, in U.S. Appl. No. 13/318,636.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 28, 2010, in U.S. Appl. No. 12/222,949.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated May 30, 2012, in U.S. Appl. No. 13/332,430.
Non-Final Office Action dated May 4, 2015, in U.S. Appl. No. 13/932,051.
Non-Final Office Action dated Nov. 21, 2012, in U.S. Appl. No. 13/318,636.
Non-Final Office Action dated Nov. 9, 2016, in U.S. Appl. No. 14/901,003.

(56) References Cited

OTHER PUBLICATIONS

Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 23, 2010, in U.S. Appl. No. 12/222,949.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Nowak et al., "A new and efficient method for inhibition of RNA viruses by DNA interference," The FEBS Journal, 276:4372-4380 (2009).
Nunes et al., "A non-invasive method for silencing gene transcription in honeybees maintained under natural conditions," Insect Biochemistry and Molecular Biology, 39:157-160 (2009).
Office Action dated Apr. 13, 2016, in Chinese Patent Application No. 201280053985.3.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2015, in New Zealand Patent Application No. 700791.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2017, in Chinese Patent Application No. 201480014392.5, and English translation of same.
Office Action dated Aug. 3, 2017, in European Patent Application No. 12 831 684.1.
Office Action dated Aug. 8, 2017, in Chilean Patent Application No. 201501874.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03849.
Office Action dated Dec. 15, 2016, in Ukrainian Patent Application No. a 2014 03852.
Office Action dated Dec. 27, 2016, in Ukrainian Patent Application No. a 2012 11548.
Office Action dated Dec. 5, 2017, in Japanese Patent Application No. 2016-502033.
Office Action dated Feb. 17, 2014, in Mexican Patent Application No. MX/a/2012/010479.
Office Action dated Feb. 21, 2018, in Mexican Patent Application No. MX/a/2015/012632 (with English translation).
Office Action dated Feb. 24, 2014, in Eurasian Patent Application No. 201201264.
Office Action dated Jul. 11, 2017, in Mexican Patent Application No. MX/a/2015/013118 (with English translation).
Office Action dated Jul. 18, 2016, in Indonesian Patent Application No. W00201203610.
Office Action dated Jul. 23, 2015, in Ukrainian Patent Application No. 201211548.
Office Action dated Jul. 3, 2017, in Mexican Patent Application No. MX/a/2015/012632, and English translation of same.
Office Action dated Jul. 6, 2017, in Mexican Patent Application No. MX/a/2015/013103, and English translation of same.
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated Mar. 8, 2018, in Chilean Patent Application No. 201403192, and English translation of same.
Office Action dated May 3, 2016, in Chilean Patent Application No. 201601057.
Office Action dated Nov. 15, 2016, in Mexican Patent Application No. MX/a/2014/003068, and English translation of same.
Office Action dated Sep. 5, 2016, in Ukrainian Patent Application No. a 2014 03846.
Office Action dated Sep. 6, 2017, in Chinese Patent Application No. 2014800154012, and English translation of same.
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Office Action dated Mar. 20, 2015, in Indian Patent Application No. 1150/MUMNP/2010.
Office Action dated Jan. 19, 2014, in Israeli Patent Application No. 205594, with translation.
Office Action dated Mar. 19, 2012, in Israeli Patent Application No. 205594, with translation.
Office Action dated Dec. 31, 2014, in Israeli Patent Application No. 205594, with translation.
Office Action dated Jan. 26, 2015, in Israeli Patent Application No. 219193, with translation.
Office Action dated Nov. 10, 2014, in European Patent Application No. 10779855.5.
Office Action dated Sep. 29, 2014, in European Patent Application No. 13156180.5.
Office Action dated Sep. 29, 2014, in European Patent Application No. 13156185.4.
Office Action dated Dec. 18, 2014, in Israeli Patent Application No. 216154.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
O'Riordan et al "Inhibitor of Apoptosis (IAP) Proteins in Eukaryotic Evolution and Development: A Model of Thematic Conservation," Developmental Cell, 15(4):497-508 (2008).
Ouellet et al., "Members of the Acetohydroxyacid Synthase Muligene Family of Brassica Napus Have Divergent Patterns of Expression," The Plant Journal, Blackwell Scientific Publications, Oxford, GB, 2(3):321-330 (1992).
Paddison et al., "Stable suppression of gene expression by RNAi in mammalian cells," Proc. Natl Acad. Sci. USA, 99(3):1443-1448 (2002).
Palacios et al., "Genetic Analysis of Israel Acute Paralysis Virus: Distinct Clusters are Circulating in the United States," Journal of Virology, 82(13):6209-6217 (2008).
Palacios et al., "Israel Acute Paralysis Virus of Bees Strain OZ6-Australia-2007, Complete Genome," Database EMBL [Online], retrieved from EBI, Database Accession No. EU436456, Jun. 19, 2008.
Palauqui et al., "Activation of systemic acquired silencing by localised introduction of DNA," Current Biology, 9:59-66 (1999).

(56) References Cited

OTHER PUBLICATIONS

Paldi et al. "Effective Gene Silencing in a Microsporidian Parasite Associated With Honeybee (*Apis mellifera*) Colony Declines," Applied and Environmental Microbiology, 760(17):5960-5964 (2010).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Dec. 6, 2017, in European Patent Application No. 17181861.0.
Partial Supplementary European Search Report dated Mar. 2, 2015, in European Patent Application No. 12 831 494.5.
Partial Supplementary European Search Report dated Jan. 11, 2018, in European Patent Application No. 15812530.0.
Patel et al., "The Making of A Queen: TOR Pathway is a Key Player in Diphemc Caste Development," PLoS ONE, 2(6):e509-1-e509-7, Jun. 2007.
Patent Examination Report No. 1 dated Nov. 6, 2014, in Australian Patent Application No. 2010244122.
Patent Examination Report No. 1 dated Oct. 23, 2013, in Australian Patent Application No. 2008325989.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).
Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Peyretaillade et al., "Microsporidian Encephalitozoon Cuniculi, A Unicellular Eukaryote With an Unusual Chromosomal Dispersion of Ribosomal Genes and a LSU rRNA Reduced to the Universal Core," Nucleic Acids Research 26(15):3513-3520 (1998).
Pitino et al., "Silencing of Aphid Genes by dsRNA Feeding from Plants," PLos ONE, 6:e25709 (2011).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).
Pratt et al., "Amaranthus rudis and A. tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Price et al. "RNAi-Mediated Crop Protection Against Insects," Trends in Biotechnology, XP022757296, 26(7):393-400 (2008).
Pridgeon et al., "Topically Applied AaeIAP1 Double-Stranded RNA Kills Female Adults of Aedes aegypti," J. Med. Entomol., 45(3):414-420 (2008).
Rajur et al., "Covalent Protein-Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).

Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Reither et al., "Specificity of DNA triple helix formation analyzed by a FRET assay," BMC Biochemistry, 3:27 (2002).
Requisition by the Examiner and Examination Search Report dated Mar. 19, 2015, in Canadian Patent Application No. 2,704,858.
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Robalino et al., "Double-Stranded RNA and Antiviral Immunity in Marine Shrimp: Inducible Host Mechanisms and Evidence for the Evolution of Viral Counter-Responses," Developmental & Comparative Immunology, 31: 539-547 (2007).
Roberts, "Fast-track applications: The potential for direct delivery of proteins and nucleic acids to plant cells for the discovery of gene function," Plant Methods, 1(12):1-3 (2005).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Ryabov et al., "Cell-to-Cell, but Not Long-Distance, Spread of RNA Silencing that is Induced in Individual Epidermal Cells," Journal of Virology, 78(6):3149-3154 (2004).
Salanenka et al., "Seedcoat Permeability: Uptake and Post-germination Transport of Applied Model Tracer Compounds," HortScience, 46(4):622-626 (2011).
Santoro et al., "A general purpose RNA-cleaving DNA enzyme," Proc. Natl. Acad. Sci. USA, 94:4262-4266 (1997).
Santosh et al., "RNA interference for the control of whiteflies (*Bemisia tabaci*) by oral route," Journal of Biosciences, 36(1):153-161 (2011).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Scott et al., "Towards the elements of successful insect RNAi," Journal of Insect Physiology, 59(12):1212-1221 (2013).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.

(56) References Cited

OTHER PUBLICATIONS

Second Office Action dated Mar. 4, 2016, in Chinese Patent Application No. 201280054820.8.
Second Office Action dated May 12, 2014, in Chinese Patent Application No. 201080056585.9, with English translation of same.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A systematic study to determine the extent of gene silencing in *Nicotiana benthamiana* and other *Solanaceae* species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shen et al., "The role of varroa mites in infections of Kashmir bee virus (KBV) and deformed wing virus (DWV) in honey bees," Virology, 342(1):141-149 (2005).
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al., "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Sindhu et al., "Effective and specific in planta RNAi in cyst nematodes: expression interference of four parasitism genes reduces parasitic success," J. Exp. Botany, 60:315-324 (2008).
Siomi et al., "On the Road to Reading the RNA-Interference Code," Nature, 457(7228):396-404 (2009).
Slamovits et al., "Genome Compaction and Stability in Microsporidian SiIntracellular Parasites," Current Biology, 14(10): 891-896 (2004).
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Soares et al., "Capillary feeding of specific dsRNA induces silencing of the isac gene in nymphal Ixodes scapularis ticks," Insect Mol. Biol., 14(4):443-452 (2005).
Song et al., "Herbicide," New Heterocyclic Pesticide, Chemical Industry Press, 354-356 (2011).
Standifer, L.N., "Honey bee Nutrition and Supplemental Feeding," Beekeeping in the United States Agriculture Handbook No. 335, pp. 39-45, Oct. 1980.
Standifer et al., "Supplemental Feeding of Honey Bee Colonies," Agriculture Information Bullentin No. 413, USDA, pp. 1-8 (1977).
Statement of Grounds and Particulars dated Sep. 1, 2017, in Australian Patent No. 2014262189.
Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—SILWET® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street, "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor et al., "Validation of Spermidine Synthase as a Drug Target in African Trypanosomes," Biochemical Journal, 409(2):563-569, Jan. 15, 2008.
Templeton et al., "Improved DNA: liposome complexes for increased systemic delivery and gene expression," Nature Biotechnology, 15:647-652 (1997).
Tenllado et al., "Crude extracts of bacterially expressed dsRNA can be used to protect plants against virus infection," BMC Biotechnology, 3(3):1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
Terenius et al., "RNA interference in Lepidoptera: an overview of successful and unsuccessful studies and implications for experimental design," Journal of Insect Physiology, 57(2):231-245 (2011).
Third Office Action dated Nov. 25, 2014, in Chinese Patent Application No. 201080056585.9, with English translation of same.
Third Party Submission filed Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).
Tian et al., "Developmental Control of a Lepidopteran Pest Spodoptera exigua by Ingestion of Bacteria Expressing dsRNA of a Non-Midgut Gene," PLoS ONE, 4:e6225, pp. 1-14 (2009).
Timmons et al., "Specific interference by ingested dsRNA," Nature, 395:854 (1998).
Tomari et al., "Perspective: machines for RNAi," Genes & Dev., 19:517-529 (2005).
Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," Bio/Technology, 6:1072-1074 (1988).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
Tsaousis et al., "A Novel Route for ATP Acquisition by the Remnant Mitochondria of Encephalitozoon Cuniculi," Nature 453(7194):May 22, 2008, Abstract.
Tsugawa et al., "Efficient transformation of rice protoplasts mediated by a synthetic polycationic amino polymer," Theor Appl Genet, 97:1019-1026 (1998).

(56) References Cited

OTHER PUBLICATIONS

Turina et al., "Tospoviruses in the Mediterranean Area," Advances in Virus Research, 84:403-437 (2012).
Turner et al., "RNA interference in the light brown apple moth, *Epiphyas postvittana* (Walker) induced by double-stranded RNA feeding," Insect Mol. Biol., 15(3):383-391 (2006).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Ullu et al., "RNA Interference in Protozoan Parasites," Cellular Microbiology, 6(6):509-519 (2004).
Ulrich et al., "Large scale RNAi screen in Tribolium reveals novel target genes for pest control and the proteasome as prime target," BMC genomics, 16(1):671 (2015).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Upadhyay et al., RNA interference for the control of whiteflies (*Bemisia tabaci*) by oral route, J. Biosci., 36(1):153-161 (2011).
Urayama et al., "Knock-down of OsDCL2 in Rice Negatively Affects Maintenance of the Endogenous dsRNA Virus, Oryza sativa Endornavims," Plant and Cell Physiology, 51(1):58-67 (2010).
Van Engelsdorp, "Colony Collapse Disorder: A Descriptive Study," PLos ONE, 4(8):e6481: 1-17 (2009).
van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Thermodynamic and Kinetic Characterization of Antisense Oligodeoxynucleotide Binding to a Structured mRNA," Biophysical Journal, 82:366-377 (2002).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).
Wang et al., "Tracking Anonymous Peer-to-Peer VoIP Calls on the Internet," ACM, CCS'05, Alexandria, VA, USA, pp. 1-11 (2005).
Wang et al., "Molecular Characterization of an Arachnid Sodium Channel Gene From the Varroa Mite (*Varroa destructor*)," Insect Biochemistry and Molecular Biology, 33(7): 733-739 (2003).

Wang et al., "Foliar uptake of pesticides—Present status and future challenge," ScienceDirect, 87:1-8 (2007).
Wang et al., "Principle and technology of genetic engineering in plants," in Plant genetic engineering principles and techniques, Beijing: Science Press, pp. 313-315 (1998).
Wang et al., "Silkworm Coatomers and Their Role in Tube Expansion of Posterior Silkgland," PLoS ONE 5(10): E133252 (2010).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Welch et al., "Expression of ribozymes in gene transfer systems to modulate target RNA levels," Curr Opin Biotechnol. 9(5):486-496 (1998).
Whitfield et al., "BB170006B20C05.5 Bee Brain Normalized/Subtracted Library, BB17 Apis Mellifera cDNA Clone BB170006B20C05 5', mRNA Sequence," Database EMBL [Online], retrieved IBIS, Database Accession No. BI503250, Aug. 30, 2001.
Whyard et al. "Ingested double-stranded RNAs can act as species-specific insecticides," Insect Biochem. Mol. Biol., 39(11):824-832 (2009).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot Noxious Weed Control Board (NWCB) of Washington State (2010) <www.nwcb.wa.gov/detail.asp?weed=46>.
Williams "Unique Physiology of Host-Parasite Interactions in Microsporidia Infections," Cellular Microbiology, 11(11):1551-1560 (2009).
Williams et al., "Genome Sequence Surveys of Brachiola Algerae and Edhazardia Aedis Reveal Micriosporidia With Low Gene Densities," BMC Genomics, 9(200):1-9 (2008).
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Written Opinion dated Apr. 7, 2016, in Singapore Patent Application No. 201206152-9.
Written Opinion dated Mar. 6, 2017, in Singaporean Patent Application No. 2012061529.
Written Opinion dated Sep. 1, 2014, in Singapore Patent Application No. 201206152-9.
Yadav et al., "Host-Generated Double Stranded RNA Induces RNAi in Plant-Parasitic Nematodes and Protects the Host From Infection," Molecular & Biochemical Parasitology, 148:219-222 (2006).
Yao et al., "Development of RNAi Methods for Peregrinus maidis, the Corn Planthopper," PLOS One, 8(8):1-11 (2013).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).

(56) References Cited

OTHER PUBLICATIONS

Zhao et al., "Phyllotreta striolata (Coleoptera: Chiysomelidae):Arginine kinase cloning and RNAi-based pest control," European Journal of Entomology, 105(5):815-822 (2008).
Zhao et al., "PsOr1, a potential target for RNA interference-based pest management," Insect Molecular Biology 20(1):97-104 (2011).
Zhou et al., "The Effects of Brood Comb Cell Size on the Reproductive Behavior of the Ectoparasitic Mite Varroa Destructor on Honey Bees," Chinese Journal of Entomology 43(1):89-93 (2006).
Zhu et al., "Ingested RNA interference for managing the populations of the Colorado potato beetle, *Leptinotarsa decemlineata*," Pest Manag Sci, 67:175-182 (2010).
Zotti et al., "RNAi technology for insect management and protection of beneficial insects from diseases: lessons, challenges and risk assessments," Neotropical Entomology, 44(3):197-213 (2015).
Alarcón-Reverte et al., "Resistance to ACCase-Inhibiting Herbicides in the Weed Lolium Multiflorum," Comm. Appl. Biol. Sci, 73(4):899:902 (2008).
Al-Kaff et al., "Plants rendered herbicide-susceptible by cauliflower mosaic virus-elicited suppression of a 35S promoter-regulated transgene," Nature Biotechnology, 18:995-999 (2000).
Ambrus et al., "The diverse roles of RNA helicases in RNAi," Cell Cycle, 8(21):3500-3505 (2009).
Andersson et al., "A novel selection system for potato transformation using a mutated AHAS gene," Plant Cell Rep, 22:261-267 (2003).
Araujo et al., "RNA interference of the salivary gland nitrophorin 2 in the triatomine bug Rhodnius prolixus (Hemiptera: Reduviidae) by dsRNA ingestion or injection," Insect Biochemistry and Molecular Biology, 36:683-693 (2006).
Aronstein et al., "Characterization of a honey bee Toll related receptor gene Am18w and its potential involvement in antimicrobial immune defense," Apidologie, 36:3-14 (2005).
Database Accession No. BT006855, "Homo sapiens calmodulin 3 (phosphorylase kinase, delta) mRNA" pp. 1-2 (2003).
Database Accession No. EF219380, "SV 1; linear; mRNA; STD; VRL; 9499 BO.," pp. 1-5 (2007).
Extended European Search Report dated Jan. 14, 2019, in European Patent Application No. 16789940.0.
Extended European Search Report dated Mar. 4, 2019, in European Patent Application No. 18 20 7017.7.
First Office Action dated Nov. 27, 2019, in Chinese Patent Application No. 2016800377700 (with English language translation).
GenBank BankIt, <https://www.ncbi.nlm.nih.gov/WebSub/?tool=genbank[Sep. 27, 2016 6:27:51 AM]> pp. 1-3 (2016).
Heath et al., "RNA Interference Technology to Control Pest Sea Lampreys—A Proof-of-Concept," PLOS One, 9(2):e88387:1-9 (2014).
International Search Report and Written Opinion dated Mar. 26, 2015, in International Application No. PCT/US2014/069353.
Sammataro et al., "Some Volatile Plant Oils as Potential Control Agents for Varroa Mites (Acari: Varroidae) in Honey Bee Colonies (Hymenoptera: Apidae)," American Bee Journal, 138(9):681-685 (1998).
Supplementary European Search Report dated Jan. 17, 2018, in European Patent Application No. 15773480.7.
Supplementary Partial European Search Report dated Jan. 11, 2018 in European Appln. 15826865.
Supplementary Partial European Search Report dated Oct. 16, 2017, in European Patent Application No. 15773480.7.
Yibrah et al., "Antisense RNA inhibition of uidA gene expression in transgenic plants: Evidence for interaction between first and second transformation events," Hereditas, 118:273-280 (1993).
Zhang, Chapter 10: New Characteristics of Pesticide Research & Development, p. 209 (2010).
Zrachya et al., "Production of siRNA targeted against TYLCV coat protein transcripts leads to silencing of its expression and resistance to the virus," Transgenic Res., 16:385-398 (2007).

\* cited by examiner

SEQUENCE LISTING

```
<160> NUMBER OF SEQ ID NOS: 148

<210> SEQ ID NO 1
<211> LENGTH: 371
<212> TYPE: DNA
<213> ORGANISM: Varroa destructor

<400> SEQUENCE: 1
gttagccgtc tgaagcaatg cttgactgta cagggtccga atataaaact tcatacattc      60
aaaatcacgt atcaggatta tgctaaacat cgcaccataa aaatcttcac taaagttatt     120
ttacgcttca ggatagtggt ccgttatgag tgttgcggta ttagtgcgtt tacaaatttg     180
```

```
ctaacgatat taacaagctt atttcactcg ttggcaggtt ttctagaacg cgaggtgagg       240
aaggataacc ttccgatgat gtcattcggc gacaatcctg aggcgcctca gcctcgggag       300
atgattgatc tagaagcaac ctttgagaaa ctcgaaaacg aactcaatga ggtagttttc       360
tgtgttgaaa t                                                            371

<210> SEQ ID NO 2
<211> LENGTH: 313
<212> TYPE: DNA
<213> ORGANISM: Varroa destructor

<400> SEQUENCE: 2
ctgtacaggg tccgaatata aaacttcata cattcaaaat cacgtatcag gattatgcta        60
aacatcgcac cataaaaatc ttcactaaag ttatttttacg cttcaggata gtggtccgtt      120
atgagtgttg cggtattagt gcgtttacag atttgctaac gttattaaca agctaatttc      180
actcgttggc aggttttcta gaacgcgagg tgaggaagga taaccttccg atgatgtcat      240
tcggcgacaa tcctgaggcg cctcagcctc gggagatgat tgatctagaa gcaacctttg      300
agaaactcga aaa                                                         313

<210> SEQ ID NO 3
<211> LENGTH: 304
<212> TYPE: DNA
<213> ORGANISM: Varroa destructor

<400> SEQUENCE: 3
ttcgagtttc tcaaaggttg cttctagatc aatcatctcc cgaggctgag gcgcctcagg        60
attgtcgccg aatgacatca tcggaaggtt atccttcctc acctcgcgtt ctagaaaacc      120
tgccaacgag tgaaattagc ttgttaataa cgttagcaaa tctgtaaacg cactaatacc      180
gcaacactca taacggacca ctatcctgaa gcgtaaaata actttagtga agattttttat     240 ggtgcgatgt ttagcataat cctgatacgt gattttgaat gtatgaagtt ttatattcgg      300
accc                                                                   304

<210> SEQ ID NO 4
<211> LENGTH: 242
<212> TYPE: DNA
<213> ORGANISM: Varroa destructor

<400> SEQUENCE: 4
caactcatta aaatgaaatc agtattccac atcatgaatc aattgaatat ggacgtcact        60
cagaagtgtc ttattgccga atgctggatt cctgatcgcg atgtagcaaa ggtacaagct      120
gccctgcgac gtggaacgga agcggctgga agcagcttcc cgtgtatcat taaccggttg      180
gaaacggacc aagctccacc gacgttctac agaacgaact cgtttactgc tggctttcaa      240
aa                                                                     242

<210> SEQ ID NO 5
<211> LENGTH: 213
<212> TYPE: DNA
<213> ORGANISM: Varroa destructor

<400> SEQUENCE: 5
caattcgtga ttcaattgaa tatggacgtc actcagaagt gtcttattgc cgaatgctgg        60
attcctgatc gcgatgtagc aaaggtacaa gctgccctgc gacgtggaac ggaagcggct      120
ggaagcagct tcccgtgtat cattaaccgg ttggaaacgg acaaagctcc accgacgttc      180
```

```
tacagaacga actcgtttac tgctggcttt caa                            213
```

<210> SEQ ID NO 6
<211> LENGTH: 201
<212> TYPE: DNA
<213> ORGANISM: Varroa destructor

<400> SEQUENCE: 6

```
caattgaata tggacgtcac tcagaagtgt cttattgccg aatgctggat tcctgatcgc   60
gatgtagcaa aggtacaagc tgccctgcga cgtggaacgg aagcggctgg aagcagcttc  120
ccgtgtatca ttaaccggtt ggaaacggac aaagctccac cgacgttcta cagaacgaac  180
tcgtttattg ctggctttca a                                            201
```

<210> SEQ ID NO 7
<211> LENGTH: 307
<212> TYPE: DNA
<213> ORGANISM: Varroa destructor

<400> SEQUENCE: 7

```
aatcacaatt ttctacatca tcttcttcat ctgcttggcg gcattctgga cggttatgct   60
ggtcatcttc tatcagacac tcgatgcctt ccagccaaag tggaccctgg acgctagtct  120
cattggcact gtaccgggat taggcttcag gccacgccca ccgctgtcta acatcgactc  180
aacactcatc tatttcaagg tatctaagcc gttagtgtat atgttatatt atagcgctct  240
ttgttatgtg gaaagacgcc agggcgcgta tctatatggt ggttttcata ccaaccgtgg  300
gaaccca                                                            307
```

<210> SEQ ID NO 8
<211> LENGTH: 290
<212> TYPE: DNA
<213> ORGANISM: Varroa destructor

<400> SEQUENCE: 8

```
ggttcccacg gttggtatga aaccaccat atagatacgc gccctggcgt ctttccacat    60
aacaaagagc gctataatat aacatataca ctaacggctt agataccttg aaatagatga  120
gtgttgagtc gatgttagac agcggtgggc gtggcctgaa gcctaatccc ggtacagtgc  180
caatgagact agcgtccagg gtccactttg gctggaaggc atcgagtgtc tgatagaaga  240
tgaccagcat aaccgtccag aatgccgcca agcagatgaa gaagatgatg              290
```

<210> SEQ ID NO 9
<211> LENGTH: 290
<212> TYPE: DNA
<213> ORGANISM: Varroa destructor

<400> SEQUENCE: 9

```
catcatcttc ttcatctgct tggcggcatt ctggacggtt atgctggtca tcttctatca   60
gacactcgat gccttccagc caaagtggac cctggacgct agtctcattg gcactgtacc  120
gggattaggc ttcaggccac gcccaccgct gtctaacatc gactcaacac tcatctattt  180
caaggtatct aagccgttag tgtatatgtt atattatagc gctctttgtt atgtggaaag  240
acgccagggc gcgtatctat atggtggttt tcataccaac cgtgggaacc              290
```

<210> SEQ ID NO 10
<211> LENGTH: 357
<212> TYPE: DNA

<213> ORGANISM: Varroa destructor

<400> SEQUENCE: 10

```
gaggtgacat ccgtgttcgc cgtgtacggc atcaaagtgg atccaagaca tctaagtctg    60
gtaggggact acatgacttt cgacggagct taccgcgcct tcaacagaat ccacatggca   120
aacaatgcat cgccactcca gcagatgagc tttgaaacga cgtgcacatt tatgaaaaac   180
gctgctttat ttggtacgaa atcccctaag acagatacga agacaatctt tgccatgcta   240
atagtgtttc tgtttttagt gcctggtacg atcattaatt acggcgttga aagtaactcc   300
aaacagcgac cctatatgtc ttcatacaag agacttagtt ctaggaaagc aaataca      357
```

<210> SEQ ID NO 11
<211> LENGTH: 325
<212> TYPE: DNA
<213> ORGANISM: Varroa destructor

<400> SEQUENCE: 11

```
tatgaagaca tagggtcg ctgtttggag ttactttcaa cgccgtaatt aatgatcgta     60
ccaggcacta aaacagaaa cactattagc atggcaaaga ttgtcttcgt atctgtctta   120
ggggatttcg taccaaataa agcagcgttt tcataaatg tgcacgtcgt ttcaaagctc   180
atctgctgga gtggcgatgc attgtttgcc atgtggattc tgttgaaggc gcggtaagct   240
ccgtcgaaag tcatgtagtc ccctaccaga cttagatgtc ttggatccac tttgatgccg   300
tacacggcga acacggatgt cacct                                         325
```

<210> SEQ ID NO 12
<211> LENGTH: 324
<212> TYPE: DNA
<213> ORGANISM: Varroa destructor

<400> SEQUENCE: 12

```
atgaagacat agggtcgc tgtttggagt tactttcaac gccgtaatta atgatcgtac     60
caggcactaa aaacagaaac actattagca tggcaaagat tgtcttcgta tctgtcttag   120
gggatttcgt accaaataaa gcagcgtttt cataaatgt gcacgtcgtt tcaaagctca   180
tctgctggag tggcgatgca ttgtttgcca tgtggattct gttgaaggcg cggtaagctc   240
cgtcgaaagt catgtagtcc cctaccagac ttagatgtct tggatccact ttgatgccgt   300
acacggcgaa cacggatgtc acct                                          324
```

<210> SEQ ID NO 13
<211> LENGTH: 406
<212> TYPE: DNA
<213> ORGANISM: Varroa destructor

<400> SEQUENCE: 13

```
cctgcgcatc catcagatga ttggaacgga ggaaaatgtc caagtagcat tcgtgggctc    60
gattgtcgag tgtcacaagc tcaaggtgtt tactcaggaa gaagcactga gattccttgc   120
ggcaaagatg aagcagcgga tgtttggacc acagaaagcg gaagacccct tgacaaggca   180
tgggaagccg tactttcatc cgtagtcaac catattcccg ttcaatcgcc tgactacaat   240
atgactgtcc gggcacacta tcttgcacta atggtgcgtc gcatcattca ggcgcgttat   300
gatcgccgct tcattgacga tcgcgactat tacggcaaca aacgaattga gcttccgggt   360
tcgatgatat cgctgctgtt tgaagacctg ttaaaaaagg ttaatg                  406
```

```
<210> SEQ ID NO 14
<211> LENGTH: 283
<212> TYPE: DNA
<213> ORGANISM: Varroa destructor

<400> SEQUENCE: 14
tcagatttca gatgattgga acggaggaaa atgtccaagt agcattcgtg ggctcgattg      60
tcgagtgtca caagctcaag gtgtttactc aggaagaagc actgagattc cttgcggcaa     120
agatgaagca gcggatgttt ggaccacaga agcggaaga cccccttgac aaggcatggg      180
aagccgtact ttcatccgta gtcaaccata ttcccgttca atcgcctgac tacaatatga     240
ccgtccgggc acactatctt gcactaatgg tgcgtcacat cat                        283

<210> SEQ ID NO 15
<211> LENGTH: 381
<212> TYPE: DNA
<213> ORGANISM: Varroa destructor

<400> SEQUENCE: 15
tcagatgatt ggaacggagg aaaatgtcca agtagcattc gtgggctcga ttgtcgagtg      60
tcacaagctc aaggtgttta ctcaggaaga agcactgaga ttccttgcgg caaagatgaa     120
gcagcggatg tttggaccac agaaagcgga agacccccct tgacaaggca tgggaagccgt   180 actttcatcc gtagtcaacc atattcccgt tcaatcgcct gactacaata tgaccgtccg     240
ggcacactat cttgcactaa tggtgcgtca catcattcag gcgcgttatg atcgccgctt     300
cattgacgat cgcgactatt acggcaacaa cgaattgag cttccgggtt cgatgatatc      360
gctgctgttt gaagacctgt t                                                381

<210> SEQ ID NO 16
<211> LENGTH: 446
<212> TYPE: DNA
<213> ORGANISM: Varroa destructor

<400> SEQUENCE: 16
aatcaattcg tctgcagatc tcaccgattt tctgatatcg ctgggagtcc aggatattcg      60
actactatgc ggagctgaat tcagcaaaac acacgtctac tatgtattcc acaacggtgt     120
tattaaaggc gtcgttgagg atcatcgcag gcttatcaac gagattcggc aatttcgtcg     180
gaagggatac ttgtcgcctt acttatcagt ttatccaaat catctacatc gctgtgtgta     240
tattgtaact gacggtggtc gtttctgcag gccgtttatc attgttgagg atggtcagcc     300
aaaagttacg cagaaacatt tggacgacct caaagccaat atataact tccaagactt       360 cctggacatg ggctttgtag agtttctcga tgtaaatgag gaaaacgacg cgcttatcgc     420
catttatgaa aaagatatca caatca                                           446

<210> SEQ ID NO 17
<211> LENGTH: 428
<212> TYPE: DNA
<213> ORGANISM: Varroa destructor

<400> SEQUENCE: 17
ttcataaatg gcgataagcg cgtcgttttc ctcatttaca tcgagaaact ctacaaagcc      60
catgtccagg aagtcttgga agttatatat attggctttg aggtcgtcca atgtttctg     120 cgtaactttt ggctgaccat cctcaacaat gataaacggc ctgcagaaac gaccaccgtc     180
agttacaata tacacacagc gatgtagatg atttggataa actgataagt aaggcgacaa     240
```

```
ctatcccttc cgacgaaatt gccgaatctc gttgataagc ctgcgatgat cctcaacgac    300
gcctttaata acaccgttgt ggaatacata gtagacgtgt gttttgctga attcagctcc    360
gcatagtagt cgaatatcct ggactcccag cgatatcaga aaatcggtga gatctgcaga    420
cgaattga                                                              428
```

```
<210> SEQ ID NO 18
<211> LENGTH: 426
<212> TYPE: DNA
<213> ORGANISM: Varroa destructor

<400> SEQUENCE: 18
tcaattcgtc tgcagatctc accgattttc tgatatcgct gggaatccag gatattcgac     60
tactatgcgg agctgaattc agcaaaaacac acgtctacta tgtattccac aacggtgtta   120
ttaaaggcgt cgttgaggat catcgcaggc ttatcaacga gattcggcaa tttcgtcgga   180
agggatactt gtcgccttac ttatcagttt atccaaatca tctacatcgc tgtgtgtata   240
ttgtaactga cggtggtcgt ttctgcaggc cgtttatcat tgttgaggat ggtcagccaa   300
aagttacgca gaaacatttg gacgacctca aagccaatat atataacttc caagacttcc   360
tggacatggg ctttgtagag tttctcgatg taaatgagga aaacgacgcg cttatcgcca   420
tttatg                                                               426
```

```
<210> SEQ ID NO 19
<211> LENGTH: 378
<212> TYPE: DNA
<213> ORGANISM: Varroa destructor

<400> SEQUENCE: 19
gttttgaaca aaatgagtgt tgagcgcgga tttaaggccg gtgtagtata taaaacagaa     60
acgatcaatt tgcgtaagtt atctggggat gtgggagtcc agacatcgtg cgttttggt    120 cgaaaggcag gagattctga gttacagaaa tttgtagatg ttgatggcct gccatacatc   180
ggcagcaggg tagtacaggg agatccggta tgtgcatata taaatttgac cacgggacaa   240
ctgaagactg taaggtatta ctcgaccgag ccagcaatcg tgcatgaagt gaaaattctt   300
ggtaatgatt ccggtacaga caccctccaa caaatccagt tgacgtatct tattgatcga   360
acgccaaatg atcggaga                                                  378
```

```
<210> SEQ ID NO 20
<211> LENGTH: 367
<212> TYPE: DNA
<213> ORGANISM: Varroa destructor

<400> SEQUENCE: 20
aatgagtgtt gagcgcggat ttaaggccgg tgtagtatat aaaacagaaa cgatcaattt     60
gcgtaagtta tctggggatg tgggagtcca gacatcgtgc gttttggtc gaaaggcagg    120 agattctgag ttacagaaat ttgtagatgt tgatggcctg ccatacatcg gcagcaggg   180 agtacaggga gatccggtat gtgcatatat aaatttgacc acgggacaac tgaagactgt   240
aaggtattac tcgaccgagc cagcaatcgt gcatgaagtg aaaattcttg gtaatgattc   300
cggtacagac accctccaac aaatccagtt gacgtatctt gttgatcgaa cgccaaatga   360
tcggaga                                                              367
```

```
<210> SEQ ID NO 21
<211> LENGTH: 366
```

```
<212> TYPE: DNA
<213> ORGANISM: Varroa destructor

<400> SEQUENCE: 21
aatgagtgtt gagcgcggat ttaaggccgg tgtagtatat aaaacagaaa cgatcaattt      60
gcgtaagtta tctggggatg tgggagtcca gacatcgtgc gttttggtc gaaaggcagg     120
agattctgag ttacagaaat ttgtagatgt tgatggcctg ccatacatcg gcagcagggt    180
agtacaggga gatccggtat gtgcatatat aaatttgacc acgggacaac tgaagactgt    240
aaggtattac tcgaccgagc cagcaatcgt gcatgaagtg aaaattcttg gtaatgattc    300
cggtacagac accctccaac aaatccagct gacgtatctt gttgatcgaa cgccaaatga    360
tcggag                                                               366

<210> SEQ ID NO 22
<211> LENGTH: 268
<212> TYPE: DNA
<213> ORGANISM: Varroa destructor

<400> SEQUENCE: 22
aatggtttct gctacctgtg aggatagtat gcgggatgct tgtattcgtt ttcttgcctc      60
gaaagtcaat ctcaaagcgc ttgacagtga cagagctt atgctcattg aagaggccgg      120
caaagtggca gccctcgtcg gtggagagga gtttgtgctg ctggttaagc tcctcaattc    180
attaaaggta gattgtacat tttggcgtct tctcgaacaa gttagaatct atttagcaaa    240
gtgccaatgt atcagcttcc aatacgca                                       268

<210> SEQ ID NO 23
<211> LENGTH: 263
<212> TYPE: DNA
<213> ORGANISM: Varroa destructor

<400> SEQUENCE: 23
attggaagct gatacattgg cactttgcta aatagattct aacttgttcg agaagacgcc      60
aaaatgtaca atctaccttt aatgaattga ggagcttaac cagcagcaca aactcctctc    120
caccgacgag ggctgccact ttgccggcct cttcaatgag cataagctct gtctctctgt    180
caagcgcttt gagattgact ttcgaggcaa gaaaacgaat acaagcatcc cgcatactat    240
cctcacaggt agcagaaacc att                                            263

<210> SEQ ID NO 24
<211> LENGTH: 263
<212> TYPE: DNA
<213> ORGANISM: Varroa destructor

<400> SEQUENCE: 24
attggaagct gatacattgg cactttgcta aatagattct aacttgttcg agaagacgcc      60
aaaatgtaca atctaccttt aatgaattga ggagcttaac cagcagcaca aactcctctc    120
caccgacgag ggctgccact ttgccggcct cttcaatgag cataagctct gtctctctgt    180
caagcgcttt gagattgact ttcgaggcaa gaaaacgaat acaagcatcc cgcatactat    240
cctcacaggt agcagaaacc att                                            263

<210> SEQ ID NO 25
<211> LENGTH: 279
<212> TYPE: DNA
<213> ORGANISM: Varroa destructor
```

<400> SEQUENCE: 25

```
gatcttgttg aagccggctt cttcttcctt ggcatgcacg attacacgaa atgcttccat        60
tgcgacggcg gtctgtgtaa ttgggagaca ggtgacgacc cctgggtaga gcatgcccgc       120
tggttccctg aatgtcaatt cgttcagcta agcaagggcg gagcattcat cgctgagtgc       180
caacaacgtc acgaaaaact agttaatggc gcggtagccc aggcagaact tcaggctttt       240
agtgaagtag aaccgggagg aacaggcagt gactcaaat                              279
```

<210> SEQ ID NO 26
<211> LENGTH: 263
<212> TYPE: DNA
<213> ORGANISM: Varroa destructor

<400> SEQUENCE: 26

```
agtcactgcc tgttcctccc ggttctactt cactaaaagc ctgaagttct gcctgggcta        60
ccgcgccatt aactagtttt tcgtgacgtt gttggcactc agcgatgaat gctccgccct       120
tgcttagctg aacgaattga cattcaggga accagcgggc atgctctacc caggggtcgt       180
cacctgtctc ccaattacac agaccgccgt cgcaatggaa gcatttcgtg taatcgtgca       240
tgccaaggaa gaagaagccg gct                                              263
```

<210> SEQ ID NO 27
<211> LENGTH: 299
<212> TYPE: DNA
<213> ORGANISM: Varroa destructor

<400> SEQUENCE: 27

```
ttccgcttca tttgagaact gagcttgaag aaataatgca gtcgcccgtc gtcaagttct        60
acctcgagaa aggtgtaccg aaacaagtga ttcgaatgac cgtaaaaaat atatgcttga       120
caacgagcgc ggtttccgtg atcttgacga aattacacac gtactcggac aggtgctcag       180
cttcggcaac aagaagactg cgcctgccaa tgaaaaggt aggtggatac cggatatttg        240
tcgggaattc aatgcagctg aacccgatga ggttgattca gaattggcat acaatagaa       299
```

<210> SEQ ID NO 28
<211> LENGTH: 284
<212> TYPE: DNA
<213> ORGANISM: Varroa destructor

<400> SEQUENCE: 28

```
ttccgcttca tttgagaact gagcttgaag aaataatgca gtcgcccgtc gtcaagttct        60
acctcgagaa aggtgtaccg aaacaagtga ttcgaatgac cgtaaaaaaa tatatgcttg       120
acaacgagcg cggtttccgt gatcttgacg aaattacaca cgtactcgga caggtgctca       180
gcttcggcaa caagaagact gcgcctgcca atgaaaaagg taggtggata ccggatattt       240
gtcgggaatt caatgcagct gaacccgatg aggttgattc agaa                        284
```

<210> SEQ ID NO 29
<211> LENGTH: 283
<212> TYPE: DNA
<213> ORGANISM: Varroa destructor

<400> SEQUENCE: 29

```
ttccgcttca tttgagaact gagcttgaag aaataatgca gtcgcccgtc gtcaagttct        60
acctcgagaa aggtgtaccg aaacaagtga ttcgaatgac cgtgaaaaaa tatatgcttg       120
acaacgagcg cggtttccgt gatcttgacg aaattacaca cgtactcgga caggtgctca       180
```

```
gcttcggcaa caagaagact gcgcctgcca atgaaaaagg taggtggata ccggatattt    240
gtcgggaatt caatgcagct gaacccgatg aggttgattc aga                      283
```

<210> SEQ ID NO 30
<211> LENGTH: 279
<212> TYPE: DNA
<213> ORGANISM: Varroa destructor

<400> SEQUENCE: 30

```
tggctaatta atagtaggcc gaagaacttt ttgagtggcc tcgatatgtc cgacgttgtg    60
gcttcgtggg aggttccttt ggttggccaa gcttaccgag tcgaattcga acacggaagt   120
gcaacgggta acgtgttgt gtacgttaat ggactcgagg tgttacgaaa acactggctt    180
tttaagcttg ttggcgagga agctttgac atattgggac ataagtgcat catttctatc    240
aaagccgtag gaggcttcag gttggtagca aactccagt                          279
```

<210> SEQ ID NO 31
<211> LENGTH: 277
<212> TYPE: DNA
<213> ORGANISM: Varroa destructor

<400> SEQUENCE: 31

```
tggctaatta atagtaggcc gaagaacttt ttgagtggcc tcgatatgtc cgacgttgtg    60
gcttcgtggg aggttccttt ggttggccaa gcttaccgag tcgaattcga acacggaagt   120
gcaacgggta acgtgttgt gtacgttaat ggactcgagg tgttacgaaa acactggctt    180
tttaagcttg ttggcgagga agctttgac atattgggac ataagtgcat catttctatc    240
aaagccgtag gaggcttcag gttggtagca aactcca                            277
```

<210> SEQ ID NO 32
<211> LENGTH: 277
<212> TYPE: DNA
<213> ORGANISM: Varroa destructor

<400> SEQUENCE: 32

```
tggagtttgc taccaacctg aagcctccta cggctttgat agaaatgatg cacttatgtc    60
ccaatatgtc aaagctttcc tcgccaacaa gcttaaaaag ccagtgtttt cgtaacacct   120
cgagtccatt aacgtacaca acacgtttac ccgttgcact tccgtgttcg aattcgactc    180
ggtaagcttg gccaaccaaa ggaacctccc acgaagccac aacgtcggac atatcgaggc   240
cactcaaaaa gttcttcggc ctactattaa ttagcca                            277
```

<210> SEQ ID NO 33
<211> LENGTH: 283
<212> TYPE: DNA
<213> ORGANISM: Varroa destructor

<400> SEQUENCE: 33

```
ggtcttgaca acacatgcta ccctcgaaca cgccgactgc gtcttcatga tggacaatga    60
ggccatctat cagatctgcc gtcggaacct tggagtcgag cgaccggcgt accagaatct   120
caaccgtctg atcagtcagg ccgtttcggc gattaccgct tctctacgtt tctccggagc   180
gctgaatgtt gatcttaacg agttccaaac taatttagtt ccatacccgc gaatccattt   240 tccccctcgtc acttacgctc cgatcatttc tgctgagaag gct                    283
```

<210> SEQ ID NO 34

```
<211> LENGTH: 279
<212> TYPE: DNA
<213> ORGANISM: Varroa destructor

<400> SEQUENCE: 34
ggtcttgaca acacatgcta ccctcgaaca cgccgactgc gtcttcatga tggacaatga      60
ggccatctat cagatctgcc gtcggaacct tggagtcgag cgaccggcgt accagaatct     120
caaccgtctg atcagtcagg ccgtttcggc gattaccgct tctctacgtt tctccggagc     180
gctgaatgtt gatcttaacg agttccaaac taatttagtt ccatacccgc gaatccattt     240
tccccccgtc acttacgctc cgatcatttc tgctgagaa                            279

<210> SEQ ID NO 35
<211> LENGTH: 277
<212> TYPE: DNA
<213> ORGANISM: Varroa destructor

<400> SEQUENCE: 35
ctcagcagaa atgatcggag cgtaagtgac gggggaaaa tggattcgcg ggtatggaac       60
taaattagtt tggaactcgt taagatcaac attcagcgct ccggagaaac gtagagaagc     120
ggtaatcgcc gaaacggcct gactgatcag acgttgaga ttctggtacg ccgtcgctc      180
gactccaagg ttccgacggc agatctgata gatggcctca ttgtccatca tgaagacgca    240
gtcggcgtgt tcgagggtag catgtgttgt caagacc                              277

<210> SEQ ID NO 36
<211> LENGTH: 332
<212> TYPE: DNA
<213> ORGANISM: Varroa destructor

<400> SEQUENCE: 36
caacgctgtg cttcacgtag actccacgtt cgaaaatgtc gactgcacgt ttatggttga      60
taatcaaaca ctcttcaagc tttgtcgaga ccggctaaag attaggagtc catcttatga    120
caacgcaaat gctgtcattt cccagggttt ttcgtcaatc atgaattcgg tggggctgga    180
tggatccttg aatgtggacc tcagcgagtt ccaaacaaat ctcgtccctt ttggaagatt    240
acattttacg atgatgagct acagtccatt cgttacatcc ggacaccgcg atctaagccg    300
tgagacgtcc gtcgtggaga ttactcgtga cc                                   332

<210> SEQ ID NO 37
<211> LENGTH: 330
<212> TYPE: DNA
<213> ORGANISM: Varroa destructor

<400> SEQUENCE: 37
caacgctgtg cttcacgtag actccacgtt cgaaaatgtc gactgcacgt ttatggttga      60
taatcaaaca ctcctcaagc tttgtcgaga ccggctaaag gttaggagtc catcttatga    120
caacgcaaat gctgtcattt cccagggttt ttcgtcaatc atgaattcgg tggggctgga    180
tggatccttg aatgtggacc tcagcgagtt ccaaacaagt ctcgtccctt ttggaagatt    240
acattttacg atgatgagct acagtccatt cgttacatcc ggacaccgcg atctaagccg    300
tgagacgtcc gtcgtggaga ttactcgtga                                      330

<210> SEQ ID NO 38
<211> LENGTH: 329
<212> TYPE: DNA
<213> ORGANISM: Varroa destructor
```

<400> SEQUENCE: 38

```
aacgctgtgc ttcacgtaga ctccacgttc gaaaatgtcg actgcacgtt tatggttgat      60
aatcaaacac tcctcaagct ttgtcgagac cggctaaagg ttaggagtcc atcttatgac     120
aacgcaaatg ctgtcatttc cagggtttt tcgtgaatca tgaattcggt ggggctggat     180
ggatccttga atgtggacct cagcgagttc caaacaagtc tcgtcccttt tggaagatta    240
cattttacga tgatgagcta cagtccattc gttacatccg gacaccgcga tctaagccgt    300
gagacgtccg tcgtggagat tactcgtga                                       329
```

<210> SEQ ID NO 39
<211> LENGTH: 415
<212> TYPE: DNA
<213> ORGANISM: Varroa destructor

<400> SEQUENCE: 39

```
tatggagaac atcgcacagg acttcggtaa aaagtgccga ttgggcttcg ccatctaccc      60
ggctccgcag gtttccactg ccgttgtcga accatacaac tcggttttga cgacacatgc    120
caccctcgaa cacgctgact gcgtattcat gatggataat gaggcgatct atcagatctg    180
tcgtcggaat cttggagttg aacgaccggc gtatcaaaat ctcaatcgac tgattagcca    240
ggccgtttcg cgataaccg cttctctacg ttttccgga gcgttgaatg ttgacctcaa      300
cgaatttcag acgaatctcg tccctaccc gcgaatccat ttcccgctcg tcacttatgc     360
tccgattatt tcggctgaga aggctcatca cgagcaacat aacgtactgg aaatc         415
```

<210> SEQ ID NO 40
<211> LENGTH: 412
<212> TYPE: DNA
<213> ORGANISM: Varroa destructor

<400> SEQUENCE: 40

```
atggagaaca tcgcacagga cttcggtaaa aagtgccgat tgggcttcgc catctacccg      60
gctccgcagg tttccactgc cgttgtcgaa ccatacaact cggttttgac gacacatgcc    120
accctcgaac acgctgactg cgtattcatg atggataatg aggcgatcta tcagatctgt    180
cgtcggaatc ttggagttga acgaccggcg tatcaaaatc tcaatcgact gattagccag    240
gccgtttcgg cgataaccgc ttctctacgt ttttccggag cgttgaatgt tgacctcaac    300
gaatttcaga cgaatctcgt cccctacccg cgaatccatt tcccgctcgt cacttatgct    360
ccgattattt cggctgagaa ggctcatcac gagcaacata acgtactgga aa             412
```

<210> SEQ ID NO 41
<211> LENGTH: 411
<212> TYPE: DNA
<213> ORGANISM: Varroa destructor

<400> SEQUENCE: 41

```
atggagaaca tcgcacagga cttcggtaaa aagtgccgat tgggcttcgc catctacccg      60
gctccgcagg tttccactgc cgttgtcgaa ccatacaact cggttttgac gacacatgcc    120
accctcgaac acgctgactg cgtattcatg atggataatg aggcgatcta tcagatctgt    180
cgtcggaatc ttggagttga acgaccggcg tatcaaaatc tcaatcgact gattagccag    240
gccgtttcgg cgataaccgc ttctctacgt ttttccggag cgttgaatgt tgacctcaac    300
gaatttcaga cgaatctcgt cccctacccg cgaatccatt tcccgctcgt cacttatgct    360
```

```
ccgattattt cggctgagaa ggctcatcac gagcaacata acgtactgga a        411
```

<210> SEQ ID NO 42
<211> LENGTH: 266
<212> TYPE: DNA
<213> ORGANISM: Varroa destructor

<400> SEQUENCE: 42

```
attttattca attaaagtat ttaccaattg gaataaagat aggattaatg ataattttt    60
taagtttaag tggaatacct ccctttatag gatttatttc taagataact gttttgttga  120
tgtattttga gaatcaaaaa ataattttt taattatatt attagtatct gtaataagaa   180
tatatattta tataaattat tttatgaaga gtttattttt tataagatta ggttataata  240
aaaataaaaa ataggaata agaaga                                        266
```

<210> SEQ ID NO 43
<211> LENGTH: 99
<212> TYPE: DNA
<213> ORGANISM: Varroa destructor

<400> SEQUENCE: 43

```
atacctcaaa tgtatccttc atattgagta ttaattcata tagtatttat attgaattat   60
tatataataa taatttatta ttattttata tttaagtaa                          99
```

<210> SEQ ID NO 44
<211> LENGTH: 501
<212> TYPE: DNA
<213> ORGANISM: Varroa destructor

<400> SEQUENCE: 44

```
ggccaatccc gattccggcg acacaaagaa attacaagaa gctatagacc gttttcatcg   60
agccggaaga tggattaaga aaaattttcg agatctattc atgctatgtt cgggtaaaca  120
gcgcaaccag atctcggatc aaacctacgc cgaagacctg gacctcgaca caggggtcat  180
tattatggat ggacaggtta ttaagaagga tagccccacg cccgaactca tcgatgggtt  240
ggatgttggt tttcaagctg ataagcaaca ggcgcaggtg attgtaatgc aaaagcttaa  300
aaacaattcc cgacctatca ttggcgactc aaaggaattt agcaacaaag ttcatccagg  360
ccccgacttt tgcctggtaa agccgaacga caacggcgaa ggcctcgtgc aagacaccga  420
gcttggggcc tccacgccgc tcagctcgcc ttcctgtata gttgaacagc ctctgtctca  480
cgacagtgtg ggcctgccac c                                            501
```

<210> SEQ ID NO 45
<211> LENGTH: 21
<212> TYPE: DNA
<213> ORGANISM: Artificial sequence
<220> FEATURE:
<223> OTHER INFORMATION: Exemplary siRNA targeting sequence

<400> SEQUENCE: 45

```
attttattca attaaagtat t                                             21
```

<210> SEQ ID NO 46
<211> LENGTH: 21
<212> TYPE: DNA
<213> ORGANISM: Artificial sequence
<220> FEATURE:
<223> OTHER INFORMATION: Exemplary siRNA targeting sequence

<400> SEQUENCE: 46

```
atacctcaaa tgtatccttc a                                              21

<210> SEQ ID NO 47
<211> LENGTH: 21
<212> TYPE: DNA
<213> ORGANISM: Artificial sequence
<220> FEATURE:
<223> OTHER INFORMATION: Exemplary siRNA targeting sequence

<400> SEQUENCE: 47
ggccaatccc gattccggcg a                                              21

<210> SEQ ID NO 48
<211> LENGTH: 24
<212> TYPE: DNA
<213> ORGANISM: Artificial sequence
<220> FEATURE:
<223> OTHER INFORMATION: T7 promoters

<400> SEQUENCE: 48
ctaatacgac tcactatagg gcga                                           24

<210> SEQ ID NO 49
<211> LENGTH: 24
<212> TYPE: DNA
<213> ORGANISM: Artificial sequence
<220> FEATURE:
<223> OTHER INFORMATION: T7 promoters (reverse complement orientation)

<400> SEQUENCE: 49
tcgccctata gtgagtcgta ttag                                           24

<210> SEQ ID NO 50
<211> LENGTH: 419
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (395)..(419)
<223> OTHER INFORMATION: Promoter

<400> SEQUENCE: 50
ctaatacgac tcactatagg gcgagttagc cgtctgaagc aatgcttgac tgtacagggt     60
ccgaatataa aacttcatac attcaaaatc acgtatcagg attatgctaa acatcgcacc    120
ataaaaatct tcactaaagt tatttttacgc ttcaggatag tggtccgtta tgagtgttgc   180
ggtattagtg cgtttacaaa tttgctaacg atattaacaa gcttatttca ctcgttggca    240
ggttttctag aacgcgaggt gaggaaggat aaccttccga tgatgtcatt cggcgacaat    300
cctgaggcgc ctcagcctcg ggagatgatt gatctagaag caacctttga gaaactcgaa    360
aacgaactca atgaggtagt tttctgtgtt gaaattcgcc ctatagtgag tcgtattag    419

<210> SEQ ID NO 51
<211> LENGTH: 361
<212> TYPE: DNA
<213> ORGANISM: Artificial sequence
<220> FEATURE:
<223> OTHER INFORMATION: A double stranded RNA expressing construct
```

```
            targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (337)..(361)
<223> OTHER INFORMATION: Promoter

<400> SEQUENCE: 51
ctaatacgac tcactatagg gcgactgtac agggtccgaa tataaaactt catacattca      60
aaatcacgta tcaggattat gctaaacatc gcaccataaa aatcttcact aaagttattt     120
tacgcttcag gatagtggtc cgttatgagt gttgcggtat tagtgcgttt acagatttgc     180
taacgttatt aacaagctaa tttcactcgt tggcaggttt tctagaacgc gaggtgagga     240 aggataaccct tccgatgatg tcattcggcg acaatcctga ggcgcctcag cctcgggaga    300
tgattgatct agaagcaacc tttgagaaac tcgaaaatcg ccctatagtg agtcgtatta     360
g                                                                    361

<210> SEQ ID NO 52
<211> LENGTH: 359
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (335)..(359)
<223> OTHER INFORMATION: Promoter

<400> SEQUENCE: 52
ctaatacgac tcactatagg gcgattcgag tttctcaaag gttgcttcta gatcaatcat      60
ctcccgaggc tgaggcgcct caggattgtc gccgaatgac atcatcggaa ggttatcctt     120
cctcacctcg cgttctagaa aacctgccaa cgagtgaaat tagcttgtta ataacgttag     180
caaatctgta aacgcactaa taccgcaaca ctcataacgg accactatcc tgaagcgtaa     240
ataactttta gtgaagattt ttatggtgcg atgtttagca taatcctgat acgtgatttt     300
gaatgtatga agttttatat tcggaccctg tacagtcgcc ctatagtgag tcgtattag     359

<210> SEQ ID NO 53
<211> LENGTH: 290
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (266)..(290)
<223> OTHER INFORMATION: Promoter

<400> SEQUENCE: 53
ctaatacgac tcactatagg gcgacaactc attaaaatga aatcagtatt ccacatcatg      60
aatcaattga atatggacgt cactcagaag tgtcttattg ccgaatgctg gattcctgat     120
```

```
cgcgatgtag caaaggtaca agctgccctg cgacgtggaa cggaagcggc tggaagcagc    180
ttcccgtgta tcattaaccg gttggaaacg gaccaagctc caccgacgtt ctacagaacg    240
aactcgttta ctgctggctt tcaaaatcgc cctatagtga gtcgtattag               290
```

<210> SEQ ID NO 54
<211> LENGTH: 261
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (237)..(261)
<223> OTHER INFORMATION: Promoter

<400> SEQUENCE: 54

```
ctaatacgac tcactatagg gcgacaattc gtgattcaat tgaatatgga cgtcactcag    60
aagtgtctta ttgccgaatg ctggattcct gatcgcgatg tagcaaaggt acaagctgcc   120
ctgcgacgtg gaacggaagc ggctggaagc agcttcccgt gtatcattaa ccggttggaa   180
acggacaaag ctccaccgac gttctacaga acgaactcgt ttactgctgg ctttcaatcg   240
ccctatagtg agtcgtatta g                                             261
```

<210> SEQ ID NO 55
<211> LENGTH: 249
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (225)..(249)
<223> OTHER INFORMATION: Promoter

<400> SEQUENCE: 55

```
ctaatacgac tcactatagg gcgacaattg aatatggacg tcactcagaa gtgtcttatt    60
gccgaatgct ggattcctga tcgcgatgta gcaaaggtac aagctgccct gcgacgtgga   120
acggaagcgg ctggaagcag cttcccgtgt atcattaacc ggttggaaac ggacaaagct   180
ccaccgacgt tctacagaac gaactcgttt attgctggct ttcaatcgcc ctatagtgag   240
tcgtattag                                                           249
```

<210> SEQ ID NO 56
<211> LENGTH: 355
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (331)..(355)
<223> OTHER INFORMATION: Promoter

<400> SEQUENCE: 56

```
ctaatacgac tcactatagg gcgaaatcac aattttctac atcatcttct tcatctgctt      60
ggcggcattc tggacggtta tgctggtcat cttctatcag acactcgatg ccttccagcc     120
aaagtggacc ctggacgcta gtctcattgg cactgtaccg ggattaggct tcaggccacg     180
cccaccgctg tctaacatcg actcaacact catctatttc aaggtatcta agccgttagt     240
gtatatgtta tattatagcg ctctttgtta tgtggaaaga cgccagggcg cgtatctata     300
tggtggtttt cataccaacc gtgggaaccc actaatacga ctcactatag ggcga          355
```

<210> SEQ ID NO 57
<211> LENGTH: 338
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (314)..(338)
<223> OTHER INFORMATION: Promoter

<400> SEQUENCE: 57

```
ctaatacgac tcactatagg gcgaggttcc cacggttggt atgaaaacca ccatatagat      60
acgcgccctg gcgtctttcc acataacaaa gagcgctata atataacata cactaacg      120 gcttagatac cttgaaatag atgagtgttg agtcgatgtt agacagcggt gggcgtggcc     180
tgaagcctaa tcccggtaca gtgccaatga gactagcgtc cagggtccac tttggctgga     240
aggcatcgag tgtctgatag aagatgacca gcataaccgt ccagaatgcc gccaagcaga     300
tgaagaagat gatgtcgccc tatagtgagt cgtattag                             338
```

<210> SEQ ID NO 58
<211> LENGTH: 338
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (314)..(338)
<223> OTHER INFORMATION: Promoter

<400> SEQUENCE: 58

```
ctaatacgac tcactatagg gcgacatcat cttcttcatc tgcttggcgg cattctggac      60
ggttatgctg gtcatcttct atcagacact cgatgccttc cagccaaagt ggaccctgga     120
cgctagtctc attggcactg taccgggatt aggcttcagg ccacgccac cgctgtctaa     180 catcgactca acactcatct atttcaaggt atctaagccg ttagtgtata tgttatatta     240
tagcgctctt tgttatgtgg aaagacgcca gggcgcgtat ctatatggtg gttttcatac     300
caaccgtggg aacctcgccc tatagtgagt cgtattag                             338
```

<210> SEQ ID NO 59
<211> LENGTH: 405
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (381)..(405)
<223> OTHER INFORMATION: Promoter

<400> SEQUENCE: 59

```
ctaatacgac tcactatagg gcgagaggtg acatccgtgt tcgccgtgta cggcatcaaa      60
gtggatccaa gacatctaag tctggtaggg gactacatga cttcgacgg agcttaccgc     120
gccttcaaca gaatccacat ggcaaacaat gcatcgccac tccagcagat gagctttgaa    180
acgacgtgca catttatgaa aaacgctgct ttatttggta cgaaatcccc taagacagat    240
acgaagacaa tctttgccat gctaatagtg tttctgtttt tagtgcctgg tacgatcatt    300
aattacggcg ttgaaagtaa ctccaaacag cgaccctata tgtcttcata caagagactt    360
agttctagga aagcaaatac atcgccctat agtgagtcgt attag                    405
```

<210> SEQ ID NO 60
<211> LENGTH: 373
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (349)..(373)
<223> OTHER INFORMATION: Promoter

<400> SEQUENCE: 60

```
ctaatacgac tcactatagg gcgatatgaa gacatatagg gtcgctgttt ggagttactt      60
tcaacgccgt aattaatgat cgtaccaggc actaaaaaca gaaacactat tagcatggca    120
aagattgtct tcgtatctgt cttaggggat ttcgtaccaa ataaagcagc gttttttcata   180
aatgtgcacg tcgtttcaaa gctcatctgc tggagtggcg atgcattgtt tgccatgtgg    240
attctgttga aggcgcggta agctccgtcg aaagtcatgt agtcccctac cagacttaga    300
tgtcttggat ccactttgat gccgtacacg gcgaacacgg atgtcacctt cgccctatag    360
tgagtcgtat tag                                                        373
```

<210> SEQ ID NO 61
<211> LENGTH: 372
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:

```
<221> NAME/KEY: misc_feature
<222> LOCATION: (348)..(372)
<223> OTHER INFORMATION: Promoter

<400> SEQUENCE: 61
ctaatacgac tcactatagg gcgaatgaag acatataggg tcgctgtttg gagttacttt      60
caacgccgta attaatgatc gtaccaggca ctaaaaacag aaacactatt agcatggcaa    120
agattgtctt cgtatctgtc ttaggggatt tcgtaccaaa taaagcagcg ttttttcataa   180 atgtgcacgt cgtttcaaag ctcatctgct ggagtggcga tgcattgttt gccatgtgga   240
ttctgttgaa ggcgcggtaa gctccgtcga aagtcatgta gtcccctacc agacttagat   300
gtcttggatc cactttgatg ccgtacacgg cgaacacgga tgtcaccttc gccctatagt   360
gagtcgtatt ag                                                        372

<210> SEQ ID NO 62
<211> LENGTH: 453
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (429)..(453)
<223> OTHER INFORMATION: Promoter

<400> SEQUENCE: 62
ctaatacgac tcactatagg gcgacctgcg catccatcag atgattggaa cggaggaaaa     60
tgtccaagta gcattcgtgg gctcgattgt cgagtgtcac aagctcaagg tgtttactca   120
ggaagaagca ctgagattcc ttgcggcaaa gatgaagcag cggatgtttg accacagaa    180 agcggaagac cccttgacaa ggcatgggaa gccgtacttt catccgtagt caaccatatt   240
cccgttcaat cgcctgacta caatatgact gtccgggcac actatcttgc actaatggtg   300
cgtcgcatca ttcaggcgcg ttatgatcgc cgcttcattg acgatcgcga ctattacggc   360
aacaaacgaa ttgagcttcc gggttcgatg atatcgctgc tgtttgaaga cctgttaaaa   420
aaggttaatt cgccctatag tgagtcgtat tag                                 453

<210> SEQ ID NO 63
<211> LENGTH: 331
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (307)..(331)
<223> OTHER INFORMATION: Promoter

<400> SEQUENCE: 63
ctaatacgac tcactatagg gcgatcagat ttcagatgat tggaacggag gaaaatgtcc     60
aagtagcatt cgtgggctcg attgtcgagt gtcacaagct caaggtgttt actcaggaag   120
aagcactgag attccttgcg gcaaagatga agcagcggat gtttggacca cagaaagcgg   180
```

```
aagaccccct tgacaaggca tgggaagccg tactttcatc cgtagtcaac catattcccg    240
ttcaatcgcc tgactacaat atgaccgtcc gggcacacta tcttgcacta atggtgcgtc    300
acatcattcg ccctatagtg agtcgtatta g                                   331
```

<210> SEQ ID NO 64
<211> LENGTH: 429
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (405)..(429)
<223> OTHER INFORMATION: Promoter
<400> SEQUENCE: 64

```
ctaatacgac tcactatagg gcgatcagat gattggaacg gaggaaaatg tccaagtagc    60
attcgtgggc tcgattgtcg agtgtcacaa gctcaaggtg tttactcagg aagaagcact   120
gagattcctt gcggcaaaga tgaagcagcg gatgtttgga ccacagaaag cggaagaccc   180
ccttgacaag gcatgggaag ccgtactttc atccgtagtc aaccatattc ccgttcaatc   240
gcctgactac aatatgaccg tccgggcaca ctatcttgca ctaatggtgc gtcacatcat   300
tcaggcgcgt tatgatcgcc gcttcattga cgatcgcgac tattacggca acaaacgaat   360
tgagcttccg ggttcgatga tatcgctgct gtttgaagac ctgtttcgcc ctatagtgag   420
tcgtattag                                                           429
```

<210> SEQ ID NO 65
<211> LENGTH: 494
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (470)..(494)
<223> OTHER INFORMATION: Promoter
<400> SEQUENCE: 65

```
ctaatacgac tcactatagg gcgaaatcaa ttcgtctgca gatctcaccg attttctgat    60
atcgctggga gtccaggata ttcgactact atgcggagct gaattcagca aaacacacgt   120
ctactatgta ttccacaacg gtgttattaa aggcgtcgtt gaggatcatc gcaggcttat   180
caacgagatt cggcaatttc gtcggaaggg atacttgtcg ccttacttat cagtttatcc   240
aaatcatcta catcgctgtg tgtatattgt aactgacggt ggtcgtttct gcaggccgtt   300
tatcattgtt gaggatggtc agccaaaagt tacgcagaaa catttggacg acctcaaagc   360
caatatatat aacttccaag acttcctgga catgggcttt gtagagtttc tcgatgtaaa   420
tgaggaaaac gacgcgctta tcgccatttta tgaaaaagat atcacaatca tcgccctata   480
gtgagtcgta ttag                                                     494
```

<210> SEQ ID NO 66
<211> LENGTH: 476
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (452)..(476)
<223> OTHER INFORMATION: Promoter

<400> SEQUENCE: 66
ctaatacgac tcactatagg gcgattcata aatggcgata agcgcgtcgt tttcctcatt      60
tacatcgaga aactctacaa agcccatgtc caggaagtct tggaagttat atatattggc     120
tttgaggtcg tccaaatgtt tctgcgtaac ttttggctga ccatcctcaa caatgataaa     180
cggcctgcag aaacgaccac cgtcagttac aatatacaca cagcgatgta gatgatttgg     240
ataaactgat aagtaaggcg acaactatcc cttccgacga aattgccgaa tctcgttgat     300
aagcctgcga tgatcctcaa cgacgccttt aataacaccg ttgtggaata catagtagac     360
gtgtgttttg ctgaattcag ctccgcatag tagtcgaata tcctggactc ccagcgatat     420
cagaaaatcg gtgagatctg cagacgaatt gatcgcccta tagtgagtcg tattag        476

<210> SEQ ID NO 67
<211> LENGTH: 474
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (450)..(474)
<223> OTHER INFORMATION: Promoter

<400> SEQUENCE: 67
ctaatacgac tcactatagg gcgatcaatt cgtctgcaga tctcaccgat tttctgatat 60
cgctgggaat ccaggatatt cgactactat gcggagctga attcagcaaa acacacgtct 120
actatgtatt ccacaacggt gttattaaag gcgtcgttga ggatcatcgc aggcttatca 180
acgagattcg gcaatttcgt cggaagggat acttgtcgcc ttacttatca gtttatccaa 240
atcatctaca tcgctgtgtg tatattgtaa ctgacggtgg tcgtttctgc aggccgttta 300
tcattgttga ggatggtcag ccaaaagtta cgcagaaaca tttggacgac ctcaaagcca 360
atatatataa cttccaagac ttcctggaca tgggctttgt agagtttctc gatgtaaatg 420
aggaaaacga cgcgcttatc gccatttatg tcgccctata gtgagtcgta ttag 474

<210> SEQ ID NO 68
<211> LENGTH: 426
<212> TYPE: DNA
<213> ORGANISM: Artificial sequence
<220> FEATURE:
<223> OTHER INFORMATION: A double stranded RNA expressing construct targeting a Varroa gene
<220> FEATURE:

```
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (402)..(426)
<223> OTHER INFORMATION: Promoter

<400> SEQUENCE: 68
ctaatacgac tcactatagg gcgagttttg aacaaaatga gtgttgagcg cggatttaag      60
gccggtgtag tatataaaac agaaacgatc aatttgcgta agttatctgg ggatgtggga    120
gtccagacat cgtgcgtttt tggtcgaaag gcaggagatt ctgagttaca gaaatttgta    180
gatgttgatg gcctgccata catcggcagc agggtagtac agggagatcc ggtatgtgca    240
tatataaatt tgaccacggg acaactgaag actgtaaggt attactcgac cgagccagca    300
atcgtgcatg aagtgaaaat tcttggtaat gattccggta cagacaccct ccaacaaatc    360
cagttgacgt atcttattga tcgaacgcca aatgatcgga gatcgcccta tagtgagtcg    420
tattag                                                               426

<210> SEQ ID NO 69
<211> LENGTH: 415
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (391)..(415)
<223> OTHER INFORMATION: Promoter

<400> SEQUENCE: 69
ctaatacgac tcactatagg gcgaaatgag tgttgagcgc ggatttaagg ccggtgtagt      60
atataaaaca gaaacgatca atttgcgtaa gttatctggg gatgtgggag tccagacatc    120
gtgcgttttt ggtcgaaagg caggagattc tgagttacag aaatttgtag atgttgatgg    180
cctgccatac atcggcagca gggtagtaca gggagatccg gtatgtgcat atataaattt    240
gaccacggga caactgaaga ctgtaaggta ttactcgacc gagccagcaa tcgtgcatga    300
agtgaaaatt cttggtaatg attccggtac agacaccctc caacaaatcc agttgacgta    360
tcttgttgat cgaacgccaa atgatcggag atcgccctat agtgagtcgt attag         415

<210> SEQ ID NO 70
<211> LENGTH: 414
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (390)..(414)
<223> OTHER INFORMATION: Promoter

<400> SEQUENCE: 70
ctaatacgac tcactatagg gcgaaatgag tgttgagcgc ggatttaagg ccggtgtagt      60
```

```
atataaaaca gaaacgatca atttgcgtaa gttatctggg gatgtgggag tccagacatc      120
gtgcgttttt ggtcgaaagg caggagattc tgagttacaa aaatttgtag atgttgatgg      180
cctgccatac atcggcagca gggtagtaca gggagatccg gtatgtgcat atataaattt      240
gaccacggga caactgaaga ctgtaaggta ttactcgacc gagccagcaa tcgtgcatga      300
agtgaaaatt cttggtaatg attccggtac agacaccctc caacaaatcc agctgacgta      360
tcttgttgat cgaacgccaa atgatcggag tcgccctata gtgagtcgta ttag           414
```

<210> SEQ ID NO 71
<211> LENGTH: 316
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (292)..(316)
<223> OTHER INFORMATION: Promoter

<400> SEQUENCE: 71

```
ctaatacgac tcactatagg gcgaaatggt ttctgctacc tgtgaggata gtatgcggga       60
tgcttgtatt cgttttcttg cctcgaaagt caatctcaaa gcgcttgaca gtgagacaga      120
gcttatgctc attgaagagg ccggcaaagt ggcagccctc gtcggtggag aggagtttgt      180
gctgctggtt aagctcctca attcattaaa ggtagattgt acattttggc gtcttctcga      240
acaagttaga atctatttag caaagtgcca atgtatcagc ttccaatacg catcgcccta      300
tagtgagtcg tattag                                                     316
```

<210> SEQ ID NO 72
<211> LENGTH: 311
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (287)..(311)
<223> OTHER INFORMATION: Promoter

<400> SEQUENCE: 72

```
ctaatacgac tcactatagg gcgaattgga agctgataca ttggcacttt gctaaataga       60
ttctaacttg ttcgagaaga cgccaaaatg tacaatctac ctttaatgaa ttgaggagct      120
taaccagcag cacaaactcc tctccaccga cgagggctgc cactttgccg gcctcttcaa      180
tgagcataag ctctgtctct ctgtcaagcg ctttgagatt gactttcgag gcaagaaaac      240
gaatacaagc atcccgcata ctatcctcac aggtagcaga aaccatttcg ccctatagtg      300
agtcgtatta g                                                          311
```

<210> SEQ ID NO 73
<211> LENGTH: 311
<212> TYPE: DNA

```
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (287)..(311)
<223> OTHER INFORMATION: Promoter

<400> SEQUENCE: 73
ctaatacgac tcactatagg gcgaattgga agctgataca ttggcacttt gctaaataga     60
ttctaacttg ttcgagaaga cgccaaaatg tacaatctac ctttaatgaa ttgaggagct    120
taaccagcag cacaaactcc tctccaccga cgagggctgc cactttgccg gcctcttcaa    180
tgagcataag ctctgtctct ctgtcaagcg ctttgagatt gactttcgag gcaagaaaac    240
gaatacaagc atcccgcata ctatcctcac aggtagcaga aaccatttcg ccctatagtg    300
agtcgtatta g                                                         311

<210> SEQ ID NO 74
<211> LENGTH: 327
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (303)..(327)
<223> OTHER INFORMATION: Promoter

<400> SEQUENCE: 74
ctaatacgac tcactatagg gcgagatctt gttgaagccg gcttcttctt ccttggcatg     60
cacgattaca cgaaatgctt ccattgcgac ggcggtctgt gtaattggga gacaggtgac    120
gaccctgggt agagcatgcc cgctggttcc ctgaatgtc aattcgttca gctaagcaag    180
ggcggagcat tcatcgctga gtgccaacaa cgtcacgaaa aactagttaa tggcgcggta    240
gcccaggcag aacttcaggc ttttagtgaa gtagaaccgg gaggaacagg cagtgactca    300
aattcgccct atagtgagtc gtattag                                        327

<210> SEQ ID NO 75
<211> LENGTH: 311
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (287)..(311)
<223> OTHER INFORMATION: Promoter

<400> SEQUENCE: 75
ctaatacgac tcactatagg gcgaagtcac tgcctgttcc tcccggttct acttcactaa     60
```

```
aagcctgaag ttctgcctgg gctaccgcgc cattaactag tttttcgtga cgttgttggc      120
actcagcgat gaatgctccg cccttgctta gctgaacgaa ttgacattca gggaaccagc      180
gggcatgctc tacccagggg tcgtcacctg tctcccaatt acacagaccg ccgtcgcaat      240
ggaagcattt cgtgtaatcg tgcatgccaa ggaagaagaa gccggcttcg ccctatagtg      300
agtcgtatta g                                                           311

<210> SEQ ID NO 76
<211> LENGTH: 347
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (323)..(347)
<223> OTHER INFORMATION: Promoter

<400> SEQUENCE: 76
ctaatacgac tcactatagg gcgattccgc ttcatttgag aactgagctt gaagaaataa      60
tgcagtcgcc cgtcgtcaag ttctacctcg agaaaggtgt accgaaacaa gtgattcgaa      120
tgaccgtaaa aaatatatgc ttgacaacga gcgcggtttc cgtgatcttg acgaaattac      180
acacgtactc ggacaggtgc tcagcttcgg caacaagaag actgcgcctg ccaatgaaaa      240
aggtaggtgg ataccggata tttgtcggga attcaatgca gctgaacccg atgaggttga      300
ttcagaattg gcatacaata gaatcgccct atagtgagtc gtattag                    347

<210> SEQ ID NO 77
<211> LENGTH: 332
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (308)..(332)
<223> OTHER INFORMATION: Promoter

<400> SEQUENCE: 77
ctaatacgac tcactatagg gcgattccgc ttcatttgag aactgagctt gaagaaataa      60
tgcagtcgcc cgtcgtcaag ttctacctcg agaaaggtgt accgaaacaa gtgattcgaa      120
tgaccgtaaa aaatatatg cttgacaacg agcgcggttt ccgtgatctt gacgaaatta      180
cacacgtact cggacaggtg ctcagcttcg gcaacaagaa gactgcgcct gccaatgaaa      240
aaggtaggtg ataccggat atttgtcggg aattcaatgc agctgaaccc gatgaggttg      300
attcagaatc gccctatagt gagtcgtatt ag                                    332

<210> SEQ ID NO 78
<211> LENGTH: 331
<212> TYPE: DNA
<213> ORGANISM: Artificial sequence
<220> FEATURE:
<223> OTHER INFORMATION: A double stranded RNA expressing construct
``` targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (307)..(331)
<223> OTHER INFORMATION: Promoter

<400> SEQUENCE: 78

```
ctaatacgac tcactatagg gcgattccgc ttcatttgag aactgagctt gaagaaataa      60
tgcagtcgcc cgtcgtcaag ttctacctcg agaaaggtgt accgaaacaa gtgattcgaa     120
tgaccgtgaa aaaatatatg cttgacaacg agcgcggttt ccgtgatctt gacgaaatta     180
cacacgtact cggacaggtg ctcagcttcg caacaagaa gactgcgcct gccaatgaaa      240
aaggtaggtg gataccggat atttgtcggg aattcaatgc agctgaaccc gatgaggttg     300
attcagatcg ccctatagtg agtcgtatta g                                    331
```

<210> SEQ ID NO 79
<211> LENGTH: 327
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (303)..(327)
<223> OTHER INFORMATION: Promoter

<400> SEQUENCE: 79

```
ctaatacgac tcactatagg gcgatggcta attaatagta ggccgaagaa cttttttgagt    60 ggcctcgata tgtccgacgt tgtggcttcg tgggaggttc ctttggttgg ccaagcttac    120
cgagtcgaat tcgaacacgg aagtgcaacg ggtaaacgtg ttgtgtacgt taatggactc    180
gaggtgttac gaaaacactg gctttttaag cttgttggcg aggaaagctt tgacatattg    240
ggacataagt gcatcatttc tatcaaagcc gtaggaggct tcaggttggt agcaaactcc    300
agttcgccct atagtgagtc gtattag                                        327
```

<210> SEQ ID NO 80
<211> LENGTH: 325
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (301)..(325)
<223> OTHER INFORMATION: Promoter

<400> SEQUENCE: 80

```
ctaatacgac tcactatagg gcgatggcta attaatagta ggccgaagaa cttttttgagt    60 ggcctcgata tgtccgacgt tgtggcttcg tgggaggttc ctttggttgg ccaagcttac    120
cgagtcgaat tcgaacacgg aagtgcaacg ggtaaacgtg ttgtgtacgt taatggactc    180
```

```
gaggtgttac gaaaacactg gctttttaag cttgttggcg aggaaagctt tgacatattg    240
ggacataagt gcatcatttc tatcaaagcc gtaggaggct tcaggttggt agcaaactcc    300
atcgccctat agtgagtcgt attag                                         325
```

```
<210> SEQ ID NO 81
<211> LENGTH: 325
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (301)..(325)
<223> OTHER INFORMATION: Promoter

<400> SEQUENCE: 81
```

```
ctaatacgac tcactatagg gcgatggagt ttgctaccaa cctgaagcct cctacggctt    60
tgatagaaat gatgcactta tgtcccaata tgtcaaagct ttcctcgcca acaagcttaa   120
aaagccagtg ttttcgtaac acctcgagtc cattaacgta cacaacacgt ttacccgttg   180
cacttccgtg ttcgaattcg actcggtaag cttggccaac caaaggaacc tcccacgaag   240
ccacaacgtc ggacatatcg aggccactca aaaagttctt cggcctacta ttaattagcc   300
atcgccctat agtgagtcgt attag                                         325
```

```
<210> SEQ ID NO 82
<211> LENGTH: 331
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (307)..(331)
<223> OTHER INFORMATION: Promoter

<400> SEQUENCE: 82
```

```
ctaatacgac tcactatagg gcgaggtctt gacaacacat gctaccctcg aacacgccga    60
ctgcgtcttc atgatggaca atgaggccat ctatcagatc tgccgtcgga accttggagt   120
cgagcgaccg gcgtaccaga atctcaaccg tctgatcagt caggccgttt cggcgattac   180
cgcttctcta cgtttctccg gagcgctgaa tgttgatctt aacgagttcc aaactaattt   240
agttccatac ccgcgaatcc attttcccct cgtcacttac gctccgatca tttctgctga   300
gaaggcttcg ccctatagtg agtcgtatta g                                  331
```

```
<210> SEQ ID NO 83
<211> LENGTH: 327
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
```

```
<222> LOCATION: (1)..(24)
<223> OTHER INFORMATION: Promoter
<220> FEATURE:
<221> NAME/KEY: misc_feature
<222> LOCATION: (303)..(327)
<223> OTHER INFORMATION: Promoter

<400> SEQUENCE: 83
ctaatacgac tcactatagg gcgaggtctt gacaacacat gctaccctcg aacacgccga      60
ctgcgtcttc atgatggaca atgaggccat ctatcagatc tgccgtcgga accttggagt     120
cgagcgaccg gcgtaccaga atctcaaccg tctgatcagt caggccgttt cggcgattac     180
cgcttctcta cgtttctccg gagcgctgaa tgttgatctt aacgagttcc aaactaattt     240
agttccatac ccgcgaatcc attttccccc cgtcacttac gctccgatca tttctgctga     300
gaatcgccct atagtgagtc gtattag                                         327

<210> SEQ ID NO 84
<211> LENGTH: 325
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (301)..(325)
<223> OTHER INFORMATION: Promoter

<400> SEQUENCE: 84
ctaatacgac tcactatagg gcgactcagc agaaatgatc ggagcgtaag tgacgggggg      60
aaaatggatt cgcgggtatg gaactaaatt agtttggaac tcgttaagat caacattcag     120
cgctccggag aaacgtagag aagcggtaat cgccgaaacg gcctgactga tcagacggtt     180
gagattctgg tacgccggtc gctcgactcc aaggttccga cggcagatct gatagatggc     240
ctcattgtcc atcatgaaga cgcagtcggc gtgttcgagg gtagcatgtg ttgtcaagac     300
ctcgccctat agtgagtcgt attag                                           325

<210> SEQ ID NO 85
<211> LENGTH: 380
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (356)..(380)
<223> OTHER INFORMATION: Promoter

<400> SEQUENCE: 85
ctaatacgac tcactatagg gcgacaacgc tgtgcttcac gtagactcca cgttcgaaaa      60
tgtcgactgc acgtttatgg ttgataatca aacactcttc aagctttgtc gagaccggct     120
aaagattagg agtccatctt atgacaacgc aaatgctgtc atttcccagg gttttttcgtc    180 aatcatgaat tcggtggggc tggatggatc cttgaatgtg gacctcagcg agttccaaac     240
```

```
aaatctcgtc ccttttggaa gattacattt tacgatgatg agctacagtc cattcgttac    300
atccggacac cgcgatctaa gccgtgagac gtccgtcgtg gagattactc gtgacctcgc    360
cctatagtga gtcgtattag                                                380
```

```
<210> SEQ ID NO 86
<211> LENGTH: 378
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (354)..(378)
<223> OTHER INFORMATION: Promoter

<400> SEQUENCE: 86
```

```
ctaatacgac tcactatagg gcgacaacgc tgtgcttcac gtagactcca cgttcgaaaa    60
tgtcgactgc acgtttatgg ttgataatca aacactcctc aagctttgtc gagaccggct   120
aaaggttagg agtccatctt atgacaacgc aaatgctgtc atttcccagg gttttcgtc    180 aatcatgaat tcggtggggc tggatggatc cttgaatgtg gacctcagcg agttccaaac   240
aagtctcgtc ccttttggaa gattacattt tacgatgatg agctacagtc cattcgttac   300
atccggacac cgcgatctaa gccgtgagac gtccgtcgtg gagattactc gtgatcgccc   360
tatagtgagt cgtattag                                                 378
```

```
<210> SEQ ID NO 87
<211> LENGTH: 377
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (353)..(377)
<223> OTHER INFORMATION: Promoter

<400> SEQUENCE: 87
```

```
ctaatacgac tcactatagg gcgaaacgct gtgcttcacg tagactccac gttcgaaaat    60
gtcgactgca cgtttatggt tgataatcaa acactcctca agctttgtcg agaccggcta   120
aaggttagga gtccatctta tgacaacgca aatgctgtca tttcccaggg ttttcgtga    180 atcatgaatt cggtggggct ggatggatcc ttgaatgtgg acctcagcga gttccaaaca   240
agtctcgtcc cttttggaag attacatttt acgatgatga gctacagtcc attcgttaca   300
tccggacacc gcgatctaag ccgtgagacg tccgtcgtgg agattactcg tgatcgccct   360
atagtgagtc gtattag                                                  377
```

```
<210> SEQ ID NO 88
<211> LENGTH: 463
<212> TYPE: DNA
<213> ORGANISM: Artificial sequence
<220> FEATURE:
<223> OTHER INFORMATION: A double stranded RNA expressing construct
``` targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (439)..(463)
<223> OTHER INFORMATION: Promoter

<400> SEQUENCE: 88

```
ctaatacgac tcactatagg gcgatatgga gaacatcgca caggacttcg gtaaaaagtg      60
ccgattgggc ttcgccatct acccggctcc gcaggtttcc actgccgttg tcgaaccata     120
caactcggtt ttgacgacac atgccaccct cgaacacgct gactgcgtat tcatgatgga     180
taatgaggcg atctatcaga tctgtcgtcg gaatcttgga gttgaacgac cggcgtatca     240
aaatctcaat cgactgatta gccaggccgt ttcggcgata accgcttctc tacgtttttc     300
cggagcgttg aatgttgacc tcaacgaatt tcagacgaat ctcgtcccct acccgcgaat     360
ccatttcccg ctcgtcactt atgctccgat tatttcggct gagaaggctc atcacgagca     420
acataacgta ctggaaatct cgccctatag tgagtcgtat tag                       463
```

<210> SEQ ID NO 89
<211> LENGTH: 460
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (436)..(460)
<223> OTHER INFORMATION: Promoter

<400> SEQUENCE: 89

```
ctaatacgac tcactatagg gcgaatggag aacatcgcac aggacttcgg taaaaagtgc      60
cgattgggct tcgccatcta cccggctccg caggtttcca ctgccgttgt cgaaccatac     120
aactcggttt tgacgacaca tgccaccctc gaacacgctg actgcgtatt catgatggat     180
aatgaggcga tctatcagat ctgtcgtcgg aatcttggat tgaacgaccg gcgtatcaa      240 aatctcaatc gactgattag ccaggccgtt tcggcgataa ccgcttctct acgttttcc      300 ggagcgttga atgttgacct caacgaattt cagacgaatc tcgtcccta cccgcgaatc      360 catttcccgc tcgtcactta tgctccgatt atttcggctg agaaggctca tcacgagcaa     420
cataacgtac tggaaatcgc cctatagtga gtcgtattag                           460
```

<210> SEQ ID NO 90
<211> LENGTH: 459
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (435)..(459)
<223> OTHER INFORMATION: Promoter

<400> SEQUENCE: 90

```
ctaatacgac tcactatagg gcgaatggag aacatcgcac aggacttcgg taaaaagtgc    60
cgattgggct tcgccatcta cccggctccg caggtttcca ctgccgttgt cgaaccatac   120
aactcggttt tgacgacaca tgccaccctc gaacacgctg actgcgtatt catgatggat   180
aatgaggcga tctatcagat ctgtcgtcgg aatcttggag ttgaacgacc ggcgtatcaa   240
aatctcaatc gactgattag ccaggccgtt tcggcgataa ccgcttctct acgttttcc    300
ggagcgttga atgttgacct caacgaattt cagacgaatc tcgtcccta cccgcgaatc    360
catttcccgc tcgtcactta tgctccgatt atttcggctg agaaggctca tcacgagcaa   420
cataacgtac tggaatcgcc ctatagtgag tcgtattag                          459
```

<210> SEQ ID NO 91
<211> LENGTH: 480
<212> TYPE: DNA
<213> ORGANISM: Artificial sequence
<220> FEATURE:
<223> OTHER INFORMATION: A double stranded RNA expressing construct
      targeting GFP
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (456)..(480)
<223> OTHER INFORMATION: Promoter

<400> SEQUENCE: 91

```
ctaatacgac tcactatagg gcgagccaac acttgtcact actttcggtt atggtgttca    60
atgctttgcg agatacccag atcatatgaa acagcatgac ttttcaaga gtgccatgcc    120
tgaaggttat gtacaggaaa gaactatatt tttcaaagat gacgggaact acaagacacg   180
tgctgaagtc aagtttgaag gtgatacct tgttaataga tcgagttaa aggtattga     240
ttttaaagaa gatggaaaca ttcttggaca caaattggaa tacaactata actcacacaa   300
tgtatacatc atggcagaca acaaaagaa tggaatcaaa gttaacttca aaattagaca    360
caacattgaa gatggaagcg ttcaactagc agaccattat caacaaaata ctccaattgg   420
cgatggccct gtccttttac cagacaacca ttaccttcgc cctatagtga gtcgtattag   480
```

<210> SEQ ID NO 92
<211> LENGTH: 478
<212> TYPE: DNA
<213> ORGANISM: Artificial sequence
<220> FEATURE:
<223> OTHER INFORMATION: A double stranded RNA expressing construct
      targeting GFP

<400> SEQUENCE: 92

```
taatacgact cactataggg cgagccaaca cttgtcacta ctttcggtta tggtgttcaa    60
tgctttgcga gatacccaga tcatatgaaa cagcatgact ttttcaagag tgccatgcct   120
gaaggttatg tacaggaaag aactatattt ttcaaagatg acgggaacta caagacacgt   180
gctgaagtca gtttgaagg tgataccctt gttaataga tcgagttaaa ggtattgat     240
tttaaagaag atggaaacat tcttggacac aaattggaat acaactataa ctcacacaat   300
gtatacatca tggcagacaa acaaaagaat ggaatcaaag ttaacttcaa aattagacac   360
aacattgaag atggaagcgt tcaactagca gaccattatc aacaaaatac tccaattggc   420
```

```
gatggccctg tcctttacc agacaaccat taccttcgcc ctatagtgag tcgtatta      478
```

<210> SEQ ID NO 93
<211> LENGTH: 459
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 93

```
ctaatacgac tcactatagg gcgaatggag aacatcgcac aggacttcgg taaaaagtgc      60
cgattgggct tcgccatcta cccggctccg caggtttcca ctgccgttgt cgaaccatac     120
aactcggttt tgacgacaca tgccaccctc gaacacgctg actgcgtatt catgatggat     180
aatgaggcga tctatcagat ctgtcgtcgg aatcttggag ttgaacgacc ggcgtatcaa     240
aatctcaatc gactgattag ccaggccgtt tcggcgataa ccgcttctct acgttttcc      300
ggagcgttga atgttgacct caacgaattt cagacgaatc tcgtccccta cccgcgaatc     360
catttcccgc tcgtcactta tgctccgatt atttcggctg agaaggctca tcacgagcaa     420
cataacgtac tggaatcgcc ctatagtgag tcgtattag                            459
```

<210> SEQ ID NO 94
<211> LENGTH: 325
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 94

```
ctaatacgac tcactatagg gcgaggtctt gacaacacat gctaccctcg aacacgccga      60
ctgcgtcttc atgatggaca atgaggccat ctatcagatc tgccgtcgga accttggagt     120
cgagcgaccg gcgtaccaga atctcaaccg tctgatcagt caggccgttt cggcgattac     180
cgcttctcta cgtttctccg gagcgctgaa tgttgatctt aacgagttcc aaactaattt     240
agttccatac ccgcgaatcc attttccccct cgtcacttac gctccgatca tttctgctga    300
gtcgccctat agtgagtcgt attag                                           325
```

<210> SEQ ID NO 95
<211> LENGTH: 377
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 95

```
ctaatacgac tcactatagg gcgaaacgct gtgcttcacg tagactccac gttcgaaaat      60
gtcgactgca cgtttatggt tgataatcaa acactcttca agctttgtcg agaccggcta     120
aagattagga gtccatctta tgacaacgca aatgctgtca tttcccaggg tttttcgtca     180
atcatgaatt cggtggggct ggatggatcc ttgaatgtgg acctcagcga gttccaaaca     240
aatctcgtcc cttttggaag attacatttt acgatgatga gctacagtcc attcgttaca     300
tccggacacc gcgatctaag ccgtgagacg tccgtcgtgg agattactcg tgatcgccct     360
atagtgagtc gtattag                                                    377
```

<210> SEQ ID NO 96

<211> LENGTH: 428
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 96

| | | | | | |
|---|---|---|---|---|---|
| ctaatacgac | tcactatagg | gcgatcagat | gattggaacg | gaggaaaatg | tccaagtagc | 60 |
| attcgtgggc | tcgattgtcg | agtgtcacaa | gctcaaggtg | tttactcagg | aagaagcact | 120 |
| gagattcctt | gcggcaaaga | tgaagcagcg | gatgtttgga | ccacagaaag | cggaagaccc | 180 |
| cttgacaagg | catgggaagc | cgtactttca | tccgtagtca | accatattcc | cgttcaatcg | 240 |
| cctgactaca | atatgactgt | ccgggcacac | tatcttgcac | taatggtgcg | tcgcatcatt | 300 |
| caggcgcgtt | atgatcgccg | cttcattgac | gatcgcgact | attacggcaa | caaacgaatt | 360 |
| gagcttccgg | gttcgatgat | atcgctgctg | tttgaagacc | tgtttcgccc | tatagtgagt | 420 |
| cgtattag | | | | | | 428 |

<210> SEQ ID NO 97
<211> LENGTH: 474
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 97

| | | | | | |
|---|---|---|---|---|---|
| ctaatacgac | tcactatagg | gcgatcaatt | cgtctgcaga | tctcaccgat | tttctgatat | 60 |
| cgctgggagt | ccaggatatt | cgactactat | gcggagctga | attcagcaaa | acacacgtct | 120 |
| actatgtatt | ccacaacggt | gttattaaag | gcgtcgttga | ggatcatcgc | aggcttatca | 180 |
| acgagattcg | gcaatttcgt | cggaagggat | acttgtcgcc | ttacttatca | gtttatccaa | 240 |
| atcatctaca | tcgctgtgtg | tatattgtaa | ctgacggtgg | tcgtttctgc | aggccgttta | 300 |
| tcattgttga | ggatggtcag | ccaaaagtta | cgcagaaaca | tttggacgac | ctcaaagcca | 360 |
| atatatataa | cttccaagac | ttcctggaca | tgggctttgt | agagtttctc | gatgtaaatg | 420 |
| aggaaaacga | cgcgcttatc | gccatttatg | tcgccctata | gtgagtcgta | ttag | 474 |

<210> SEQ ID NO 98
<211> LENGTH: 414
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 98

| | | | | | |
|---|---|---|---|---|---|
| ctaatacgac | tcactatagg | gcgaaatgag | tgttgagcgc | ggatttaagg | ccggtgtagt | 60 |
| atataaaaca | gaaacgatca | atttgcgtaa | gttatctggg | gatgtgggag | tccagacatc | 120 |
| gtgcgttttt | ggtcgaaagg | caggagattc | tgagttacag | aaatttgtag | atgttgatgg | 180 |
| cctgccatac | atcggcagca | gggtagtaca | gggagatccg | gtatgtgcat | atataaattt | 240 |
| gaccacggga | caactgaaga | ctgtaaggta | ttactcgacc | gagccagcaa | tcgtgcatga | 300 |
| agtgaaaatt | cttggtaatg | attccggtac | agacaccctc | caacaaatcc | agttgacgta | 360 |
| tcttattgat | cgaacgccaa | atgatcggag | tcgccctata | gtgagtcgta | ttag | 414 |

<210> SEQ ID NO 99

```
<211> LENGTH: 372
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 99
ctaatacgac tcactatagg gcgaaggtga catccgtgtt cgccgtgtac ggcatcaaag     60
tggatccaag acatctaagt ctggtagggg actacatgac tttcgacgga gcttaccgcg    120
ccttcaacag aatccacatg gcaaacaatg catcgccact ccagcagatg agctttgaaa    180
cgacgtgcac atttatgaaa aacgctgctt tatttggtac gaaatcccct aagacagata    240
cgaagacaat ctttgccatg ctaatagtgt ttctgttttt agtgcctggt acgatcatta    300
attacggcgt tgaaagtaac tccaaacagc gaccctatat gtcttcattc gccctatagt    360
gagtcgtatt ag                                                        372

<210> SEQ ID NO 100
<211> LENGTH: 359
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 100
ctaatacgac tcactatagg gcgactgtac agggtccgaa tataaaactt cat

```
ggttatgctg gtcatcttct atcagacact cgatgccttc cagccaaagt ggaccctgga    120
cgctagtctc attggcactg taccgggatt aggcttcagg ccacgcccac cgctgtctaa    180
catcgactca acactcatct atttcaaggt atctaagccg ttagtgtata tgttatatta    240
tagcgctctt tgttatgtgg aaagacgcca gggcgcgtat ctatatggtg gttttcatac    300
caaccgtggg aacctcgccc tatagtgagt cgtattag                            338

<210> SEQ ID NO 103
<211> LENGTH: 311
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 103
ctaatacgac tcactatagg gcgaaatggt ttctgctacc tgtgaggata gtatgcggga     60
tgcttgtatt cgttttcttg cctcgaaagt caatctcaaa gcgcttgaca gtgagacaga    120
gcttatgctc attgaagagg ccggcaaagt ggcagccctc gtcggtggag aggagtttgt    180
gctgctggtt aagctcctca attcattaaa ggtagattgt acattttggc gtcttctcga    240
acaagttaga atctatttag caaagtgcca atgtatcagc ttccaattcg ccctatagtg    300
agtcgtatta g                                                         311

<210> SEQ ID NO 104
<211> LENGTH: 325
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 104
ctaatacgac tcactatagg gcgatggcta attaatagta ggccgaagaa ctttttgagt     60
ggcctcgata tgtccgacgt tgtggcttcg tgggaggttc ctttggttgg ccaagcttac    120
cgagtcgaat tcgaacacgg aagtgcaacg ggtaaacgtt ttgtgtacgt taatggactc    180
gaggtgttac gaaaacactg gcttttaag cttgttggcg aggaaagctt tgacatattg     240
ggacataagt gcatcatttc tatcaaagcc gtaggaggct tcaggttggt agcaaactcc    300
atcgccctat agtgagtcgt attag                                          325

<210> SEQ ID NO 105
<211> LENGTH: 311
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 105
ctaatacgac tcactatagg gcgaagccgg cttcttcttc cttggcatgc acgattacac     60
gaaatgcttc cattgcgacg gcggtctgtg taattgggag acaggtgacg acccctgggt    120
agagcatgcc cgctggttcc ctgaatgtca attcgttcag ctaagcaagg gcggagcatt    180
catcgctgag tgccaacaac gtcacgaaaa actagttaat ggcgcggtag cccaggcaga    240
acttcaggct tttagtgaag tagaaccggg aggaacaggc agtgacttcg ccctatagtg    300
agtcgtatta g                                                         311
```

```
<210> SEQ ID NO 106
<211> LENGTH: 330
<212> TYPE: DNA
<213> ORGANISM: Artificial sequence
<220> FEATURE:
<223> OTHER INFORMATION: A double stranded RNA expressing construct
      targeting a Varroa gene

<400> SEQUENCE: 106
ctaatacgac tcactatagg gcgattccgc ttcatttgag aactgagctt gaagaaataa      60
tgcagtcgcc cgtcgtcaag ttctacctcg agaaaggtgt accgaaacaa gtgattcgaa     120
tgaccgtaaa aaatatatgc ttgacaacga gcgcggtttc cgtgatcttg acgaaattac     180
acacgtactc ggacaggtgc tcagcttcgg caacaagaag actgcgcctg ccaatgaaaa     240
aggtaggtgg ataccggata tttgtcggga attcaatgca gctgaacccg atgaggttga     300
ttcagatcgc cctatagtga gtcgtattag                                      330

<210> SEQ ID NO 107
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 107
ctaatacgac tcactatagg gcgaatggag aacatcgcac ag                         42

<210> SEQ ID NO 108
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 108
ctaatacgac tcactatagg gcgattccag tacgttatgt tgctc                      45

<210> SEQ ID NO 109
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 109
ctaatacgac tcactatagg gcgaggtctt gacaacacat gctac                      45

<210> SEQ ID NO 110
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 110
ctaatacgac tcactatagg gcgactcagc agaaatgatc gg                         42

<210> SEQ ID NO 111
<211> LENGTH: 42
<212> TYPE: DNA
<213> ORGANISM: Artificial sequence
<220> FEATURE:
<223> OTHER INFORMATION: Single strand DNA oligonucleotide
```

```
<400> SEQUENCE: 111
ctaatacgac tcactatagg gcgaaacgct gtgcttcacg ta                    42

<210> SEQ ID NO 112
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 112
ctaatacgac tcactatagg gcgatcacga gtaatctcca cga                   43

<210> SEQ ID NO 113
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 113
ctaatacgac tcactatagg gcgatcagat gattggaacg ga                    42

<210> SEQ ID NO 114
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 114
ctaatacgac tcactatagg gcgaaacagg tcttcaaaca gcag                  44

<210> SEQ ID NO 115
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 115
ctaatacgac tcactatagg gcgatcaatt cgtctgcaga tctc                  44

<210> SEQ ID NO 116
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 116
ctaatacgac tcactatagg gcgacataaa tggcgataag cg                    42

<210> SEQ ID NO 117
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 117
ctaatacgac tcactatagg gcgaaatgag tgttgagcgc gg                    42

<210> SEQ ID NO 118
```

```
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 118
ctaatacgac tcactatagg gcgactccga tcatttggcg tt                              42

<210> SEQ ID NO 119
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 119
ctaatacgac tcactatagg gcgaaggtga catccgtgtt cg                              42

<210> SEQ ID NO 120
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 120
ctaatacgac tcactatagg gcgaatgaag acatataggg tcgct                           45

<210> SEQ ID NO 121
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 121
ctaatacgac tcactatagg gcgactgtac agggtccgaa tataaa                          46

<210> SEQ ID NO 122
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 122
ctaatacgac tcactatagg gcgattcgag tttctcaaag gttg                            44

<210> SEQ ID NO 123
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 123
ctaatacgac tcactatagg gcgacaattg aatatggacg tcactc                          46

<210> SEQ ID NO 124
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 124
```

```
ctaatacgac tcactatagg gcgattgaaa gccagcagta aacg          44
```

<210> SEQ ID NO 125
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 125

```
ctaatacgac tcactatagg gcgacatcat cttcttcatc tgcttg        46
```

<210> SEQ ID NO 126
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 126

```
ctaatacgac tcactatagg gcgaggttcc cacggttggt at            42
```

<210> SEQ ID NO 127
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 127

```
ctaatacgac tcactatagg gcgaaatggt ttctgctacc tgtg          44
```

<210> SEQ ID NO 128
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 128

```
ctaatacgac tcactatagg gcgaattgga agctgataca ttgg          44
```

<210> SEQ ID NO 129
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 129

```
ctaatacgac tcactatagg gcgatggcta attaatagta ggccg         45
```

<210> SEQ ID NO 130
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 130

```
ctaatacgac tcactatagg gcgatggagt ttgctaccaa cct           43
```

<210> SEQ ID NO 131
<211> LENGTH: 42
<212> TYPE: DNA

```
<213> ORGANISM: Artificial sequence
<220> FEATURE:
<223> OTHER INFORMATION: Single strand DNA oligonucleotide

<400> SEQUENCE: 131
ctaatacgac tcactatagg gcgaagccgg cttcttcttc ct                42

<210> SEQ ID NO 132
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 132
ctaatacgac tcactatagg gcgaagtcac tgcctgttcc tcc               43

<210> SEQ ID NO 133
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 133
ctaatacgac tcactatagg gcgattccgc ttcatttgag aac               43

<210> SEQ ID NO 134
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 134
ctaatacgac tcactatagg gcgatctgaa tcaacctcat cgg               43

<210> SEQ ID NO 135
<211> LENGTH: 52
<212> TYPE: DNA
<213> ORGANISM: Artificial sequence
<220> FEATURE:
<223> OTHER INFORMATION: Single strand DNA oligonucleotide

<400> SEQUENCE: 135
taatacgact cactataggg cgagccaaca cttgtcacta ctagaaagag aa     52

<210> SEQ ID NO 136
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 136
taatacgact cactataggg cgaaggtaat ggttgtctgg taaaggac          48

<210> SEQ ID NO 137
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 137
aaagggcagg tgcttatcaa                                         20
```

<210> SEQ ID NO 138
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 138
tgtccagggt cgagagtagc                                              20

<210> SEQ ID NO 139
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 139 accttttca aagaccgaac c                                             21

<210> SEQ ID NO 140
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 140
cgaagactcc gttcgaaaac                                              20

<210> SEQ ID NO 141
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 141
ctagttaatg gcgcggtagc                                              20

<210> SEQ ID NO 142
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 142
tcctcccggt tctacttcac                                              20

<210> SEQ ID NO 143
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 143
aatgccatca ttaccatcct g                                            21

<210> SEQ ID NO 144
<211> LENGTH: 20
<212> TYPE: DNA
<213> ORGANISM: Artificial sequence
<220> FEATURE:

-continued

```
<223> OTHER INFORMATION: Single strand DNA oligonucleotide

<400> SEQUENCE: 144
caaaaaccaa tcggcaatct                                              20

<210> SEQ ID NO 145
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 145
atctgcccac gtcagcgttt                                              20

<210> SEQ ID NO 146
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 146
gtccgtcatt tcggctttgg                                              20

<210> SEQ ID NO 147
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 147
aagtcgtacg agcttcccga c                                            21

<210> SEQ ID NO 148
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 148
acagggaggc aaggatggaa c                                            21
```

COMPOSITIONS FOR CONTROLLING *VARROA* MITES IN BEES

CROSS-REFERENCE TO RELATED APPLICATIONS AND INCORPORATION OF SEQUENCE LISTING

This application is continuation of U.S. patent application Ser. No. 14/606,328, filed Jan. 27, 2015, which is a continuation of U.S. patent application Ser. No. 13/446,557, filed Apr. 13, 2012, which is a continuation-in-part of International Application No. PCT/IL2010/000844, filed Oct. 14, 2010, which claims priority to U.S. Provisional Application No. 61/251,339, filed Oct. 14, 2009. All the foregoing applications are incorporated by reference in their entirety herein. A sequence listing contained in the file named "61440_Sequence_Listing.txt" which is 78,627 bytes in size (measured in MS-Windows®) and created on Apr. 24, 2017, is filed electronically herewith and incorporated by reference in its entirety.

FIELD AND BACKGROUND OF THE INVENTION

The invention relates to compositions for controlling *Varroa* mite infestation in bees.

Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor*.

Colony Collapse Disorder (CCD) of honeybees is threatening to annihilate U.S. and world agriculture. Indeed, in the recent outbreak of CCD in the U.S in the winter of 2006-2007, an estimated 25% or more of the 2.4 million honeybee hives were lost because of CCD. An estimated 23% of beekeeping operations in the United States suffered from CCD over the winter of 2006-2007, affecting an average of 45% of the beekeepers operations. In the winter of 2007-2008, the CCD action group of the USDA-ARS estimated that a total of 36% of all hives from commercial operations were destroyed by CCD.

CCD is characterized by the rapid loss from a colony of its adult bee population, with dead adult bees usually found at a distance from the colony. At the final stages of collapse, a queen is attended only by a few newly emerged adult bees. Collapsed colonies often have considerable capped brood and food reserves. The phenomenon of CCD was first reported in 2006; however, beekeepers noted unique colony declines consistent with CCD as early as 2004. Various factors such as mites and infectious agents, weather patterns, electromagnetic (cellular antennas) radiation, pesticides, poor nutrition and stress have been postulated as causes. To date, control of CCD has focused on *Varroa* mite control, sanitation and removal of affected hives, treating for opportunistic infections (such as *Nosema*) and improved nutrition. No effective preventative measures have been developed to date.

*Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality.

Current methods of treating *Varroa* infestations are proving to be ineffective as the mites develop resistance to existing miticides. In addition, the use of such miticides may introduce injurious chemicals into honey that is intended for human consumption.

U.S. Patent Application 20090118214 teaches the use of dsRNA for prevention and treatment of viral infections in honeybees.

SUMMARY OF THE INVENTION

According to an aspect of some embodiments of the present invention there is provided an isolated nucleic acid agent comprising a nucleic acid sequence which downregulates expression of a gene product of a *Varroa destructor* mite.

According to an aspect of some embodiments of the present invention there is provided a nucleic acid construct comprising a nucleic acid sequence encoding the isolated nucleic acid agent of the present invention.

According to an aspect of some embodiments of the present invention there is provided a bee-ingestible composition comprising at least one nucleic acid agent which comprises a nucleic acid sequence which downregulates expression of a gene product of a *Varroa destructor* mite.

According to an aspect of some embodiments of the present invention there is provided a method of preventing or treating a *Varroa destructor* mite infestation of a bee hive, the method comprising administering to the bee an effective amount of least one nucleic acid agent which comprises a nucleic acid sequence which downregulates expression of a gene product of a *Varroa destructor* mite, thereby preventing or treating a *Varroa destructor* mite infestation of a bee hive.

According to an aspect of some embodiments of the present invention there is provided a method of preventing or treating a *Varroa destructor* mite infestation of a bee hive, the method comprising administering to the bee an effective amount of the nucleic acid construct of the present invention, thereby preventing or treating a *Varroa destructor* mite infestation of a bee hive.

According to an aspect of some embodiments of the present invention there is provided a method of reducing the susceptibility of honeybees to Colony Collapse Disorder (CCD), the method comprising administering to the honeybee an effective amount of at least one double-stranded ribonucleic nucleic acid (dsRNA), the at least one dsRNA comprising a sequence complementary to at least 21 nucleotides of *Varroa destructor* mite mRNA and capable of inducing degradation of the *Varroa destructor*-specific mRNA.

According to some embodiments of the invention, the nucleic acid sequence is complementary to at least 21 nucleotides of *Varroa destructor* mite specific RNA and capable of inducing degradation of the *Varroa destructor* mite RNA.

According to some embodiments of the invention, the agent is selected from the group consisting of a dsRNA, an antisense RNA and a ribozyme.

According to some embodiments of the invention, the dsRNA is selected from the group consisting of siRNA, shRNA and miRNA.

According to some embodiments of the invention, the gene product is an mRNA encoding a polypeptide selected from the group consisting of ATPase subunit A, RNA polymerase I, RNA polymerase III, Inhibitor of apoptosis (IAP), FAS apoptotic inhibitor and α-Tubulin.

According to some embodiments of the invention, the at least one nucleic acid agent comprises at least five nucleic acid agents, for down-regulating ATPase subunit A, RNA polymerase III, Inhibitor of apoptosis (IAP), FAS apoptotic inhibitor and α-Tubulin, each of the at least five nucleic acid agent targeting a different gene.

According to some embodiments of the invention, the at least one nucleic acid agent comprises at least six nucleic acid agents, for down-regulating ATPase subunit A, RNA polymerase I, RNA polymerase III, Inhibitor of apoptosis (IAP), FAS apoptotic inhibitor and α-Tubulin, each of the at least six nucleic acid agents for targeting a different gene.

According to some embodiments of the invention, the nucleic acid agents are as set forth in SEQ ID Nos: 1, 13, 27, 30 and 39.

According to some embodiments of the invention, the nucleic acid agents are as set forth in SEQ ID Nos: 93, 96, 100, 104 and 106.

According to some embodiments of the invention, the nucleic acid agents are as set forth in SEQ ID Nos: 1, 4, 7, 10, 13, 16, 19, 22, 25, 27, 30, 33, 36 and 39.

According to some embodiments of the invention, the nucleic acid agents are as set forth in SEQ ID Nos: 93-106.

According to some embodiments of the invention, the nucleic acid sequence is greater than 15 base pairs in length.

According to some embodiments of the invention, the nucleic acid sequence is 19 to 25 base pairs in length.

According to some embodiments of the invention, the nucleic acid sequence is greater than 30 base pairs in length.

According to some embodiments of the invention, the composition is in solid form.

According to some embodiments of the invention, the composition is in liquid form.

According to some embodiments of the invention, the composition comprises protein.

According to some embodiments of the invention, the protein is in the form of pollen and/or soy patties.

According to some embodiments of the invention, the liquid is a sucrose solution.

According to some embodiments of the invention, the liquid is a corn syrup solution.

According to some embodiments of the invention, the liquid further comprises a carbohydrate or sugar supplement.

According to some embodiments of the invention, the bee is a honeybee.

According to some embodiments of the invention, the honeybee is a forager.

According to some embodiments of the invention, the honeybee is a hive bee.

According to some embodiments of the invention, the honeybee is a bee of a colony, and wherein the administering reduces the susceptibility of the bee colony to Colony Collapse Disorder.

According to some embodiments of the invention, the administering is effected by feeding.

According to some embodiments of the invention, the feeding comprises providing a liquid bee-ingestible composition.

According to some embodiments of the invention, the feeding comprises providing a solid bee-ingestible composition.

According to some embodiments of the invention, the *Varroa destructor* mite mRNA encodes a polypeptide selected from the group consisting of NADH dehydrogenase subunit 2, ATP synthetase subunit 8, ATP synthetase subunit 6, sodium channel and cytochrome oxydase subunit I.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9A-9C are graphs representing the means (±SE) of results of real-time RT-PCR of *Varroa* RNA with probes for *Varroa* gene mRNA: RNA polymerase III (9A, probes SEQ ID NOs. 137 and 138), IAP1 and IAP2 (9B, probes SEQ ID NOs. 141 and 142) and vacuolar proton ATPase (9C, probes SEQ ID NOs. 139 and 140), respectively. The *Varroa* RNA was extracted from mites infesting bees fed a mixture of 5 *Varroa*-specific dsRNAs (Mixture I), or from mites infesting bees fed a mixture of 14 *Varroa*-specific dsRNAs (Mixture II). Controls represent *Varroa* RNA extracted from mites infesting untreated bees or mites infesting bees fed irrelevant (GFP) dsRNA. FIGS. 9D-9F are photographs showing semi-quantitative RT-PCR of *Varroa* RNA illustrating specific silencing of *Varroa* apoptosis inhibitor FAS gene expression in mites infesting bees fed on *Varroa*-specific dsRNA. Apoptosis inhibitor FAS RNA was amplified (using primers SEQ ID NOs. 145 and 146) in *Varroa* RNA extracted from mites infesting bees fed a mixture of 5 *Varroa*-specific dsRNAs (9D, Mixture I), or from mites infesting bees fed a mixture of 14 *Varroa*-specific dsRNAs (9D, Mixture II). Controls represent amplification of Apoptosis inhibitor FAS RNA in *Varroa* RNA extracted from mites infesting untreated bees (9E, Untreated) or mites infesting bees fed irrelevant (9E, dsRNA-GFP) dsRNA. 9F is a control showing amplification of the housekeeping gene actin (using primers SEQ ID NOs. 147 and 148). Numbers indicate the number of cycles of amplification. –RT reactions serve as controls for DNA contamination. Note strong silencing of Apoptosis inhibitor FAS expression in mites infesting bees fed Mixture I or Mixture II (FIG. 9D);

DESCRIPTION OF EMBODIMENTS OF THE INVENTION

The present invention, in some embodiments thereof, relates to methods and compositions for reducing the susceptibility of bees to *Varroa* mite infestation.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Bees are susceptible to a myriad of viral infections. Treatment of such infections by down-regulation of a particular viral gene product has shown to be successful in eliminating virally induced infections in the bee (see U.S. Patent Application 20090118214).

The present inventors now propose treatment of *Varroa* mite infestations in bees by down-regulating particular *Varroa* mite gene products.

*Varroa* mites parasitize pupae and adult bees and reproduce in the pupal brood cells. The mites use their mouths to puncture the exoskeleton and feed on the bee's hemolymph. The present inventors unexpectedly found that polynucleotide agents administered to the bees to treat *Varroa* mite infestations presented in the bee's hemolymph thereby becoming available to the mite.

Figure 4:
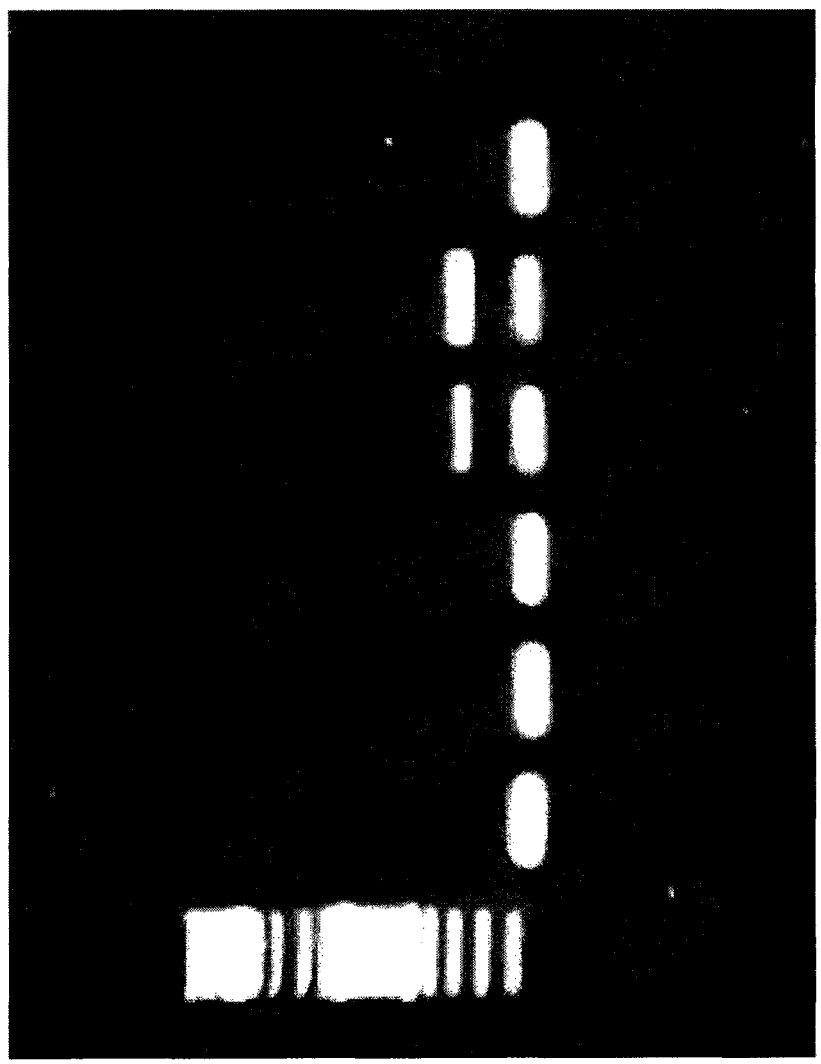
FIG. 4 is a photograph illustrating RT-PCR of *Varroa* RNA with primers to apoptosis inhibitor protein (IAP; sequence 27). M: size markers. Lanes 1-3: Template RNA of *Varroa* from hives treated with dsRNA of sequences 27. Lane 4: Template RNA of *Varroa* from control hives. Lane 5: Positive control (a IAP-carrying plasmid). Lane 6: Negative control (no template).
Figure 5:
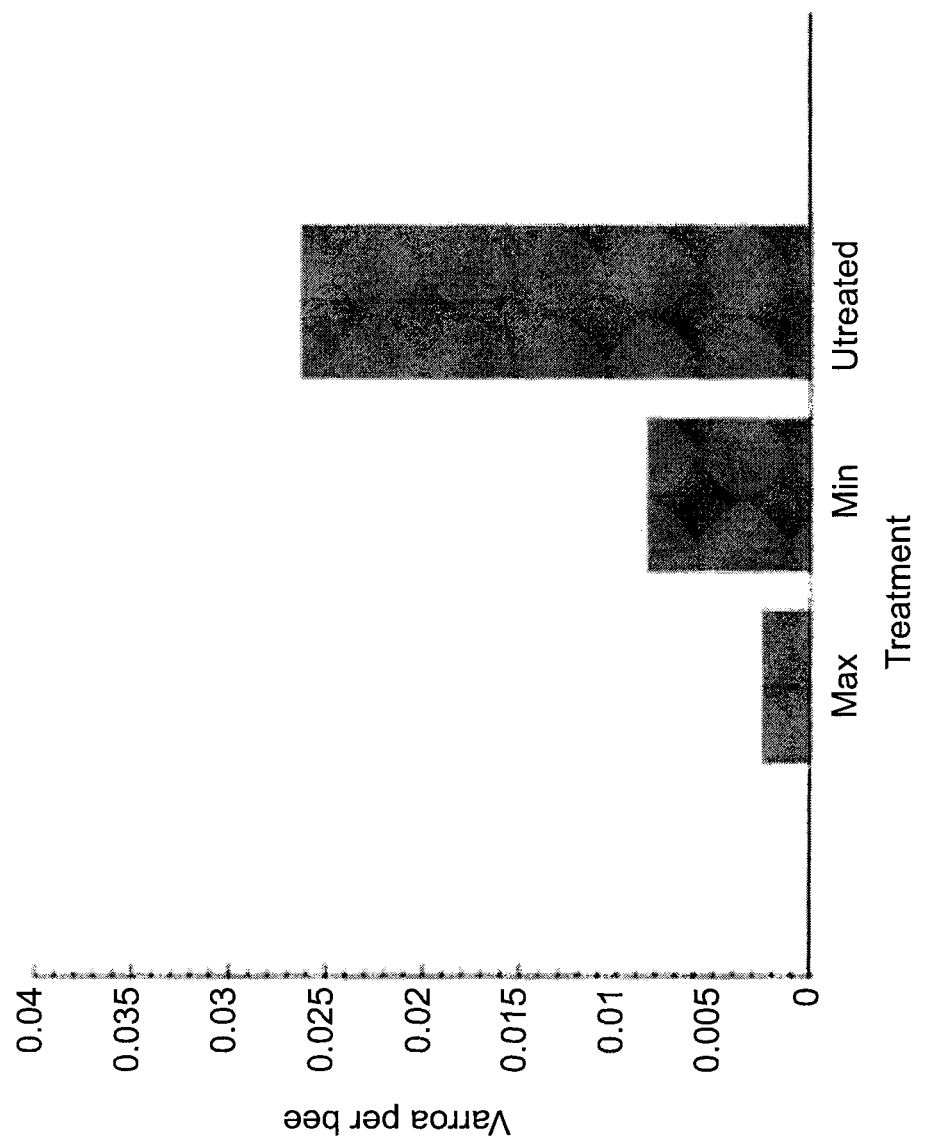
FIG. 5 is a bar graph illustrating the *Varroa* count per bee (adult bees plus larvae inside sealed cells) in control hives and in hives treated with dsRNA mixture I (Min) and with dsRNA mixture II (Max).
Figure 11:
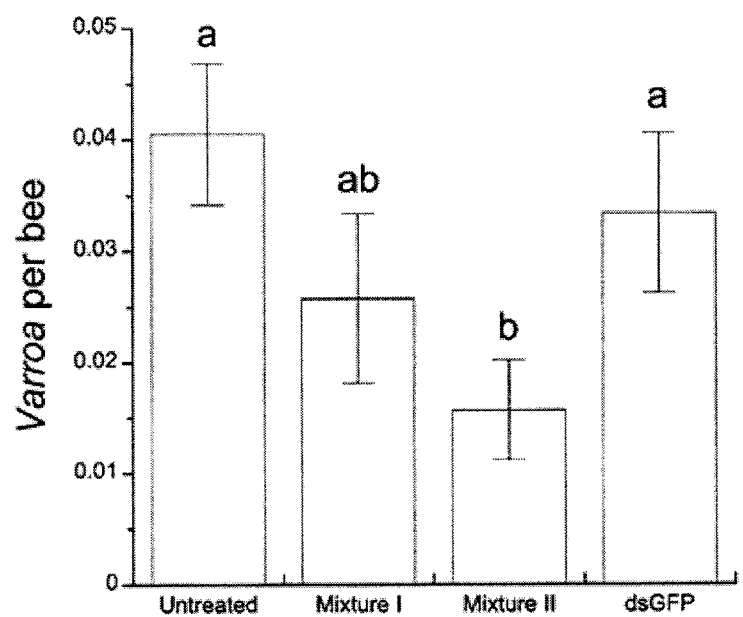
FIG. 11 is a graph showing *Varroa* infestation (number of mites) in treated bees and controls (as in FIG. 10), indicating significant reduction in susceptibility to *Varroa* infestation following feeding of the bees with Mixture I or Mixture II.

The present inventors have shown that dsRNA can successfully be transferred to Vorroa mites (FIGS. 2A-E, 6 and 7), that the dsRNA can serve to down-regulate expression of a particular gene in the *Varroa* mite (FIGS. 4 and 9A-9E) and further that targeting of particular genes for down-regulation can result in a reduction in the number of *Varroa* mites (FIGS. 5 and 11). Yet further, the present inventors have shown that RNA sequences transferred to mites from bees fed dsRNA can be transferred back to untreated, "naïve" bees via *Varroa* infestation (FIG. 7).

Thus, according to one aspect of the present invention there is provided a method of preventing or treating a *Varroa destructor* mite infestation of a bee, the method comprising administering to the bee an effective amount of a nucleic acid agent comprising a nucleic acid sequence which down-regulates expression of a gene product of a *Varroa destructor* mite, thereby preventing or treating a *Varroa destructor* mite infestation of a bee.

As used herein, the term "bee" refers to both an adult bee and pupal cells thereof. According to one embodiment, the bee is in a hive.

An adult bee is defined as any of several winged, hairy-bodied, usually stinging insects of the superfamily Apoidea in the order Hymenoptera, including both solitary and social species and characterized by sucking and chewing mouth-parts for gathering nectar and pollen. Exemplary bee species include, but are not limited to, *Apis, Bombus, Trigona, Osmia* and the like. In one embodiment, bees include, but are not limited to bumblebees (*Bombus terrestris*), honey-bees (*Apis mellifera*) (including foragers and hive bees) and *Apis cerana*.

According to one embodiment, the bee is part of a colony.

The term "colony" refers to a population of bees comprising dozens to typically several tens of thousand bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

According to this aspect of the present invention the agents of the present invention are used to prevent the *Varroa destructor* mite from living as a parasite on the bee, or larvae thereof.

The phrase "*Varroa destructor* mite" refers to the external parasitic mite that attacks honey bees *Apis cerana* and *Apis mellifera*. The mite may be at an adult stage, feeding off the bee, or at a larval stage, inside the honey bee brood cell.

As mentioned, the agents of the present invention are capable of downregulating expression of a gene product of a *Varroa destructor* mite.

As used herein, the phrase "gene product" refers to an RNA molecule or a protein.

According to one embodiment, the *Varroa destructor* mite gene product is one which is essential for mite viability. Down-regulation of such a gene product would typically result in killing of the *Varroa* mite. According to another embodiment, the *Varroa destructor* mite gene product is one which is essential for mite reproduction. Down-regulation of such a gene product would typically result in the prevention of reproduction of the *Varroa* mite and the eventual extermination of the mite population. According to yet another embodiment, the *Varroa destructor* mite gene product is one which is required to generate pathogenic symptoms in the bee.

Exemplary gene products that may be down-regulated according to this aspect of the present invention include, but are not limited to NADH dehydrogenase; subunit 2—Genbank accession NC_004454; ATP synthetase; subunit 8—NC_004454; ATP synthetase; subunit 6—NC_004454; sodium channel gene—Genbank accession No. FJ216963; Cytochrome oxydase subunit I—Genbank accession No. EF025469.

It will be appreciated that whilst the agents of the present invention are capable of downregulating expression of a gene product of a *Varroa destructor* mite, it is preferable that they downregulate to a lesser extent expression of the gene product in other animals, such as the bee. Accordingly, the agents of the present invention must be able to distinguish between the mite gene and the bee gene, down-regulating the former to a greater extent than the latter. According to another embodiment the agents of the present invention do not down-regulate the bee gene whatsoever. This may be effected by targeting a gene that is expressed differentially in the mite and not in the bee e.g. the mite sodium channel gene—FJ216963. Alternatively, the agents of the present invention may be targeted to mite-specific sequences of a gene that is expressed both in the mite and in the bee.

According to one embodiment the agents of the present invention target segments of *Varroa* genes that are at least 100 bases long and do not carry any sequence longer than 19 bases that is entirely homologous to any bee-genome sequence or human-genome sequence.

Examples of such gene segments are provided herein below:

SEQ ID NO: 1. *Varroa* gene homologous to ATPase subunit A (segment 1); SEQ ID NO: 2. *Varroa* gene homologous to ATPase subunit A (segment 2); SEQ ID NO: 3. *Varroa* gene homologous to ATPase subunit A (segment 3); SEQ ID NO: 4. *Varroa* gene homologous to ATPase subunit A (segment 4); SEQ ID NO: 5. *Varroa* gene homologous to ATPase subunit A (segment 5); SEQ ID NO: 6. *Varroa* gene homologous to ATPase subunit A (segment 6); SEQ ID NO: 7. *Varroa* gene homologous to ATPase subunit A (segment 7); SEQ ID NO: 8. *Varroa* gene homologous to ATPase subunit A (segment 8); SEQ ID NO: 9. *Varroa* gene homologous to ATPase subunit A (segment 9); SEQ ID NO: 10. *Varroa* gene homologous to RNA polymerase I (segment 1); SEQ ID NO: 11. *Varroa* gene homologous to RNA polymerase I (segment 2); SEQ ID NO: 12. *Varroa* gene homologous to RNA polymerase I (segment 3); SEQ ID NO: 13. *Varroa* gene homologous to RNA polymerase III (segment 1); SEQ ID NO: 14. *Varroa* gene homologous to RNA polymerase III (segment 2); SEQ ID NO: 15. *Varroa* gene homologous to RNA polymerase III (segment 3); SEQ ID NO: 16. *Varroa* gene homologous to RNA polymerase III (segment 4); SEQ ID NO: 17. *Varroa* gene homologous to RNA polymerase III (segment 5); SEQ ID NO: 18. *Varroa* gene homologous to RNA polymerase III (segment 6); SEQ ID NO: 19. *Varroa* gene homologous to RNA polymerase III (segment 7) SEQ ID NO: 20. *Varroa* gene homologous to RNA polymerase III (segment 8); SEQ ID NO: 21. *Varroa* gene homologous to RNA polymerase III (segment 9); SEQ ID NO: 22. *Varroa* gene homologous to Inhibitor of apoptosis (IAP; segment 1); SEQ ID NO: 23. *Varroa* gene homologous to Inhibitor of apoptosis (IAP; segment 2); SEQ ID NO: 24. *Varroa* gene homologous to Inhibitor of apoptosis (IAP; segment 3); SEQ ID NO: 25. *Varroa* gene homologous to Inhibitor of apoptosis (IAP; segment 4); SEQ ID NO: 26. *Varroa* gene homologous to Inhibitor of apoptosis (IAP; segment 5); SEQ ID NO: 27. *Varroa* gene homologous to Inhibitor of apoptosis (IAP; segment 6); SEQ ID NO: 28. *Varroa* gene homologous to Inhibitor of apoptosis (IAP; segment 7); SEQ ID NO: 29. *Varroa* gene homologous to Inhibitor of apoptosis (IAP; segment 8); SEQ ID NO: 30. *Varroa* gene homologous to FAS apoptotic inhibitor (segment 1); SEQ ID NO: 31. *Varroa* gene homologous to FAS apoptotic inhibitor (segment 2); SEQ ID NO: 32. *Varroa* gene homologous to FAS apoptotic inhibitor (segment 3); SEQ ID NO: 33. Varoa gene homologous to α-Tubulin (segment 1); SEQ ID NO: 34. Varoa gene homologous to α-Tubulin (segment 2); SEQ ID NO: 35. Varoa gene homologous to α-Tubulin (segment 3); SEQ ID NO: 36. Varoa gene homologous to α-Tubulin (segment 4); SEQ ID NO: 37. Varoa gene homologous to α-Tubulin (segment 5); SEQ ID NO: 38. Varoa gene homologous to α-Tubulin (segment 6); SEQ ID NO: 39. Varoa gene homologous to α-Tubulin (segment 7); SEQ ID NO: 40. Varoa gene homologous to α-Tubulin (segment 8); SEQ ID NO: 41. Varoa gene homologous to α-Tubulin (segment 9); SEQ ID NO: 42.NADH dehydrogenase; subunit 2 (NC_004454): bases 709 to 974; SEQ ID NO: 43. ATP synthetase; subunit 8 (NC_004454): bases 3545 to 3643; SEQ ID NO: 44. Sodium channel protein (AY259834): bases 3336-3836.

Additional examples of sequences representing target *Varroa* gene segments include, but are not limited to the nucleic acid sequences of *Varroa* genes flanked by T7 promoter sequences in the following sequences (length of *Varroa*-specific sequence is indicated in parentheses):

SEQ ID NO: 93—*Varroa* gene homologous to α-tubulin (411 bases); SEQ ID NO: 94—*Varroa* gene homologous to α-tubulin (277 bases); SEQ ID NO: 95—*Varroa* gene homologous to α-tubulin (329 bases); SEQ ID NO: 96—*Varroa* gene homologous to RNA polymerase III (380 bases); SEQ ID NO: 97—*Varroa* gene homologous to RNA polymerase III (426 bases); SEQ ID NO: 98—*Varroa* gene homologous to RNA polymerase II (366 bases); SEQ ID NO: 99—*Varroa* gene homologous to RNA polymerase I (324 bases); SEQ ID NO: 100—*Varroa* gene homologous to vacuolar translocating ATPase (311 bases); SEQ ID NO: 101—*Varroa* gene homologous to vacuolar proton ATPase (210 bases); SEQ ID NO: 102—*Varroa* gene homologous to Na+/K+ ATPase (307 bases); SEQ ID NO: 103—*Varroa* gene homologous to apoptosis inhibitor IAP (263 bases); SEQ ID NO: 104—*Varroa* gene homologous to apoptosis inhibitor FAS (277 bases); SEQ ID NO: 105—*Varroa* gene homologous to apoptosis inhibitor IAP 1 and IAP2 (263 bases); SEQ ID NO: 106—*Varroa* gene homologous to apoptosis inhibitor IAP 1 and IAP2, reverse orientation (282 bases).

It will be appreciated that more than one gene may be targeted in order to maximize the cytotoxic effect on the *Varroa* mites.

Thus, according to one embodiment, the following group of genes are targeted—ATPase subunit A, RNA polymerase III, Inhibitor of apoptosis (IAP), FAS apoptotic inhibitor and α-Tubulin (e.g. using nucleic acid agents having the sequence as set forth in 1, 13, 27, 30 and 39, or nucleic acid agents having the sequence as set forth in SEQ ID Nos. 93, 96, 100, 104 and 106).

According to another embodiment, the following group of genes are targeted—ATPase subunit A, RNA polymerase I, RNA polymerase III, Inhibitor of apoptosis (IAP), FAS apoptotic inhibitor and α-Tubulin.

It will be appreciated that as well as down-regulating a number of genes, the present invention further contemplates using a number of agents to down-regulate the same gene (e.g. a number of dsRNAs each hybridizing to a different segment of the same gene). Thus, for example, the present inventors showed maximal cytotoxic activity when the following mixture of dsRNAs was used: SEQ ID Nos:1, 4, 7, 10, 13, 16, 19, 22, 25, 27, 30, 33, 36 and 39, or SEQ ID Nos. 93-106 and less of a cytotoxic activity when the following mixture of dsRNAs was used: SEQ ID Nos: 1, 13, 27, 30 and 39, or SEQ ID Nos. 93, 96, 100, 104 and 106.

Tools which are capable of identifying species-specific sequences may be used for this purpose—e.g. BLASTN and other such computer programs.

As used herein, the term "downregulating expression" refers to causing, directly or indirectly, reduction in the transcription of a desired gene, reduction in the amount, stability or translatability of transcription products (e.g. RNA) of the gene, and/or reduction in translation of the polypeptide(s) encoded by the desired gene.

Downregulating expression of a gene product of a *Varroa destructor* mite can be monitored, for example, by direct detection of gene transcripts (for example, by PCR), by detection of polypeptide(s) encoded by the gene or bee pathogen RNA (for example, by Western blot or immunoprecipitation), by detection of biological activity of polypeptides encode by the gene (for example, catalytic activity, ligand binding, and the like), or by monitoring changes in the Vaarroa destructor mite (for example, reduced proliferation of the mite, reduced virulence of the mite, reduced motility of the mite etc) and by testing bee infectivity/pathogenicity.

Downregulation of a *Varroa destructor* mite gene product can be effected on the genomic and/or the transcript level using a variety of agents which interfere with transcription and/or translation (e.g., RNA silencing agents, Ribozyme, DNAzyme and antisense).

According to one embodiment, the agent which down-regulates expression of a *Varroa destructor* mite gene product is a polynucleotide agent, such as an RNA silencing agent According to this embodiment, the polynucleotide agent is greater than 15 base pairs in length.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene or bee pathogen RNA sequence. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

According to one embodiment, the dsRNA is greater than 30 bp. The use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

Another method of downregulating a *Varroa* mite gene product is by introduction of small inhibitory RNAs (siRNAs).

The term "siRNA" refers to small inhibitory RNA duplexes (generally between 18-30 basepairs, between 19 and 25 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (SEQ ID NO: 4; Brummelkamp, T. R. et al. (2002) Science 296: 550) and 5'-UUUGUGUAG-3' (SEQ ID NO: 5; Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

In one embodiment of the present invention, synthesis of RNA silencing agents suitable for use with the present invention can be effected as follows. First, the *Varroa* mite target mRNA is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, bee, mouse, rat etc.) using any sequence alignment software, such as the BLAST software available from the NCBI server (wwwdotncbidotn-lmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene or bee pathogen target sequence.

For example, a siRNA that may be used in this aspect of the present invention is one which targets a mite-specific gene. Exemplary siRNAs are provided in SEQ ID NOs: 45-47.

SEQ ID NO: 45:
attttattcaattaaagtatt

SEQ ID NO: 46:
atacctcaaatgtatccttca

SEQ ID NO: 47:
ggccaatcccgattccggcga

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cystein residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

Another agent capable of downregulating a *Varroa* mite gene product is a DNAzyme molecule capable of specifically cleaving an mRNA transcript or DNA sequence of the bee pathogen polypeptide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Downregulation of Varrao mite gene products can also be effected by using an antisense polynucleotide capable of specifically hybridizing with an mRNA transcript encoding the *Varroa* mite gene product.

Design of antisense molecules which can be used to efficiently downregulate a Varrao mite gene product must be effected while considering two aspects important to the antisense approach. The first aspect is delivery of the oligonucleotide into the cytoplasm of the appropriate cells, while the second aspect is design of an oligonucleotide which specifically binds the designated mRNA or RNA target sequence within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

Enhanced delivery of the invention oligomers can also be mediated by the use of (i) viruses such as Sendai virus or adenovirus; (ii) polyamine or polycation conjugates using compounds such as polylysine, protamine or N1, N12-bis (ethyl)spermine; (iii) lipopolyamine complexes using compounds such as lipospermine; (iv) anionic, neutral or pH sensitive lipids using compounds including anionic phospholipids such as phosphatidyl glycerol, cardiolipin, phosphatidic acid or phosphatidylethanolamine; (v) conjugates with compounds such as transferrin or biotin or (vi) conjugates with compounds such as serum proteins (including albumin or antibodies), glycoproteins or polymers (including polyethylene glycol) that enhance pharmacokinetic properties of oligomers in a subject. Any reagent such as a lipid or any agent such as a virus that can be used in transfection protocols is collectively referred to herein as a "permeation enhancing agent".

The oligomer active ingredient is generally combined with a carrier such as a diluent or excipient which can include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations. Preparations of oligomer complex with cationic lipid (such as Lipofectin™) were thus capable of delivering oligomers.

The use of antisense oligodeoxyribonucleotides (ODN) is a potential method to switch off gene expression. The poor cellular uptake of ODN in primary cells still is a limiting factor that may contribute to the lack of functional efficacy. Various forms of cationic lipids have been developed for efficient delivery of nucleic acids into different types of cells.

One of the most promising approach is the use of lipid-based carrier systems such as liposomes. Liposomes are microscopic closed vesicles composed of bilayered phospholipid membranes surrounding aqueous spaces in which drugs can be entrapped. Successful cellular delivery and enhancement of specific antisense activity have been demonstrated by some laboratories with different liposomal preparations such as conventional liposomes, cationic liposomes, pH-sensitive liposomes, and immunoliposomes.

A persisting fly in the antisense ointment, however, is the physical as well as the physiological challenge of ensuring that the stuff reaches its target. How to get the highly charged, often fragile and—in comparison to traditional pharmacological agents—complex molecules inside the tissue of interest is a vexing problem. When "naked" antisense ODN are given intravenously, the hepatic first-pass destruction is considerable, and deposition in kidney cells for example is characterized by an efficiency of less than 2%. And while packaging the antisense ODN within a lipid carrier material such as lipofectin improves transfer characteristics, the results nevertheless remain suboptimal. Furthermore, lipofectin per se may exhibit untoward effects. For these reasons, viruses have often become the method of choice when it comes to introducing genetic material, including complete genes, into cells.

Antisense oligonucleotides have been covalently attached to asialoglycoprotein (ASGP) via disulfide bond conjugation chemistry. The molecular congjugates were used to deliver antisense oligonucleotides complementary to the mRNA of the interleukin 6 signal transduction protein (gp130) to modulate the acute phase response of hepatoma (HepG2) cells in vitro. The level of inhibition was comparable to that found with previous technology featuring noncovalent complexes of ASGP-poly(L-lysine) (ASGP-PLL) and oligonucleotide. Addition of ASGP-PLL reduced the effective dose of antisense oligonucleotides relative to unconjugated antisense by 10-fold.

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating a *Varroa* mite gene product is a ribozyme molecule capable of specifically cleaving an mRNA transcript encoding the *Varroa* mite gene product.

Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA, including viral RNA, has rendered them valuable tools in both basic research and therapeutic applications.

An additional method of downregulating the expression of a *Varroa* mite gene product in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| | | | | |
|---|---|---|---|---|
| oligo | 3'--A | G | G | T |
| duplex | 5'--A | G | C | T |
| duplex | 3'-T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression.

Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

The polynucleotide down-regulating agents of the present invention may be generated according to any polynucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The polynucleotide agents of the present invention may comprise heterocylic nucleosides consisting of purines and the pyrimidines bases, bonded in a 3' to 5' phosphodiester linkage.

Preferably used polynucleotide agents are those modified in either backbone, internucleoside linkages or bases, as is broadly described hereinunder.

Specific examples of preferred polynucleotide agents useful according to this aspect of the present invention include polynucleotide agents containing modified backbones or non-natural internucleoside linkages. Polynucleotide agents having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified polynucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other polynucleotide agents which can be used according to the present invention, are those modified in both sugar and the internucleoside linkage, i.e., the backbone, of the nucleotide units are replaced with novel groups. The base units are maintained for complementation with the appropriate polynucleotide target. An example for such an polynucleotide mimetic, includes peptide nucleic acid (PNA). A PNA polynucleotide refers to a polynucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Polynucleotide agents of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Following synthesis, the polynucleotide agents of the present invention may optionally be purified. For example, polynucleotides can be purified from a mixture by extraction with a solvent or resin, precipitation, electrophoresis, chromatography, or a combination thereof. Alternatively, polynucleotides may be used with no, or a minimum of, purification to avoid losses due to sample processing. The polynucleotides may be dried for storage or dissolved in an aqueous solution. The solution may contain buffers or salts to promote annealing, and/or stabilization of the duplex strands.

It will be appreciated that a polynucleotide agent of the present invention may be provided per se, or as a nucleic acid construct comprising a nucleic acid sequence encoding the polynucleotide agent.

Typically, the nucleic acid construct comprises a promoter sequence which is functional in the host cell, as detailed herein below.

The polynucleotide sequences of the present invention, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

It will be appreciated that the nucleic acid agents can be delivered to the *Varroa* mites in a great variety of ways.

According to one embodiment, the nucleic acid agents are delivered directly to the mites (e.g. by spraying an infested hive). The nucleic acid agents, or constructs encoding same may enter the mites bodies by diffusion. In this embodiment, the promoter of the nucleic acid construct is typically operational in mite cells.

It will be appreciated that since *Varroa* mites use their mouths to puncture the bee exoskeleton and feed on the bee's hemolymph, the present invention contemplates delivering the polynucleotide agents of the present invention to the bees, whereby they become presented in the bee's hemolymph thereby becoming available to the mite. Thus, according to another embodiment, the nucleic acid agents are delivered indirectly to the mites (e.g. via the bee). In this embodiment, the promoter of the nucleic acid construct is typically operational in bee cells.

According to one embodiment, the nucleic acid agents are delivered to the bees by spraying. The nucleic acid agents, or constructs encoding same may enter the bees bodies by diffusion.

According to another embodiment, the nucleic acid agents are delivered to the bees via its food. The present inventors consider that following ingestion of the nucleic acid agents of the present invention, the agents will be presented in the bee's hemolymph, whereby it becomes available to the *Varroa* mite.

Thus the polynucleotides of the present invention may be synthesized in vitro and added to the food. For example double stranded RNA may be synthesized by adding two opposing promoters (e.g. T7 promoters; SEQ ID NOs: 48 and 49) to the ends of the gene segments, wherein SEQ ID NO: 48 is placed immediately 5' to the gene and SEQ ID NO: 49 is placed immediately 3' to the gene segment. The dsRNA may then be transcribed in vitro with the T7 RNA polymerase.

Exemplary sequences for synthesizing dsRNA according to embodiments of the present invention are provided in SEQ ID NOs: 50-91 and 93-106.

Exemplary primers for synthesizing dsRNA, according to embodiments of the present invention are provided in SEQ ID NOs: 107-134 (each pair represents a forward and a reverse primer, see Table 1 in the Examples section).

As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. The last two can be supplied only as a liquid to bees.

Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one embodiment, pan or trays in which floating supports-such as wood chips, cork, or plastic sponge-are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413).

It will be appreciated that Varro mites cause wound sites in the exoskeleton of bees. Such wound sites harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections.

Thus, by killing the mites (or preventing reproduction thereof), the agents of the present invention may be used to prevent and/or treat bacterial infections such as Melissococcus pluton and viral infections caused by the above named viruses.

Since *Varroa* mite infestation and viral infections are thought to be responsible for colony collapse disorder (CCD), the present agents may also be used to prevent or reduce the susceptibility of a bee colony to CCD.

It will be appreciated that in addition to feeding of oligonucleotides and/or polynucleotides for reduction of the bee pathogen infection and infestation, enforcement of proper sanitation (for example, refraining from reuse of infested hives) can augment the effectiveness of treatment and prevention of infections.

It is expected that during the life of a patent maturing from this application many relevant methods for downregulating expression of gene products will be developed and the scope of the term "downregulating expression of a gene product of a *Varroa destructor* mite" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Feeding *Varroa*-Specific dsRNA Prevents *Varroa* Mite Infestation

Figure 1:
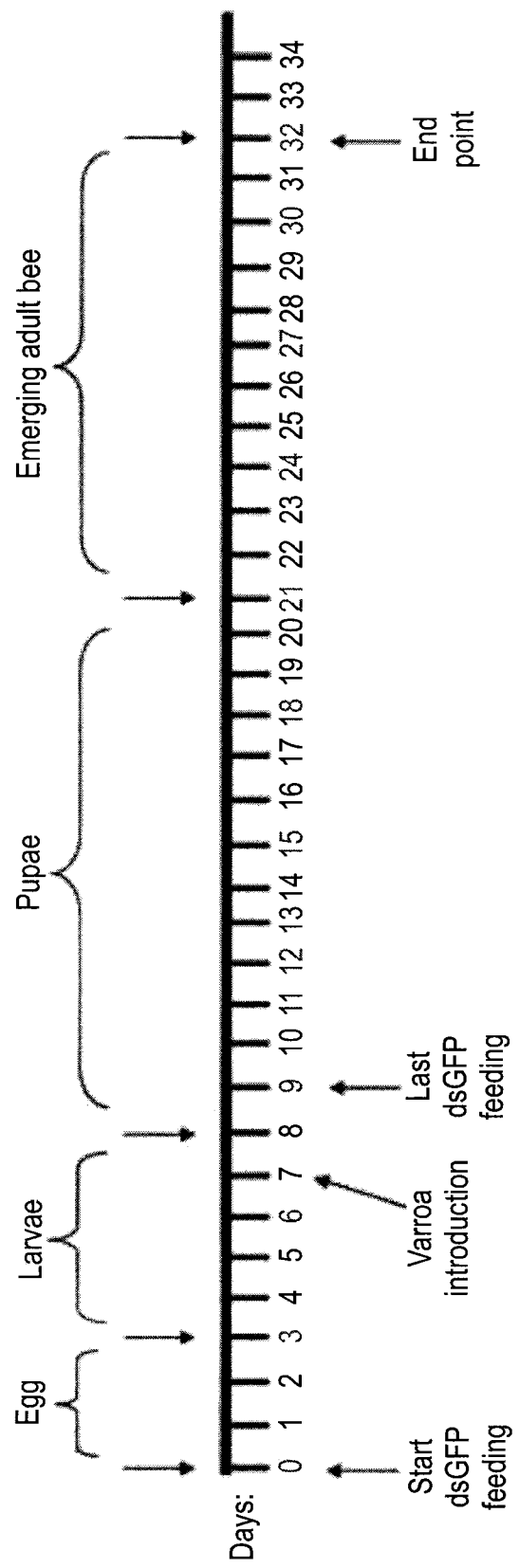
FIG. 1 is a schematic representation of the time-course of various experiment for dsRNA transfer to *Varroa* mites.
Figures 2A, 2B, 2C, 2D, 2E:
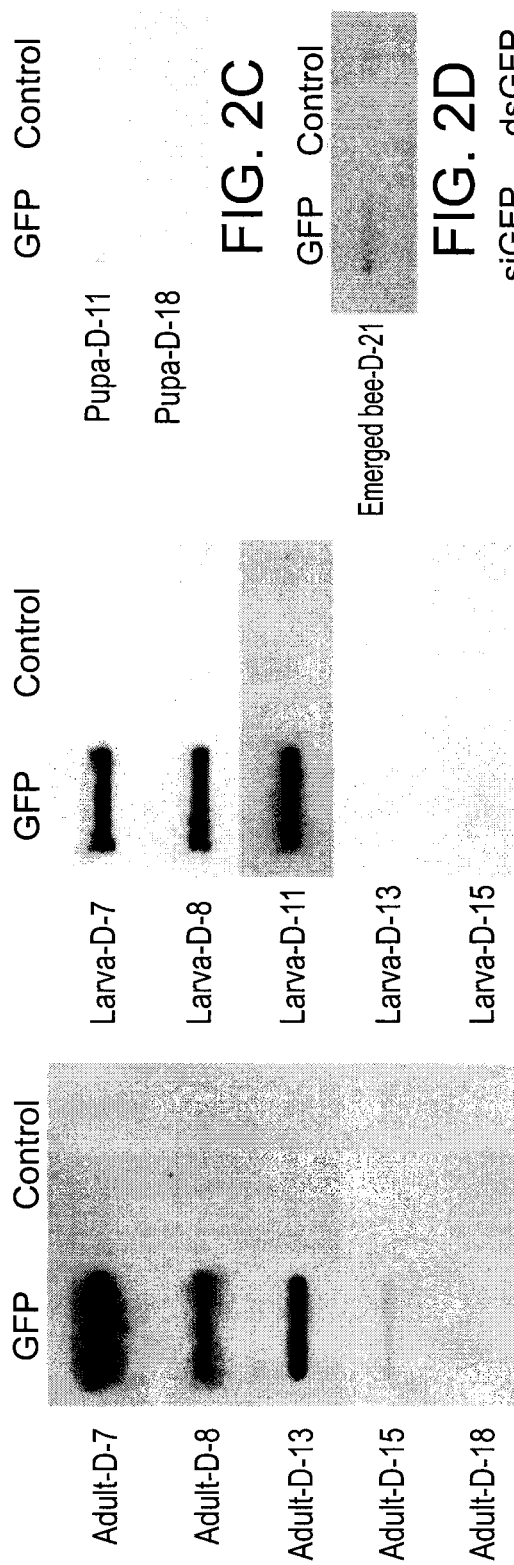
FIGS. 2A-E are photographs of the results of Slot blot analysis of the presence of dsRNA-GFP in ingested bees (FIG. 2A), in larvae fed by adult bees (FIG. 2B), in pupae (FIG. 2C), and in the newly-emerge bees (FIG. 2D). The presence of dsRNA-GFP and of siRNA derived from it was analyzed by Northern blots (FIG. 2E). D=days after administration of dsRNA-GFP to the hive.

In order to determine the effectiveness of ingested dsRNA on *Varroa* mite infestation, honeybees are provided with *Varroa* mite-specific and control dsRNA in the feed for 7 days before, and 2 days following contact with the *Varroa* mite, as illustrated in FIG. 1. Numbers of dead *Varroa* per experimental hive are counted, and sample live and dead *Varroa* are collected for molecular analysis.

Materials and Methods

Establishment of Mini-Hive Colonies:

Young, approximately 2-month-old queens, together with approximately 200 worker bees are collected from hives in a local apiary. The bees are transferred into mini-hives fitted with one mini comb that was previously built by a regular hive. All of the mini-hives are closed and placed in a temperature-controlled room (30° C.).

dsRNA Preparation:

*Varroa* mite sequences are cloned into a plasmid between two opposing T7 promoters. Following propagation of plasmid DNA, the viral fragments, including the T7 promoters, are excised and gel-purified. These serve as templates for T7-directed in-vitro transcription (MEGAscript™, Ambion, Austin Tex.). The reaction product is submitted to DNase digestion followed by phenol extraction and ethanol precipitation. The final preparation is dissolved in nuclease-free water.

dsRNA Feeding in Minihives:

5 gr. pollen supplement patties are placed on top of each comb and 10 ml of 50% sucrose solution is introduced into the hive in a sterile Petri dish nightly. The feeding is continued for 9 days and subsequently only hives in which queens had begun to lay eggs are included in the trial.

Following establishment of active hives (queens laying eggs), some of the mini-hives are supplemented with *Varroa* mite-specific (apoptosis inhibitor (IAP) gene (SEQ ID NO: 27) or non-specific control (e.g. GFP SEQ ID NO: 91) dsRNA, which is added to the 10 ml 50% sugar solution given to the hives, adjusted to approximately 1 microgram dsRNA per feed per bee, assuming all bees consume approximately the same amount of sucrose solution. dsRNA feeding is continued for six days.

*Varroa* Mite Infestation in Minihives:

7 days after feeding in active hives, some of the colonies are placed in contact with a population of *Varroa* mites. Thereafter, dsRNA treatment is continued for a further 2 days. Samples of live and dead bees (larvae and adults) are collected daily from each mini-hive post introduction of the *Varroa* mite population for 32 consecutive days. Every bee collected is frozen in liquid nitrogen and preserved at −70° C. pending molecular analysis. Vitality of the colonies are monitored by opening the hives (without smoke), withdrawing the mini-comb and photographing the mini-comb from both sides. The hive-combs are photographed daily, and the numbers of remaining live bees are monitored. The photographs are downloaded onto a computer and the total number of bees is counted for every mini-hive.

To test dsRNA toxicity, another group of hives are provided with *Varroa* mite-specific dsRNA, but is not placed in contact with the *Varroa* mite population. Two sets of hives serve as additional controls: hives that are not treated with dsRNA and are not inoculated with *Varroa* mites, and hives that were not treated with dsRNA, but were inoculated with *Varroa* mites.

RT-PCR Analysis:

Extraction of Nucleic Acids:

Total RNA is extracted from the preserved bees using the TRIREAGENT method (Sigma, St. Louis Mo., USA). Briefly, RNA is extracted by precipitation and separation by centrifugation, then resuspended in RNAsecure solution.

Real-Time RT-PCR:

Measured amounts of RNA (100 ng for viral expression analyses and 100 pg for 18S rRNA internal controls) are subjected to one-step RT-PCR using the SYBR Green PCR master mix with Taqman reverse transcriptase (Applied Biosystems, Foster City, Calif.). Real-time RT-PCR is conducted in GeneAmp PCR System 5700 (Applied Biosystems). Reactions performed without reverse transcriptase or without template should not result in any product.

Northern-Blot Analysis:

Total RNA is extracted from treated and control bees. Formaldehyde is added to the RNA to 1.8% and warmed to 65° C. The RNA, 15 pg per lane is electrophoresed on a 1.2% agarose gel at 70 V, 4° C. with stirring. The previously described amplified *Varroa* mite-RNA product is digoxigenin labeled and serves as a probe for hybridization. Detection is performed with the DIG luminescent detection kit (Roche Diagnostics GmbH, Mannheim, Germany). RNA sizes are estimated by comparison to electrophoresed RNA Molecular Weight Markers I (Roche). Hybridization is carried out at high stringency (0.1×SSC; 65° C.).

The Fate of Ingested *Varroa* Mite-Specific dsRNA in Honeybees:

In order to better understand the mechanism(s) of action by which dsRNA-*Varroa* mite protects the bees against *Varroa* mite infestation and its consequences, total RNA is extracted from dsRNA-*Varroa* mite treated, and non-treated control bees, submitted to digestion by a panel of nucleases, and separated on PAGE.

Results

The presence of dsRNA in the adult bee body in the bee larvae (fed by adult bees), in the bee pupa was determined by slot-blot hybridization with a probe for GFP. The processing of the dsRNA to siRNA was determined by Northern blots detecting small RNAs (FIGS. 2A-E).

Figure 3:
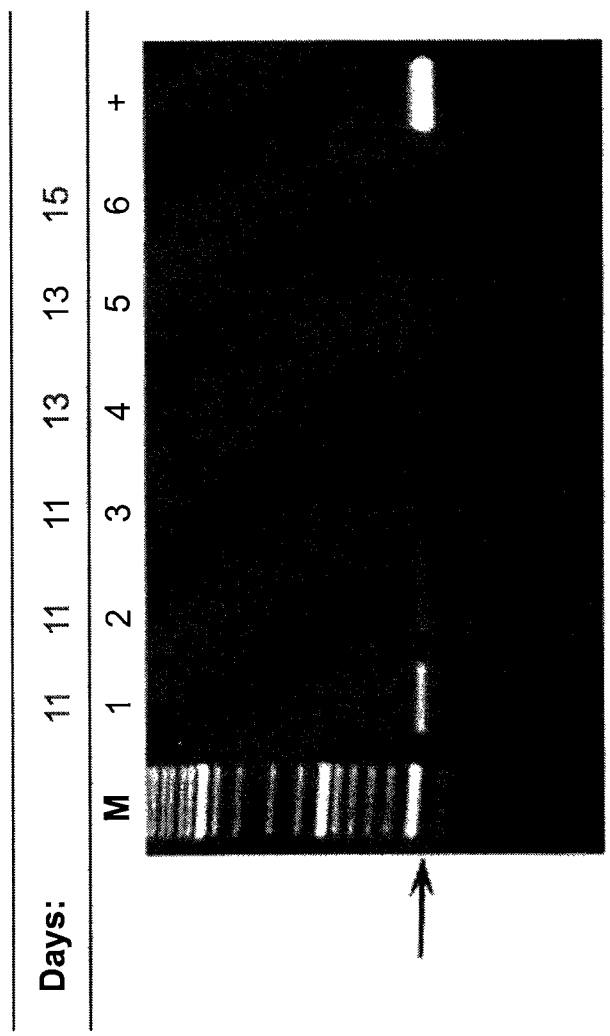
FIG. 3 is a photograph illustrating the results of RT-PCR analysis of *Varroa*-extracted RNA at the days indicated in the top row (time as indicated in FIG. 1). Green numbers (top row) indicate *Varroa* individuals which had been placed on dsRNA-GFP-ingested bees and black numbers indicate RNA from *Varroa* placed on control bees. +=positive control (a GFP-carrying plasmid).

*Varroa* individuals were placed on adult bees that had been fed for 7 days with dsRNA-GFP and on control (unfed) bees. RNA was extracted from *Varroa* at the indicated times (FIG. 1) and subjected to RT-PCR with GFP primers. The results are illustrated in FIG. 3.

Bees were fed with a segment of dsRNA for apoptosis inhibitor (IAP) gene (SEQ ID NO: 27). *Varroa* collected from that hive were analyzed by RT-PCR for the expression of the IAP gene (FIG. 4).

Example 2

Materials and Methods

Hives were fed by two different mixtures of dsRNAs corresponding to *Varroa* gene segments. All dsRNA were corresponding to gene segments that are not homologous to bee or human sequences (not carrying stretches of homologous sequences longer than 19 bases). Mixture I (Minimum treatment) contained SEQ ID NOs: 1, 13, 27, 30 and 39. Mixture II (Maximum treatment) contained SEQ ID NOs: 1, 4, 7, 10, 13, 16, 19, 22, 25, 27, 30, 33, 36 and 39. Thirty *Varroa* individuals were placed in each hive and two months later *Varroa* and bees were counted in each hive. Each treatment was repeated 3 times.

Results

No visible damage to the strength of the hive was noticed among the various hives. FIG. 5 demonstrates the reduction of *Varroa* population following treatment with dsRNAs of *Varroa*'s gene sequences.

Example 3

Large-Scale Field Trials of *Varroa*-Specific dsRNA for Prevention of *Varroa* Mite-Associated Disease of Honeybees In order to determine the effectiveness of ingested *Varroa* mite dsRNA on *Varroa* mite infestation under actual field conditions, and to assess effects on important parameters of colony health, bees in sample full size hives are provided with *Varroa* mite-specific dsRNA in the feed for 5 days before, and 4 days following infestation with *Varroa* mite.

Materials and Methods

Insect Material:

Pools of five bees from the following treatments; Remote control, *Varroa* mite-dsRNA only, *Varroa* mite only and *Varroa* mite-specific dsRNA+*Varroa* mite at each time point day 0-(day of virus application), day 7 and end point (day 42). The test was repeated several times.

RNA Extraction:

RNA is extracted using Tri-Reagent (Sigma, USA) according to protocol provided by the manufacturer. All samples are treated with DNaseI and resuspended with loading buffer (90% Formamide, 0.05 Bromophenol Blue, 0.05% Xylene cyanol) prior to loading on gel.

Gel Electrophoresis and Blot:

10 ug of freshly prepared RNA is measured using the nanodrop spectrophotometer and loaded on 12% Acrylamide gel (1:19 acrylamide:Bis acrylamide ratio) in denaturation environment (gel contains 7M Urea). After electrophoresis samples are transferred to positively charged nylon membrane (Roch, USA) using electroblotting method.

Hybridization and Signal Detection:

Membrane is hybridized with freshly prepared DNA probe of *Varroa* mite segment, taken from a region that does not correspond to the dsRNA of the *Varroa* mite-specific dsRNA itself. This is made using DIG PCR probe preparation Kit (Roch, USA) o/n 42° C. in DIG easyhyb solution (Roch, USA) according to manufacturer protocol. The membrane is washed twice with 2×SSC/0.1% SDS, than washed for stringency with 0.1×SSC/0.1% SDS in 65 OC. Membranes are further washed using DIG Wash and Block Kit (Roch, USA) according to manufacturer protocol. Detection is preformed using CSPD-star substrate (Roch, USA). Positive control is 21nt DNA primers corresponding to the hybridized sequence.

Signal is detected using membrane exposure for 2-12 hours in chemiluminator manufactured by Kodak.

Basic parameters of bee colony health (numbers of capped brood, numbers of bees in the hive, returning foragers and honey production) are assessed in hives fed *Varroa* mite-dsRNA and control hives, in the absence of *Varroa* mite infestation.

Example 4

Bi-Directional Transfer of Bee-Ingested dsRNA from Bee to *Varroa* Mite and Back to Bee Via *Varroa* Infestation In Examples 1 and 2 it was shown that dsRNA can be transferred from bees to *Varroa* directly into mites infesting bees ingesting the dsRNA, or indirectly into mites infesting larva fed by bees which ingested the dsRNA. In order to uncover whether the mites can further serve as an additional vector, transferring the dsRNA or siRNA from the mite back to a "naïve" bee via parasitisation, "naïve" bees were infested with *Varroa* following infestation of dsRNA-fed bees.

Materials and Methods dsRNA Preparation:

*Varroa*-specific and GFP dsRNA was prepared from sequences cloned into plasmids between opposing T7 promoters, as described in Example 1. Segments of selected *Varroa* genes, 200 to 450 bp in length, which did not correspond in sequence to any bee or human genes (identity of less than 21 consecutive bases), were selected for *Varroa* dsRNA production. Table I below details the sequences of the primers used for preparation of the dsRNA, and the length of the amplicon, excluding the T7 promoter sequence.

TABLE I

Primers for dsRNA preparation

| Varroa-specific dsRNA SEQUENCE (SEQ ID NO:) | Primers (F = Forward; R = Reverse)/SEQ ID NO: | Amplicon (bp) |
|---|---|---|
| SEQ ID NO: 93 | F: 5' CTAATACGACTCACTATAGGGCGAATGGAGAACATCGCACAG3'/SEQ ID NO: 107<br>R: 5' CTAATACGACTCACTATAGGGCGATTCCAGTACGTTATGTTGCTC3'/SEQ ID NO: 108 | 411 bp |
| SEQ ID NO: 94 | F: 5' CTAATACGACTCACTATAGGGCGAGGTCTTGACAACACATGCTAC3'/SEQ ID NO: 109<br>R: 5' CTAATACGACTCACTATAGGGCGACTCAGCAGAAATGATCGG3'/SEQ ID NO: 110 | 277 bp |
| SEQ ID NO: 95 | F: 5' CTAATACGACTCACTATAGGGCGAAACGCTGTGCTTCACGTA3'/SEQ ID NO: 111<br>R: 5' CTAATACGACTCACTATAGGGCGATCACGAGTAATCTCCACGA3'/SEQ ID NO: 112 | 329 bp |
| SEQ ID NO: 96 | F: 5' CTAATACGACTCACTATAGGGCGATCAGATGATTGGAACGGA3'/SEQ ID NO: 113<br>R: 5' CTAATACGACTCACTATAGGGCGAAACAGGTCTTCAAACAGCAG3'/SEQ ID NO: 114 | 380 bp |
| SEQ ID NO: 97 | F: 5' CTAATACGACTCACTATAGGGCGATCAATTCGTCTGCAGATCTC3'/SEQ ID NO: 115<br>R: 5' CTAATACGACTCACTATAGGGCGACATAAATGGCGATAAGCG3'/SEQ ID NO: 116 | 426 bp |
| SEQ ID NO: 98 | F: 5' CTAATACGACTCACTATAGGGCGAAATGAGTGTTGAGCGCGG3'/SEQ ID NO: 117<br>R: 5' CTAATACGACTCACTATAGGGCGACTCCGATCATTTGGCGTT3'/SEQ ID NO: 118 | 366 bp |
| SEQ ID NO: 99 | F: 5' CTAATACGACTCACTATAGGGCGAAGGTGACATCCGTGTTCG3'/SEQ ID NO: 119<br>R: 5' CTAATACGACTCACTATAGGGCGAATGAAGACATATAGGGTCGCT3'/SEQ ID NO: 120 | 324 bp |
| SEQ ID NO: 100 | F: 5' CTAATACGACTCACTATAGGGCGACTGTACAGGGTCCGAATATAAA3'/SEQ ID NO: 121<br>R: 5' CTAATACGACTCACTATAGGGCGATTCGAGTTTCTCAAAGGTTG3'/SEQ ID NO: 122 | 311 bp |
| SEQ ID NO: 101 | F: 5' CTAATACGACTCACTATAGGGCGACAATTGAATATGGACGTCACTC3'/SEQ ID NO: 123<br>R: 5' CTAATACGACTCACTATAGGGCGATTGAAAGCCAGCAGTAAACG3'/SEQ ID NO: 124 | 201 bp |
| SEQ ID NO: 102 | F: 5' CTAATACGACTCACTATAGGGCGACATCATCTTCTTCATCTGCTTG3'/SEQ ID NO: 125<br>R: 5' CTAATACGACTCACTATAGGGCGAGGTTCCCACGGTTGGTAT3'/SEQ ID NO: 126 | 290 bp |
| SEQ ID NO: 103 | F: 5' CTAATACGACTCACTATAGGGCGAAATGGTTTCTGCTACCTGTG3'/SEQ ID NO: 127<br>R: 5' CTAATACGACTCACTATAGGGCGAATTGGAAGCTGATACATTGG3'/SEQ ID NO: 128 | 263 bp |

TABLE I-continued

Primers for dsRNA preparation

| Varroa-specific dsRNA SEQUENCE (SEQ ID NO:) | Primers (F = Forward; R = Reverse)/SEQ ID NO: | Amplicon (bp) |
|---|---|---|
| SEQ ID NO: 104 | F: 5' CTAATACGACTCACTATAGGGCGATGGCTAATTAATAGTAGGCCG3'/SEQ ID NO: 129<br>R: 5' CTAATACGACTCACTATAGGGCGATGGAGTTTGCTACCAACCT3'/SEQ ID NO: 130 | 277 bp |
| SEQ ID NO: 105 | F: 5' CTAATACGACTCACTATAGGGCGAAGCCGGCTTCTTCTTCCT3'/SEQ ID NO: 131<br>R: 5' CTAATACGACTCACTATAGGGCGAAGTCACTGCCTGTTCCTCC3'/SEQ ID NO: 132 | 263 bp |
| SEQ ID NO: 106 | F: 5' CTAATACGACTCACTATAGGGCGATTCCGCTTCATTTGAGAAC3'/SEQ ID NO: 133<br>R: 5' CTAATACGACTCACTATAGGGCGATCTGAATCAACCTCATCGG3'/SEQ ID NO: 134 | 282 bp |
| SEQ ID NO: 92 | F: 5' TAATACGACTCACTATAGGGCGAGCCAACACTTGTCACTACTAGAAAGAGAA3'/SEQ ID NO: 135<br>R: 5' TAATACGACTCACTATAGGGCGAAGGTAATGGTTGTCTGGTAAAGGAC3'/SEQ ID NO: 136 | 431 bp |

RNA Extraction and Analysis:

Total RNA for dsRNA-GFP detection experiments was isolated from a single honeybee or from 10 *Varroa* mites, using phenol-chloroform extraction (peqGOLD Trifast™, Peqlab). Total RNA for *Varroa* dsRNA experiments was isolated from 5 *Varroa* mites by tissue homogenization binding to a mini-column, DNA-removal and RNA elution (ZR Tissue & Insect RNA MicroPrep, Zymo Research, Irvine Calif.). DNA was digested in the eluted RNA by nucleases (TURBO DNA-free kit, Ambion, Austin, Tex., USA) and the RNA was tested for DNA contamination. *Varroa* RNA was then co-precipitated with glycogen and 3 M sodium acetate in 70% ethanol and resuspended in 20 µl of RNAse-free water. The amount and quality of the RNA were determined spectrophotometrically using the nanodrop method (NanoDrop Technologies, Wilmington, Del., USA).

dsRNA-GFP Detection by RT-PCR:

dsRNA-GFP was detected by RT-PCR using Verso 1-Step RT-PCR (Thermo Scientific) with specific GFP primers (SEQ ID NOs. 135 and 136) using total RNA extracted from 10 *Varroa* or 1 honeybee as template.

Gene Expression: Real-Time RT-PCR and Semi-Quantitative RT-PCR:

RNA (400 ng) was subjected to reverse transcription with random hexamers (Verso cDNA kit, Thermo Scientific, Waltham Mass.). Each sample of the obtained cDNA was diluted 1:50 before amplification. Real-time quantitative PCR was performed by LightCycler 480 (Roche, Indianapolis, Ind.) and results analyzed with the instrument's software. Primers and probes were as detailed in Table II.

TABLE II

List of primers and probes used for real-time and semi-quantitative RT-PCR assays.

| Sequence (SEQ ID NO) | Primers/SEQ ID NO: | Amplicon (bp) |
|---|---|---|
| Varroa RNA Polymerase III (SEQ ID NO: 96) | F: 5' AAAGGGCAGGTGCTTATCAA 3'/137<br>R: 5' TGTCCAGGGTCGAGAGTAGC 3'/138 | 65 |
| Varroa vacuolar proton ATPase (SEQ ID NO: 101) | F: 5' ACCTTTTTCAAAGACCGAACC 3'/139<br>R: 5' CGAAGACTCCGTTCGAAAAC 3'/140 | 62 |
| Varroa IAP1 and IAP2, reverse (SEQ ID NO: 106) | F: 5' CTAGTTAATGGCGCGGTAGC 3'/141<br>R: 5' TCCTCCCGGTTCTACTTCAC 3'/142 | 63 |
| Varroa 18S RNA | F: 5' AATGCCATCATTACCATCCTG 3'/143<br>R: 5' CAAAAACCAATCGGCAATCT 3'/144 | 60 |
| Varroa Apoptosis Inhibitor FAS (SEQ ID NO: 104) | F: 5' ATCTGCCCACGTCAGCGTTT 3'/145<br>R: 5' GTCCGTCATTTCGGCTTTGG 3'/146 | 317 |

TABLE II-continued

List of primers and probes used for real-time and semi-quantitative RT-PCR assays.

| Sequence (SEQ ID NO) | Primers/SEQ ID NO: | Amplicon (bp) |
|---|---|---|
| Varroa Actin | F: 5' AAGTCGTACGAGCTTCCCGAC 3'/147<br>R: 5' ACAGGGAGGCAAGGATGGAAC 3'/148 | 336 |

The real-time PCR program was as follows: 95° C. for 10 min, followed by 45 cycles of 95° C. for 10 seconds and 60° C. for 30 seconds, and finally 40° C. for 30 seconds. 18S rRNA was used as an internal control for the standardization of RNA levels.

The semi-quantitative PCR program was as follows: 95° C. for 10 min, followed by 40 cycles, each consisting of 95° C. for 10 seconds and 65° C. and 55° C. for 30 seconds for the apoptosis inhibitor (FAS, primers were SEQ ID Nos. 145 and 146) and its internal standardization control (actin, primers were SEQ ID Nos. 147 and 148), respectively, followed by 72° C. for 30 seconds. Reaction products were sampled every three cycles starting from cycle 31 for FAS and from cycle 29 for actin, the sample incubated for 5 min at 72° C. and stored at −20° C. Samples were analyzed on a 1.2% agarose gel. Each semi-quantitative PCR experiment was repeated three times.

Regimen of dsRNA-GFP Feeding:

1-day-old bees were placed in four plastic containers (30 bees per container). Two containers were fed with 30 µg dsRNA-GFP in 200 jpl of 50% sucrose solution for 8 days, and the other two control containers fed 50% sucrose solution without dsRNA. Mite infestation was initiated by introduction of adult female *Varroa* (n=30) into each container on day 5. After 3 days, *Varroa* that were attached to bees were removed and collected, and their RNA isolated for dsRNA-GFP analysis. To test for bidirectional transfer of dsRNA-GFP from bee to mite and on to another bee, newly emerged, untreated bees were infested by some of the *Varroa* that had been detached from the dsRNA-fed bees for 4 days and the bee's RNA isolated for dsRNA-GFP analysis. Each day, bees in all containers were given an additional 1 ml sucrose solution after finishing their treatment. In addition, bees had free access to a pollen patty consisting of 70% pollen mixed with sugar powder.

To test for indirect transfer of dsRNA-GFP from adult bee to bee larva and on to mite feeding on the hemolymph of the developing bee in a sealed cell, a cup of bees (about 250) and a laying queen were introduced into each mini-hive (two repetitions in each of two enclosures). dsRNA-GFP (200 µg per hive) was provided daily in 5 ml 50% sucrose solution for 8 days. Thirty *Varroa* mites were introduced to the hives on the fifth day. Adult female *Varroa* were collected from sealed cells from day 11 till day 30 and their RNA was isolated for dsRNA-GFP analysis.

Figure 8:
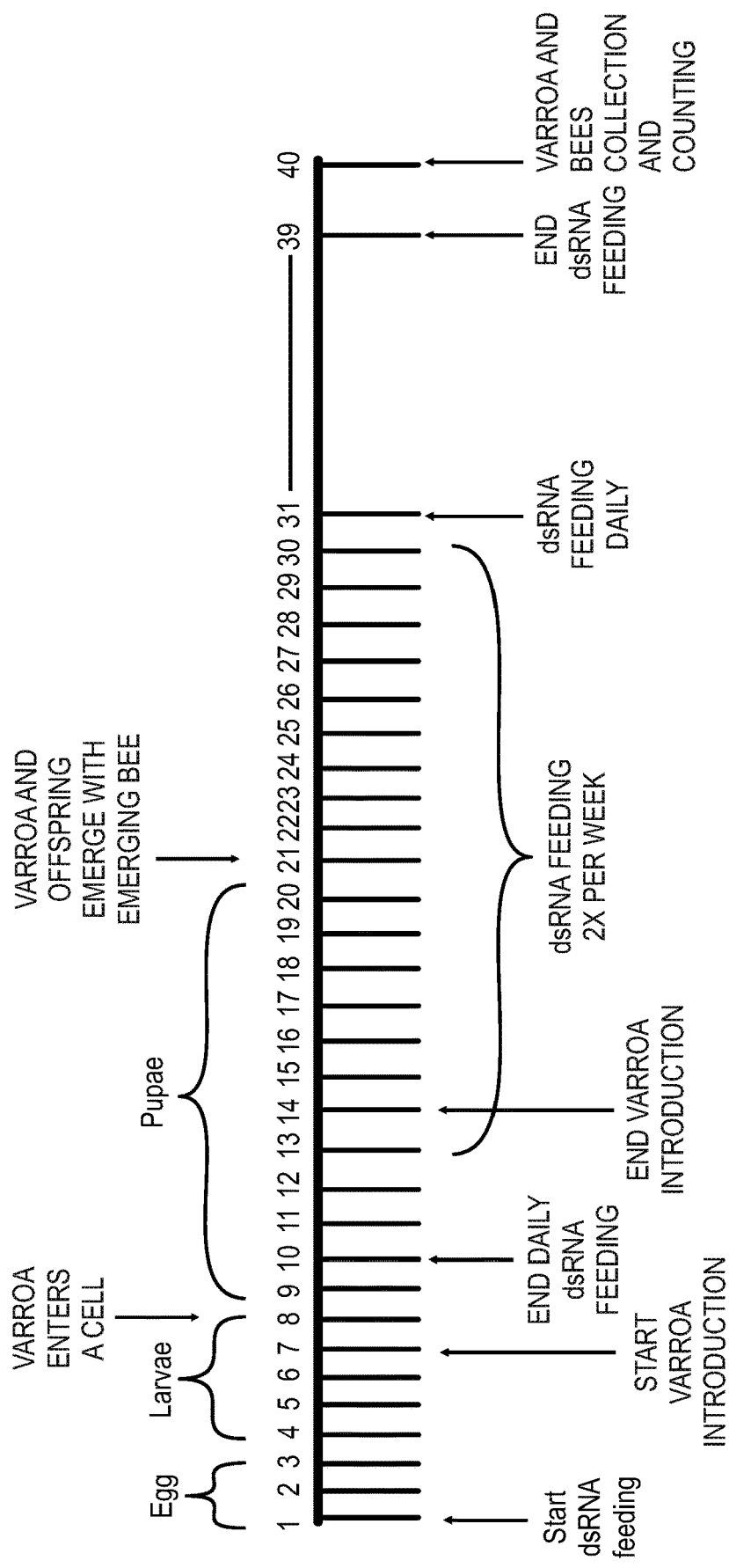
FIG. 8 is a schematic representation of a 60-day feeding experiment for *Varroa*-specific dsRNA, including honeybee feeding regimen and testing schedule for *Varroa* gene expression (bottom) and the honeybee feeding *Varroa* mite life cycle.

Feeding *Varroa*-Specific dsRNA Sequences:

The experiment with *Varroa* dsRNA was conducted in mini-hives, 12 mini-hives per repetition, for three repetitions. In each repetition, a cup of bees and a laying queen were placed in each mini-hive. Three mini-hives were randomly assigned to one of four netted enclosures, each representing a different feeding treatment. Bees were fed 5 ml of 50% sucrose solution in troughs placed in each mini-hive. The four treatments were: 1) sucrose solution only (untreated control), 2) Mixture I (200 µg each of five dsRNAs added to the sugar solution), 3) Mixture II (200 µg each of 14 dsRNAs added to the sugar solution), and 4) dsRNA-GFP (200 µg dsRNA) serving as a dsRNA-positive control. Bees that fully consumed the treatment solutions were supplemented with candy (67% sugar powder and 33% honey). In addition, the bees were routinely fed pollen patties (70% pollen and 30% sugar powder). Each repetition of the experiment lasted for 60 days (FIG. 8). Bees in each treatment were fed the respective solution daily for the first 10 days and for the last 14 days, and twice a week in the interim. Infestation with *Varroa* mites was initiated by introducing mites into each mini-hive from day 7 until day 14. In the first repetition, 30 mites were introduced into each mini-hive; in the latter two repetitions, 100 mites were introduced into each mini-hive. On day 60, all mature bees were collected, counted and shaken with 70% ethanol overnight in order to collect and count *Varroa* mites falling off the bees. All capped brood cells were opened to collect and count *Varroa* mites. Number of mites per bee included mature and developing (capped brood) bees. *Varroa* mites, adult bees, emerging bees and pupae were stored for molecular analyses.

Statistical Analysis:

Statistical analyses were conducted with JMP statistical software version 9 (SAS Institute, Cary, N.C., USA). Statistical significance was set at $P<0.05$. To test for significant differences in relative expression, one-way ANOVA was conducted on ddCt values. Treatment was the main factor. To test for differences in *Varroa* mite population, two-way ANOVA was conducted on numbers of *Varroa* per bee in a block design with treatment as main effect and experimental replicate as block. To test for differences in total bee population, a similar two-way ANOVA was conducted on the total number of bees (capped brood and adults). Significant differences between treatments were tested by the Tukey-Kramer (HSD) test.

Results

Direct and Indirect Horizontal Transfer of dsRNA Between Bees and *Varroa* Mites:

As shown in Examples 1 and 2, bees fed with dsRNA can transfer dsRNA sequences to *Varroa* mites via infestation, and to bee larva and pupae via feeding by dsRNA-bearing bees.

Figure 6:
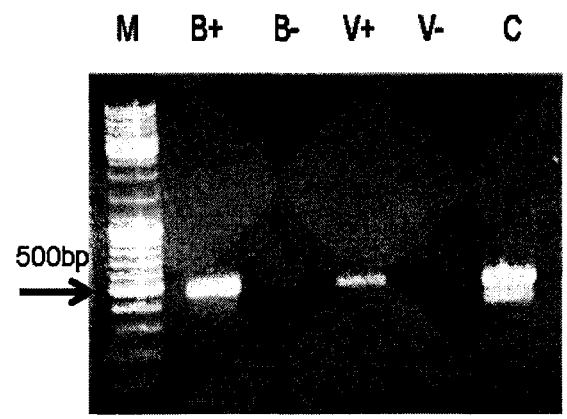
FIG. 6 is a photograph illustrating dsRNA transmission from adult bees to *Varroa* mites. RT-PCR was performed on RNA from bees fed with GFP– specific dsRNA and untreated control bees (lanes B+, B–, respectively) and RNA from *Varroa* mites parasitizing the treated or untreated control bees (lanes V+ and V–, respectively). Lane C: Positive control (GFP– bearing plasmid). M=size markers.
Figure 7:
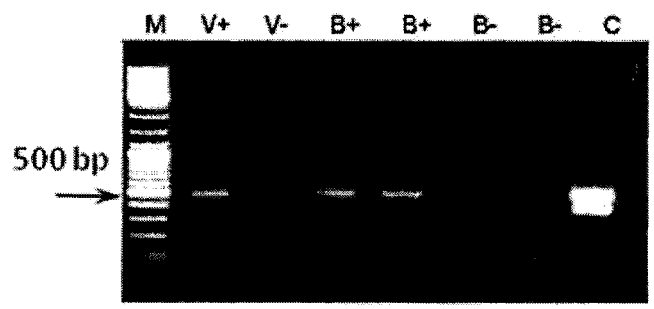
FIG. 7 is a photograph illustrating dsRNA transmission from bees to *Varroa* and *Varroa* back to bees. Bees were infested with either *Varroa* mites carrying the GFP dsRNA or siRNA(V+) or control mites (V) devoid of GFP-specific dsRNA or siRNA. B+ is RNA amplified from bees infested with GFP-dsRNA or siRNA-fed mites, B– is RNA amplified from bees infested with control mites devoid of GFP-specific dsRNA or siRNA. Lane C: Positive control (GFP-bearing plasmid). M=size markers.

Direct transfer of GFP-specific sequences from adult bees fed with dsRNA-GFP in a 50% sucrose solution for 8 days to *Varroa* mites via infestation on the fifth day of feeding was verified by RT-PCR of the mite RNA after 3 days of infestation (FIG. 6, see lanes B+ and V+).

Indirect horizontal transfer of GFP-specific sequences from bees to mites via larva/pupae was verified by detection, by PCR, of GFP-specific sequences in *Varroa* RNA collected from mites feeding on larval/pupae fed by nurse bees ingesting GFP-specific dsRNA-containing sugar solution (results not shown).

To test for bidirectional horizontal transfer, mites feeding on bees ingesting GFP-specific dsRNA were removed from the bees after 3 days and introduced into a container with untreated, "naïve" bees for 4 days. RT-PCR of *Varroa* and bee RNA reveals that GFP-specific RNA sequences were detectable in RNA extracts of "naïve" bees which had been parasitized by *Varroa* mites previously infesting bees carrying GFP-dsRNA (see FIG. 7, lanes B− and B+). The presence of GFP-specific sequences in the parasitized "naïve" bees indicates reciprocal, bi-directional transfer of the GFP-specific sequences derived from dsRNA, from bee to *Varroa* and then to another bee by mite infestation.

These results clearly point to a surprising additional means for transmission, from dsRNA-fed bees to mites and back to "naïve" bees, of RNAi sequences derived from the dsRNA. Such bi-directional transmission can be effective in further disseminating the silencing effect of ectoparasite (e.g. mite)-specific dsRNA fed to bees.

Example 5

Silencing of *Varroa* Gene Expression Mediated by Bees Ingesting dsRNA

Specific silencing of *Varroa* gene expression via feeding of dsRNA to the bees was tested in mini-hives consisting of about 250 worker bees and a laying queen. Minihives were provided with bee feed (sucrose solution) with either one of two mixtures of the *Varroa* dsRNA: Mixture I contained sequences derived from five *Varroa* gene sequences (SEQ ID NOs. 93, 96, 100, 104 and 106) or Mixture II contained 14 *Varroa* gene sequences (SEQ ID NOs. 93-106). Note that sequence represented by SEQ ID NO: 101 does not appear in Mixture I. Controls were mini-hives fed with an irrelevant dsRNA (dsGFP) or only sucrose solution.

*Varroa* mites were introduced following 1 week of feeding, the mites added every day for a week (see protocol in FIG. 8). At the end of 60 days *Varroa* mites were samples from all four treatment groups, and transcription levels of four selected *Varroa* genes determined by real-time or semi-quantitative RT-PCR, as described in Example 4.

Results

Figure 9A:
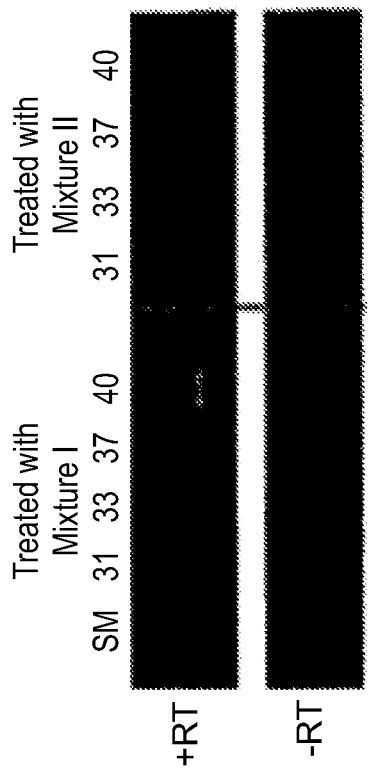
FIGS. 9A-9F illustrate silencing of *Varroa* gene expression following horizontal transfer of *Varroa*-specific dsRNA from bee to *Varroa* mite.
Figure 9B:
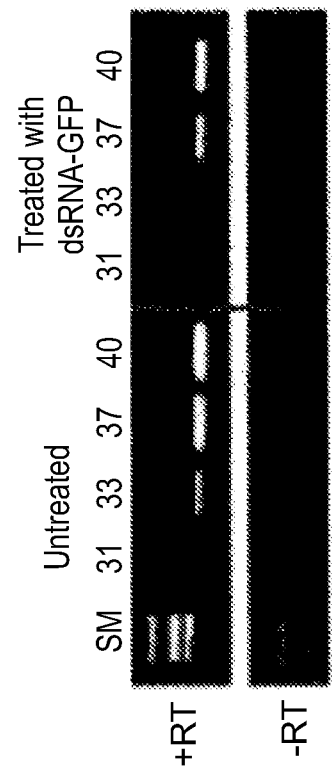
Figure 9C:
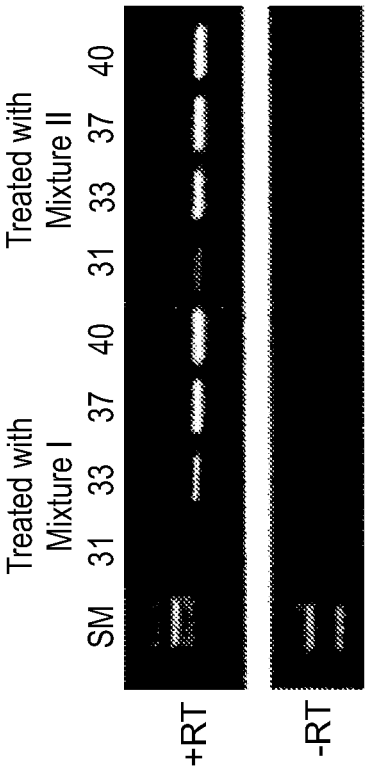
Figure 9D:
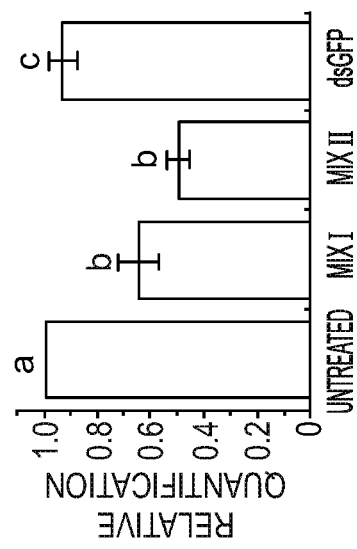
Figure 9E:
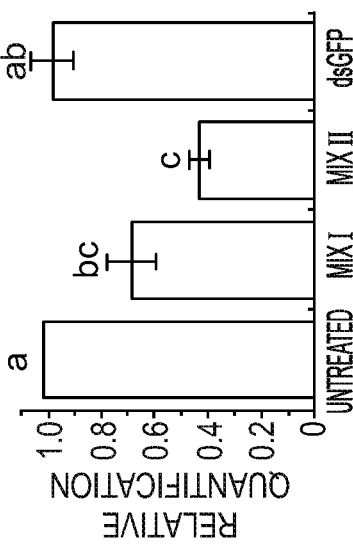
Figure 9F:
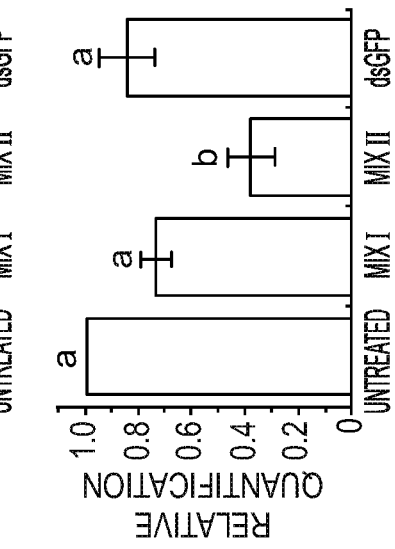

Real-Time PCR of *Varroa* RNA (FIGS. 9A-9C) clearly indicates approximately 35 to 60% reduction in expression of three representative *Varroa*-specific genes (RNA polymerase III, 9A; IAP1 and IAP2, 9B and Vacuolar proton ATPase, 9C) resulting from feeding the bees *Varroa*-specific dsRNA. Semi-quantitative PCR of *Varroa* RNA (FIG. 9D) illustrates even more dramatic, potentially disruptive silencing of *Varroa* apoptosis-inhibiting FAS gene expression by feeding bees apoptosis inhibitor FAS-specific dsRNA, in a highly specific manner (see FIGS. 9E and 9F).

Effect of Gene Silencing of *Varroa* Gene Expression on *Varroa* Infestation in Hives:

Following detecting the silencing of several *Varroa* genes, the effect on mite infestation was investigated.

Figure 10:
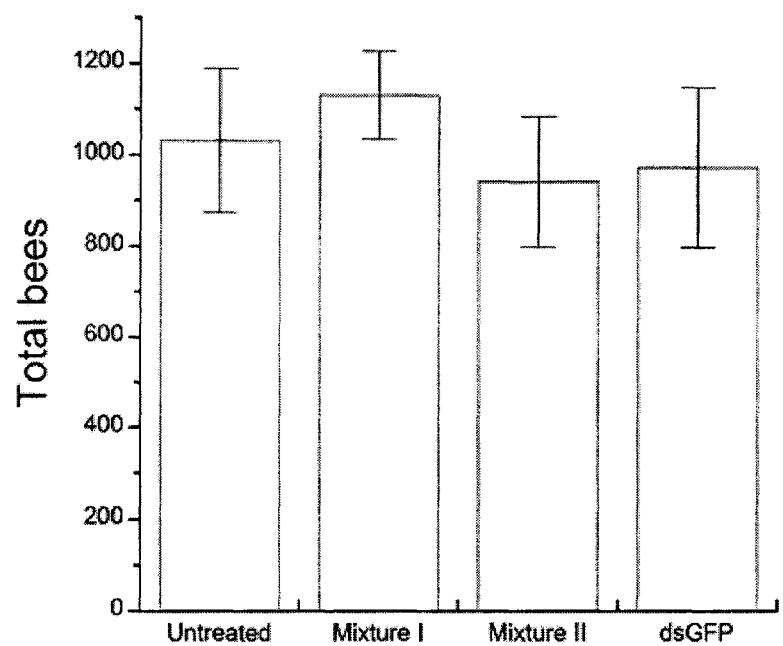
FIG. 10 is a graph showing the mean (+SE) total number of bees (capped brood and adults) in bees fed a mixture of 5 *Varroa*-specific dsRNAs (Mixture I) or a mixture of 14 *Varroa*-specific dsRNAs (Mixture II), or control bees fed irrelevant (dsGFP) dsRNA or untreated (Untreated). No significant differences were detected.

In order to determine whether feeding the dsRNA mixtures affected bee survival, all mature bees and sealed brood in the mini-hives at completion of the protocol (see FIG. 8) were counted. Bee population size did not differ between control and dsRNA-treated mini-hives ($F_{3,29}$=0.62, P=0.608; FIG. 10). The results were similar when brood and adult bees were analyzed separately (not shown). Thus, feeding the dsRNA mixtures is not deleterious to bees, indicating no off-target effect of the feeding.

In order to determine whether bee-mediated silencing of *Varroa* genes could be employed for control of mite infestation in hives, the number of *Varroa* individuals per bee was determined by actual examination of the mite population on mature bees and in sealed brood cells at the completion of the protocol.

*Varroa* infestation was reduced in bees of mini-hives fed with *Varroa* dsRNA compared to the controls ($F_{3,29}$=5.65, P=0.0035; FIG. 11). The effect was even more significant in bees of hives fed Mixture II, which targeted more genes than Mixture I, reducing *Varroa* infestation by an average 53% compared to control hives fed the dsRNA-GFP control, and by 61% compared to hives receiving no dsRNA control.

Taken together, these results indicate that feeding bees *Varroa*-specific dsRNA results in both direct and indirect transmission of mite-specific dsRNA and siRNA to mites feeding off the bees and larval/pupae in the hives, as well as bi-directional transmission of the *Varroa*-specific RNA sequences from parasitizing mites back to "naïve" bees, and that feeding the *Varroa*-specific dsRNA is an effective and safe method for reducing mite infestation in the hives.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising at least one nucleic acid agent which comprises a nucleic acid sequence which down-regulates expression of a gene product of a *Varroa destructor* mite, and wherein said nucleic acid agent does not comprise a permeation enhancing agent selected from the group consisting of a virus, a polyamine, a polycation, a lipopolyamine, an anionic lipid, a neutral lipid, a pH sensitive lipid, transferrin, biotin, a serum protein, a glycoprotein, polyethylene glycol, and a cationic lipid.

2. The composition of claim 1, wherein said at least one nucleic acid agent comprises at least five nucleic acid agents, for down-regulating ATPase subunit A, RNA polymerase III, Inhibitor of apoptosis (IAP), FAS apoptotic inhibitor and α-Tubulin, each of said at least five nucleic acid agent targeting a different gene.

3. The composition of claim 1, wherein said at least one nucleic acid agent comprises at least six nucleic acid agents, for down-regulating ATPase subunit A, RNA polymerase I, RNA polymerase III, Inhibitor of apoptosis (IAP), FAS apoptotic inhibitor and α-Tubulin, each of said at least six nucleic acid agents for targeting a different gene.

4. The composition of claim 2, wherein said nucleic acid agents are as set forth in SEQ ID Nos: 1, 13, 27, 30 and 39.

5. The composition of claim 3, wherein said nucleic acid agents are as set forth in SEQ ID Nos: 1, 4, 7, 10, 13, 16, 19, 22, 25, 27, 30, 33, 36 and 39.

6. The composition of claim 1, wherein said composition is in solid form.

7. The composition of claim 1, wherein said composition is in liquid form.

8. The composition of claim 1, wherein said composition comprises protein.

9. The composition of claim 7, wherein said liquid is a sucrose solution.

10. The composition of claim 7, wherein said liquid is a corn syrup solution.

11. The composition of claim 7, wherein said liquid further comprises a carbohydrate or sugar supplement.

12. The composition of claim 1, wherein said nucleic acid sequence comprises a sequence complementary to at least 21 nucleotides of *Varroa destructor* mite messenger RNA (mRNA).

13. The composition of claim 12, wherein said *Varroa destructor* mite mRNA encodes a polypeptide selected from the group consisting of ATPase subunit A, RNA polymerase III, IAP, FAS apoptotic inhibitor, and α-Tubulin.

14. The composition of claim 1, wherein said nucleic acid sequence is greater than 15 base pairs in length.

15. The composition of claim 1, wherein said nucleic acid sequence is greater than 19 to 25 base pairs in length.

16. The composition of claim 1, wherein said nucleic acid sequence is greater than 30 base pairs in length.

17. The composition of claim 1, wherein said at least one nucleic acid agent is selected from the group consisting of a double-stranded RNA (dsRNA), an antisense RNA, and a ribozyme.

18. The composition of claim 17, wherein said dsRNA is selected from the group consisting of a small inhibitory RNA (siRNA), a short-hairpin RNA (shRNA), and a micro-RNA (miRNA).

\* \* \* \* \*